US009790528B2

(12) United States Patent
Panaccione et al.

(10) Patent No.: US 9,790,528 B2
(45) Date of Patent: Oct. 17, 2017

(54) PRODUCTION OF LYSERGIC ACID BY GENETIC MODIFICATION OF A FUNGUS

(71) Applicant: West Virginia University, Morgantown, WV (US)

(72) Inventors: Daniel G. Panaccione, Morgantown, WV (US); Sarah L. Robinson, Independence, WV (US)

(73) Assignee: West Virginia University, Morgantown, WV (US)

( * ) Notice: Subject to any disclaimer, the term of this patent is extended or adjusted under 35 U.S.C. 154(b) by 0 days.

(21) Appl. No.: 14/739,382

(22) Filed: Jun. 15, 2015

(65) Prior Publication Data

US 2015/0361471 A1    Dec. 17, 2015

Related U.S. Application Data

(60) Provisional application No. 62/012,658, filed on Jun. 16, 2014.

(51) Int. Cl.
  *C12P 17/18*    (2006.01)
  *C12N 15/52*    (2006.01)

(52) U.S. Cl.
  CPC ............ *C12P 17/182* (2013.01); *C12N 15/52* (2013.01)

(58) Field of Classification Search
  None
  See application file for complete search history.

(56) References Cited

U.S. PATENT DOCUMENTS

| 3,314,961 A | 4/1967 | Rutschmann et al. | |
|---|---|---|---|
| 2015/0211036 A1* | 7/2015 | Naesby | C12N 9/001 435/122 |

FOREIGN PATENT DOCUMENTS

WO    2014/030096 A2    2/2014

OTHER PUBLICATIONS

Notification of Transmittal of the International Search Report (Forms PCT/ISA/220 and PCT/ISA/210) and the Written Opinion of the International Searching Authority (Form PCT/ISA/237) issued on Dec. 1, 2015, in the International Application No. PCT/US15/35784. (19 pages).
Ščigelová et al., "Biotransformation of Ergot Alkaloids by Plant Cell Cultures with High Peroxidase Activity," Biotechnology Letters, (Nov. 1995), vol. 17, No. 11, pp. 1213-1218.
Singer et al., "High-Throughput TAIL-PCR as a Tool to Identify DNA Flanking Insertions," Methods in Molecular Biology, (2003), vol. 236, pp. 241-272.

(Continued)

*Primary Examiner* — Robert Mondesi
*Assistant Examiner* — Richard Ekstrom
(74) *Attorney, Agent, or Firm* — Buchanan Ingersoll & Rooney PC

(57) ABSTRACT

The present invention provides a method of producing lysergic acid and other ergot alkaloids by genetic modification of a fungus. A strain of fungus comprising *Aspergillus fumigatus* (*A. fumigatus*) and expressing one or more genes of the ergot alkaloid biosynthesis pathway from one or more fungus selected from the group consisting of *Epichloë festucae* var. *loliixEpichloë typhina* isolate Lp1 (*E.* sp. Lp1); *Claviceps* species; *Claviceps africana* (*C. africana*); *Claviceps gigantea* (*C. gigantea*); *Epichloë coenophiala* and *Periglandula* species, wherein gene easA or gene easM is inactivated in said *A. fumigatus*, is provided.

18 Claims, 14 Drawing Sheets

(56) References Cited

OTHER PUBLICATIONS

Tooley et al., "Analysis of Claviceps Africana and C. Sorghi from India using AFLPs, EF-1α gene intron 4, and β-tubulin gene intron 3," Mycological Research, (Apr. 2006), vol. 110, No. 4, pp. 441-451.
Tsai et al., "The Developmentally Regulated alb1 Gene of Aspergillus fumigatus: Its Role in Modulation of Conidial Morphology and Virulence," Journal of Bacteriology, (Jun. 1998), vol. 180, No. 12, pp. 3031-3038.
Unsöld et al., "Overproduction, Purification and Characterization of FgaPT2, a Dimethylallyltryptophan Synthase from Aspergillus Fumigatus," Microbiology, (May 2005), vol. 151, pp. 1499-1505.
Unsöld et al., "Reverse Prenyltransferase in the Biosynthesis of Fumigaclavine C in Aspergillus fumigatus: Gene Expression, Purification, and Characterization of Fumigaclavine C Synthase FGAPT1," ChemBioChem, (Jan. 2006), vol. 7, No. 1, pp. 158-164.
Wallwey et al., "Ergot Alkaloid Biosynthesis in Aspergillus Fumigatus: Conversion of Chanoclavine-I to Chanoclavine-I Aldehyde Catalyzed by a short-chain Alcohol Dehydrogenase FgaDH," Arch Microbiol, (Feb. 2010), vol. 192, No. 2, pp. 127-134.
Wallwey et al., "Ergot Alkaloid Biosynthesis in Aspergillus Fumigatus: Conversion of Chanoclavine-I Aldehyde to Festuclavine by the Festuclavine Synthase FgaFS in the presence of the old yellow enzyme FgaOx3," Organic & Biomolecular Chemistry, (Aug. 2010), vol. 8, No. 15, pp. 3500-3508.
Wallwey et al., "Ergot Alkaloids: Structure Diversity, Biosynthetic Gene Clusters and Functional Proof of Biosynthetic Genes," Natural Product Reports, (Mar. 2011), vol. 28, No. 3, pp. 496-510.
Winblad et al., "Therapeutic Use of Nicergoline," Clinical Drug Investigation, (Sep. 2008), vol. 28, No. 9, pp. 533-552.
Agurell et al., "A New Ergot Alkaloid from Mexican Maize Ergot," Acta Pharm. Suecica, (Jun. 1965), vol. 2, pp. 231-238.
Barrow et al., "Biosynthesis of Dihydroergot Alkaloids," Tetrahedron Letter; the International Organ for the Rapid Publication of Preliminary Communications in Organic Chemistry, (1974), vol. 15, No. 16, pp. 1557-1560.
Baskys et al., "Vascular Dementia: Pharmacological Treatment Approaches and Perspectives," Clinical Interventions in Aging, (2007), vol. 2, No. 3, pp. 327-335.
Beliveau et al., "8-Hydroxylation of Agroclavine and Elymoclavine by Fungi," Lloydia, (Sep. 1966), vol. 29, No. 3, pp. 234-238.
Cheng et al., "A Role for Old Yellow Enzyme in Ergot Alkaloid Biosynthesis," Journal of the American Chemical Society, (Jan. 26, 2010), vol. 132, No. 6, pp. 1776-1777.
Cheng et al., "Controlling a Structural Branch Point in Ergot Alkaloid Biosynthesis," Journal of the American Chemical Society, (Aug. 25, 2010), vol. 132, No. 37, pp. 12835-12837.
Coyle et al., "An Ergot Alkaloid Biosynthesis Gene and Clustered Hypothetical Gene form Aspergillus Fumigatus," Applied and Environmental Microbiology, (Jun. 2005), vol. 71, No. 6, pp. 3112-3118.
Coyle et al., "An Old Yellow Enzyme Gene Controls the Branch Point between Aspergillus Fumigatus and Claviceps Purpurea Ergot Alkaloid Pathways," Applied and Environmental Microbiology, (Jun. 2010), vol. 76, No. 12, pp. 3898-3903.
Du et al., "Fumigaclavine C Inhibits Tumor Necrosis Factor α Production via Suppression of toll-like Receptor 4 and Nuclear Factor κB Activation in Macrophages," Life Science, (Aug. 15, 2011), vo, 89, No. 7-8, pp. 235-240.
Fleetwood et al., "A Complex Ergovaline Gene Cluster in Epichloë Endophytes of Grasses," Applied and Environmental Microbiology, (Apr. 2007), vol. 73, No. 8, pp. 2571-2579.
Florea, "Towards Elimination and Genetic Manipulation of Ergot Alkaloid Production in Fungal Endophytes," University of Kentucky Doctoral Dissertations, (2009), 74 Pages.
Gao et al., "Genome Sequencing and Comparative Transcriptomics of the Model Entomopathogenic Fungi Metarhizium anisopliae and M. Acridum," PLOS Genetics, (Jan. 2011), vol. 7, No. 1, e1001264, pp. 1-18.
Ge et al., "Bioactive Alkaloids from Endophytic Aspergillus Fumigatus," Journal of Natural Products, (2009), vol. 72, No. 4, pp. 753-755.
Goetz et al., "Ergot Cluster-Encoded Catalase is Required for Synthesis of Chanoclavine-I in Aspergillus Fumigatus," Current Genetics, (Jun. 2011), vol. 57, No. 3, pp. 201-2011.
Gröger et al., "Chapter 5 Biochemistry of Ergot Alkaloids-Achievements and Challenges," The Alkaloids: Chemistry and Biology, (1998), vol. 50, pp. 171-218.
Haarmann et al., "The Ergot Alkaloid Gene Cluster in Claviceps Purpurea: Extension of the Cluster Sequence and Intra Species Evolution," Phytochemistry, (Jun. 2005), vol. 66, No. 11, pp. 1312-1320.
Haarmann et al., "Identification of the Cytochrome P450 Monooxygenase that Bridges the Clavine and Ergoline Alkaloid Pathways," ChemBioChem, (Apr. 2006), vol. 7, No. 4, pp. 645-652.
Havemann et al., "Cyclolization of D-Lysergic Acid Alkaloid Peptides," Chemistry & Biology, (Jan. 16, 2014), vol. 21, No. 1, pp. 146-155.
Hofmann, "LSD—My Problem Child," McGraw-Hill Book Company, (1980), ISBN 0-07-029325-2, 102 pages.
Hynes et al., "Isolation of Genomic Clones Containing the amdS Gene of Aspergillus Nidulans and Their Use in the Analysis of Structural and Regulatory Mutations," Molecular and Cellular Biology, (Aug. 1983), vol. 3, No. 8, pp. 1430-1439.
Kren et al., "Ergot: The Genus Claviceps," (2003), https://books.google.com/books?isbn=0203304195.
Langfelder et al., "Identification of a Polyketide Synthase Gene (pksP) of Aspergillus Fumigatus Involved in Conidial Pigment Biosynthesis and Virulence," Medical Microbiology and Immunology, (Oct. 1998), vol. 187, No. 2, pp. 79-89.
Leuchtmann et al., "Nomenclatural Realignment of Neotyphodium Species with Genus Epichloë," Mycologia, (Mar.-Apr. 2014), vol. 106, No. 2, pp. 202-215.
Lin et al., "Biosynthesis of Ergot Alkaloids, Synthesis of 6-Methyl-8-Acetoxymethylene-9-Ergolene and Its Incorporation into Ergotoxine by Claviceps," The Journal of Organic Chemistry, (Jun. 1973), vol. 38, No. 12, pp. 2249-2251.
Liu et al., "Amplification of Genomic Sequences Flanking T-DNA Insertions by Thermal Asymmetric Interlaced Polymerase Chain Reaction," Methods in Molecular Biology, (2005), vol. 286, pp. 341-348.
Liu et al., "High-Efficiency Thermal Asymmetric Interlaced PCR for Amplification of Unknown Flanking Sequences," BioTechniques, (Nov. 2007), vol. 43, No. 5, pp. 649-656.
Lorenz et al., "Comparison of Ergot Alkaloid Biosynthesis Gene Clusters in Claviceps Species Indicates Loss of Late Pathway Steps in Evolution of C. fusiformis," Applied and Environmental Microbiology, (Nov. 2007), vol. 73, No. 22, pp. 7185-7191.
Lorenz et al., "The Ergot Alkaloid Gene Cluster: Functional Analyses and Evolutionary Aspects," Phytochemistry, (Oct.-Nov. 2009), vol. 70, No. 15-16, pp. 1822-1832.
Maier et al., "Microsomal Oxygenases Involved in Ergoline Alkaloid Biosynthesis of Various Claviceps Strains," Journal of Basic Microbiology, (1988), vol. 28, No. 1-2, pp. 83-93.
Matossian, "Poisons of the Past: Molds, Epidemics, and History," Yale University Press, New Haven, (1989), https://books.google.com/books?isbn=0300051212.
Matuschek et al., "New Insights into Ergot Alkaloid Biosynthesis in Claviceps Purpures: An Agroclavine Synthase EasG Catalyses, via a non-enzymatic adduct with Reduced Glutathione, the Conversion of Chanoclavine-I Aldehyde to Agroclavine," Organic & Biomolecular Chemistry, (Jun. 7, 2011), vol. 9, No. 11, pp. 4328-4335.
Morren et al., "Where is Dihydroergotamine Mesylate in the Changing Landscape of Migraine Therapy?," Expert Opinion on Pharmacotherapy, (Dec. 2010), vol. 11, No. 18, pp. 3085-3093.
Panaccione et al.,"A Cyclic Peptide Synthetase Gene Required for Pathogenicity of the Fungus Cochliobolus carbonum on Maize," Proceeding of the National academy of Sciences of the United States of America, (Jul. 15, 1992), vol. 89, No. 14, pp. 6590-6594.

(56) References Cited

OTHER PUBLICATIONS

Panaccione et al., "Biochemical Outcome of Blocking the Ergot Alkaloid Pathway of a Grass Endophyte," Journal of Agricultural and Food Chemistry, (Oct. 22, 2003), vol. 51, No. 22, pp. 6429-6437.

Panaccione et al., "Abundant Respirable Ergot Alkaloids from the Common Airborne Fungus *Aspergillus fumigatus*," Applied and Environmental Microbiology, (Jun. 2005), vol. 71, No. 6, pp. 3106-3111.

Panaccione, "Origins and Significance of Ergot Alkaloid Diversity in Fungi," FEMS Microbiology Letters, (Oct. 1, 2005), vol. 251, No. 1, pp. 9-17.

Panaccione et al., "Analysis and Modification of Ergot Alkaloid Profiles in Fungi," Methods in Enzymology, (2012), vol. 515, pp. 267-290.

Panaccione et al., "Bioactive Alkaloids in Vertically Transmitted Fungal Endophytes," Functional Ecology, (Apr. 2014), vol. 28, No. 2, pp. 299-314.

Panaccione et al., "Effects of Ergot Alkaloids on Food Preference and Satiety in Rabbits, As Assessed with Gene-Knockout Endophytes in Perennial Ryegrass (*Lolium perenne*)," Journal of Agricultural and Food Chemistry, (Jun. 28, 2006), vol. 54, No. 13, pp. 4582-4587.

Pažoutová,"The Phylogeny and Evolution of the Genus *Claviceps*," Mycological Research, (Mar. 2001), vol. 105, No. 3, pp. 275-283.

Perez-Lloret et al., "Dopamine Receptor Agonists for the Treatment of Early or Advanced Parkinson's Disease," CNS Drugs, (Nov. 2010), vol. 24, No. 11, pp. 941-968.

Riederer et al., "D-Lysergyl Peptide Synthetase from the Ergot Fungus *Claviceps purpurea*," The Journal of Biological Chemistry, (Nov. 1, 1996), vol. 271, No. 44, pp. 27524-27530.

Robinson et al., "Chemotypic and Genotypic Diversity in the Ergot Alkaloid Pathway of Aspergillus Fumigatus," Mycologia, (Jul.-Aug. 2012), vol. 104, No. 4, pp. 804-812.

Robinson et al.,"Heterologous Expression of Lysergic Acid and Novel Ergot Alkaloids in Aspergillus Fumigatus," Applied and Environmental Microbiology, (Oct. 2014), vol. 80, No. 20, pp. 6465-6472.

Ryan et al., "Partial Reconstruction of the Ergot Alkaloid Pathway by Heterologous Gene Expression in Aspergillus Nidulans," Toxins, (Feb. 22, 2013), vol. 5, No. 2, pp. 445-455.

Schardl et al., "Origin of a Fungal Symbiont of Perennial Ryegrass by Interspecific Hybridization of a Mutualist with the Ryegrass Choke Pathogen, Epichloë Typhina," Genetics, (Apr. 1994), vol. 136, No. 4, pp. 1307-1317.

Schardl et al., "Ergot Alkaloids-Biology and Molecular Biology," Alkaloids Chem Biol., (2006), vol. 63, 44 pages.

Schardl et al., "Chemotypic Diversity of Epichloae, Fungal Symbionts of Grasses," Fungal Ecology, (Jun. 2012), vol. 5, No. 3, pp. 331-344.

Schardl et al., "Plant-Symbiotic Fungi as Chemical Engineers: Multi-Genome Analysis of the Clavicipitaceae Revels Dynamics of Alkaloid Loci," PLOS Genetics, (Feb. 2013), vol. 9, No. 2, pp. e1003323-1-e1003323-26.

Schardl et al., "Currencies of Mutualisms: Sources of Alkaloid Genes in Vertically Transmitted Epichloae," Toxins, (2013), vol. 5, No. 6, pp. 1064-1088.

* cited by examiner

FIGURE 3

PRODUCTION OF LYSERGIC ACID BY GENETIC MODIFICATION OF A FUNGUS

CROSS-REFERENCE TO RELATED APPLICATION

This utility patent application claims the benefit of co-pending U.S. Provisional Patent Application Ser. No. 62/012,658, filed on Jun. 16, 2014. The entire contents of U.S. Provisional Patent Application Ser. No. 62/012,658 is incorporated by reference into this utility patent application as if fully written herein.

GOVERNMENT SUPPORT

This invention was made with government support under Grant No. 2012-67013-19384 and Grant No. 2008-35318-04549 awarded by USDA NIFA and Hatch funds. The government has certain rights in this invention.

SEQUENCE LISTING

Following the Abstract of the Disclosure is set forth a paper copy of the SEQUENCE LISTING in written form (.PDF format) having SEQ ID NO:1 through SEQ ID NO:7. The paper copy of the SEQUENCE LISTING is incorporated by reference into this application. A SEQUENCE LISTING in computer-readable form (.txt file) having SEQ ID NO:1 through SEQ ID NO. 7 accompanies this application and is incorporated into this application. A Statement Of Identity Of Computer-Readable Form And Written Sequence Listing also accompanies this application.

BACKGROUND OF THE INVENTION

1. Field of the Invention

The present invention relates to a method of producing lysergic acid by genetically modifying a fungus. A method for producing dihydroergot alkaloids (dihydrolysergic acid and dihydrolysergol) and lysergol are also provided. This invention discloses the heterologous expression of lysergic acid and novel ergot alkaloids in *Aspergillus fumigatus*.

2. Description of the Background Art

Ergot alkaloids derived from lysergic acid have impacted human health for millennia, initially as toxins and more recently as pharmaceuticals; however, important aspects of ergot alkaloid biosynthesis remain unsolved. Ergot alkaloids are pharmaceutically and agriculturally relevant secondary metabolites synthesized by several species of fungi. Historically, ergot alkaloids caused periodic mass human poisonings due to infection of grain crops by the ergot fungus *Claviceps purpurea* (Matossian, 1989). Agriculturally, ergot alkaloids in forage grasses colonized by endophytic Epichloë spp. [including many fungi recently realigned from genus *Neotyphodium* (Leuchtmann et al., 2014)] continue to reduce weight gain and fitness in grazing animals (Schardl et al., 2012; Panaccione et al., 2014). Clinically, the structural similarities of ergot alkaloids to monoamine neurotransmitters allow them to treat cognitive and neurological maladies including dementia, migraines, and Parkinson's disease in addition to endocrine disorders such as type 2 diabetes and hyperprolactinemia (e.g., Baskys and Hau, 2007; Morren and Galvez-Jimenez, 2010; Perez-Lloret and Rascol, 2010; Winblad et al., 2008) (see ergot chart below). Indeed, the neurotransmitter-mimicking activities of ergot alkaloids are most infamously evident in the psychoactive drug LSD, a semisynthetic lysergic acid derivative (Hoffman, 1980). Several of the more important pharmaceutical ergot alkaloids are semi-synthetic dihydroergot alkaloids (dihydro prefix abbreviated as DH in subsequent text); natural DHergot alkaloids producers exist, but the genetic basis for their biosynthesis is unknown. In some embodiments of the invention, controlling the ergot alkaloid pathway will facilitate metabolic engineering strategies to produce libraries of ergot derivatives with potentially altered pharmacology. Moreover, by understanding different branches of the ergot alkaloid pathway, we will be able to prepare alternate starting materials for more efficient pharmaceutical synthesis.

| Examples of pharmaceutical ergot alkaloids and their uses and derivations[1] | | | |
|---|---|---|---|
| Ergot Alkaloid (brand name) | Clinical use(s) | Current semisynthetic derivation | Efficient semisynthetic derivation |
| Nicergoline (Sermion) | Senile dementia, Alzheimer's, cerebral thrombosis | From LA via other ergot alkaloids | From DHlysergol, lysergol, or DHLA |
| Cabergoline (Caberlin, Dostinex) | Hyperprolactinemia, pituitary prolactinomas | From LA via other ergot alkaloids | From DHLA |
| Pergolide (Permax) | Parkinson's (elsewhere, withdrawn in USA, 2007) | From LA via other ergot alkaloids | From DHlysergol, lysergol, or DHLA |
| Bromocriptine (Parlodel, Cycloset) | Type 2 diabetes, Parkinson's, hyperprolactinemia | From α-ergocryptine or LA via other ergot alkaloids | |
| Ergoloid mesylates (Hydergine) | Senile dementia | From ergopeptines or LA via other ergot alkaloids | From DHergopeptines or DHLA |
| DHergotamine (DHE 45, Migranal) | Migraines | From ergotamine or LA via other ergot alkaloids | From DHergotamine or DHLA |

[1]Abbreviations: LA, lysergic acid; DH, dihydro (meaning lacking a double bond in fourth ring of ergoline nucleus)

Lysergic acid that is used for pharmaceutical production is presently synthesized in one of two methods know by those skilled in the art generally. The first known method involves growing crops of rye that are later infected with an ergot alkaloid producing fungus *Claviceps purpurea*. During infection, *C. purpurea* produces structures called sclerotia in place of the native rye grains. The sclerotia contain complex alkaloids that are derived from lysergic acid. At the flowering stage of the rye, the fungus (which has been grown for 5-6 weeks in culture) is inoculated onto the flowers of the grass. Depending on weather conditions, the sclerotia can be harvested after 4-6 weeks. Total ergot alkaloids must be extracted from the sclerotia. All the alkaloids must then be hydrolyzed in a strong base to produce lysergic acid. The second known method is to grow mutant strains of either *C. purpurea* or *Claviceps paspali* in either stationary surface cultures or submerged cultures-all containing a growth medium. There are three cultivation steps: preinoculating tanks, seed tanks, and production fermenters, each requiring a different growth medium. The cultures are grown for several weeks. Our experiences have optimum alkaloid production after 7 weeks of growth. From our experience, alkaloid production is not guaranteed in this method. Similar to the first known method, total complex alkaloids must be extracted and hydrolyzed in this second known method to produce lysergic acid before purification of lysergic acid. The following publications describe the generalities of these known methods of producing lysergic acid: (1) Annis, S. L., and Panaccione, D. G. 1998. Presence of peptide synthetase gene transcripts and accumulation of ergopeptines in *Claviceps purpurea* and *Neotyphodium coenophialum*. Canadian Journal of Microbiology 44:80-86; (2) Coyle, C. M., Cheng, J. Z., O'Connor, S. E., Panaccione, D. G. 2010. An old yellow enzyme gene controls the branch point between *Aspergillus fumigatus* and *Claviceps purpurea* ergot alkaloid pathways. Applied and Environmental Microbiology 76:3 898-3903; and (3) Kren, V., and Cvak, L. 1999. Ergot, The Genus *Claviceps*. Harwood Academic Publishers, Amsterdam, page 518.

Unlike the known methods of producing lysergic acid as described above, the present invention provides an efficient method of producing lysergic acid and its purification directly without the need to utilize complex alkaloids.

SUMMARY OF THE INVENTION

The present invention provides methods for the efficient production of lysergic acid, dihydrolysergric acid, and lysergol.

Another embodiment of this invention provides a strain of fungus comprising *Aspergillus fumigatus* (*A. fumigatus*) and expressing one or more genes of the ergot alkaloid biosynthesis pathways from one or more fungus selected from the group consisting of:
  a. *Epichloë festucae* var. *loliixEpichloë typhina* isolate Lp1 (*E.* sp. Lp1);
  b. *Claviceps* species;
  c. *Claviceps africana* (*C. africana*);
  d. *Claviceps gigantea* (*C. gigantea*);
  e. *Periglandula* species; and
  f. *Epichloë coenophiala*, wherein gene easA or gene easM is inactivated in said *A. fumigatus*. This strain includes one or more genes of the ergot alkaloid biosynthesis that are selected from the group consisting of: easA and cloA. Preferably, the strain includes wherein said gene easA is inactivated in said *A. fumigatus*, and said one or more fungus is *E.* sp. Lp1. Another embodiment provides wherein the strain wherein said gene easA is inactivated in said *A. fumigatus*, and said one or more fungus is a *Periglandula* species or an Epichloë coenophiala strain that produces lysergol. More preferably, this strain includes wherein said gene easA is inactivated in said *A. fumigatus*, and said one or more fungi are a *Periglandula* species and *E.* sp. Lp1, wherein said expressing gene easA is from a *Periglandula* species or Epichloë coenophiala and said expressing gene cloA is from *E.* sp. Lp1. Another embodiment provides the strain including wherein said gene easA is inactivated in said *A. fumigatus*, and said one or more fungi are a *Periglandula* species or *Epichloë coenophiala* and *E.* sp. Lp1, wherein said expressing gene cloA is from a *Periglandula* species or *Epichloë coenophiala* and said expressing gene easA is from *E.* sp. Lp1. Yet another embodiment provides the strain wherein said gene easM is inactivated in *A. fumigatus*, said one or more fungus is *E.* sp. Lp1, and said expressing one or more genes of the ergot alkaloid biosynthesis is cloA. Another embodiment includes wherein the strain includes wherein said gene easM is inactivated in *A. fumigatus*, said one or more fungus is *C. africana*, and said expressing one or more genes of the ergot alkaloid biosynthesis is cloA. Another embodiment provides the strain wherein said gene easM is inactivated in said *A. fumigatus*, said one or more fungus is *C. gigantea*, and said expressing one or more genes of the ergot alkaloid biosynthesis is cloA.

Another embodiment provides a method for producing lysergic acid comprising inactivating an ergot alkaloid biosynthesis pathway gene from the fungus *A. fumigatus* and expressing genes easA and cloA from the fungus *E.* sp. Lp1, wherein said inactivated ergot alkaloid biosynthesis pathway gene is easA of *A. fumigatus*.

Another embodiment provides a method for producing novel ergot alkaloids comprising inactivating an ergot alkaloid biosynthesis pathway gene from the fungus *A. fumigatus* and expressing genes easA and cloA from the fungus *E.* sp. Lp1, wherein said inactivated ergot alkaloid biosynthesis pathway gene is easA of *A. fumigatus*.

Another embodiment provides a method for producing dihydrolysergic acid (DHLA) comprising inactivating gene easM in *A. fumigatus* and expressing gene cloA from *E.* sp. Lp1 or gene cloA from *C. africana* in said *A. fumigatus* strain.

Another embodiment provides a method for producing dihydrolysergol (DHlysergol) comprising inactivating gene easM in *A. fumigatus* and expressing one or more genes of the ergot alkaloid biosynthesis from *C. gigantea* selected from the group consisting of:
  a. cloA; and
  b. cloA and easA,
  wherein said gene(s) from *C. gigantea* are expressed in said *A. fumigatus* strain.

Another embodiment of this invention provides a strain of fungus comprising a species of a fungus and expressing one or more genes of the ergot alkaloid biosynthesis pathways from one or more of said fungus, wherein said fungus has a pathway similar to *A. fumigatus*. Preferably, the strain includes wherein said one or more genes of the ergot alkaloid biosynthesis are selected from the group consisting of: easA and cloA. More preferably, the strain includes wherein said easA or cloA genes from said ergot alkaloid producing fungi are functionally similar to the genes from *Claviceps purpurea* or any of *Epichloë* species.

Another embodiment of this invention provides a method of producing ergot alkaloids in *A. fumigatus* comprising expressing ergot alkaloid synthesis genes from other fungi in *A. fumigatus* easA knockout or easM knockout, allowing native prenyl transferase EasL act on any ergot alkaloids so produced for producing prenylated alkaloids.

Another embodiment provides a method of producing ergot alkaloids in a strain of *A. fumigatus* comprising expressing a bidirectional easA/easG promoter of *A. fumigatus* to drive expression of oxidase genes in the *A. fumigatus* EasA knock-out background. Preferably, the method includes wherein said strain includes oxidase gene cloA from *E.* sp. Lp1. Preferably, the method includes providing a EasA gene from *E.* sp. Lp1 that is expressed in said *A. fumigatus* EasA knock-out background. More preferably, the method includes wherein said EasA gene from *E.* sp. Lp1 includes expression of cloA from *E.* sp. Lp1.

Another embodiment provides a method for the production of lysergic acid comprising providing for the expression of EasA/CloA in *A. fumigatus* easA knockout.

Another embodiment includes a method of producing a festuclavine-accumulating strain of *A. fumigatus* comprising a knock-out of the easM allele.

Another embodiment provides a method for producing lysergic acid in *A. fumigatus* easA knock-out providing amplifying *E.* sp. Lp1 easA and *E.* sp. Lp1 cloA for producing lysergic acid.

Another embodiment of this invention provides a method for accumulating lysergol comprising amplifying easA and cloA from *Periglandula* in plant material selected from the group consisting of *Stictocardia tiliifolia, S. beraviensis, Argyreia*, and *Ipomoea* species or *Epichloë coenophiala* from *Lolium arundinaceum* for accumulating lysergol.

Another embodiment provides a method for producing lysergol comprising providing expressing *Periglandula* sp. easA and *P.* sp. cloA or *Epichloë coenophiala* cloA in a *A. fumigatus* easA knock-out strain for producing lysergol.

Another embodiment provides a method for producing lysergol comprising expressing *P.* sp. easA or *Epichloë coenophiala* easA and Epichloë sp. Lp1 cloA in a *A. fumigatus* easA knock-out strain for producing lysergol.

Another embodiment provides a method for producing lysergol comprising *A. fumigatus* easA knock-out strain through expression of *E.* sp. Lp1 easA and *P.* sp. cloA or *Epichloë coenophiala* cloA for producing lysergol.

Preferably the methods of producing lysergol of this invention include amplifying said easA and cloA based on degenerate primers designed to anneal to versions of each gene.

Another embodiment of this invention provides a method for producing dihydrolysergic acid comprising expressing *C. africana* cloA under the control of a *A. fumigatus* easA promoter in *A. fumigatus* easM knock-out strain for producing dihydrolysergic acid.

Another embodiment of this invention provides a method for producing dihydrolysergic acid comprising expressing *C. africana* easA and *C. africana* cloA or *E.* sp. Lp1 cloA using a *A. fumigatus* easA/easG promoter for producing dihydrolysergic acid.

Another embodiment of this invention provides a method for producing dihydrolysergol comprising expressing *C. gigantea* cloA in *A. fumigatus* easM knock-out for producing dihydrolysergol. Preferably, the method includes joining said cloA to a easA promoter of *A. fumigatus* to form a cloA construct and introducing said cloA construct into *A. fumigatus* easM knock-out utilizing cotransformation with pBCphleo. More preferably, the method includes adding a *C. gigantea* easA expressed in a *A. fumigatus* easM knock-out as part of said cotransformation.

Another embodiment of this invention provides a strain of fungus comprising SEQ ID NO:4 or a strain of fungus comprising SEQ ID NO:7.

BRIEF DESCRIPTION OF THE DRAWINGS

FIG. 1 shows the intermediates and products of the ergot alkaloid pathway (as composited from branches found in different fungi).

FIG. 2 shows ergot alkaloid synthesis (eas) clusters from *E.* sp. Lp1 (A) and *Aspergillus fumigatus* (B), and design of transformation construct (C).

Figure 3:
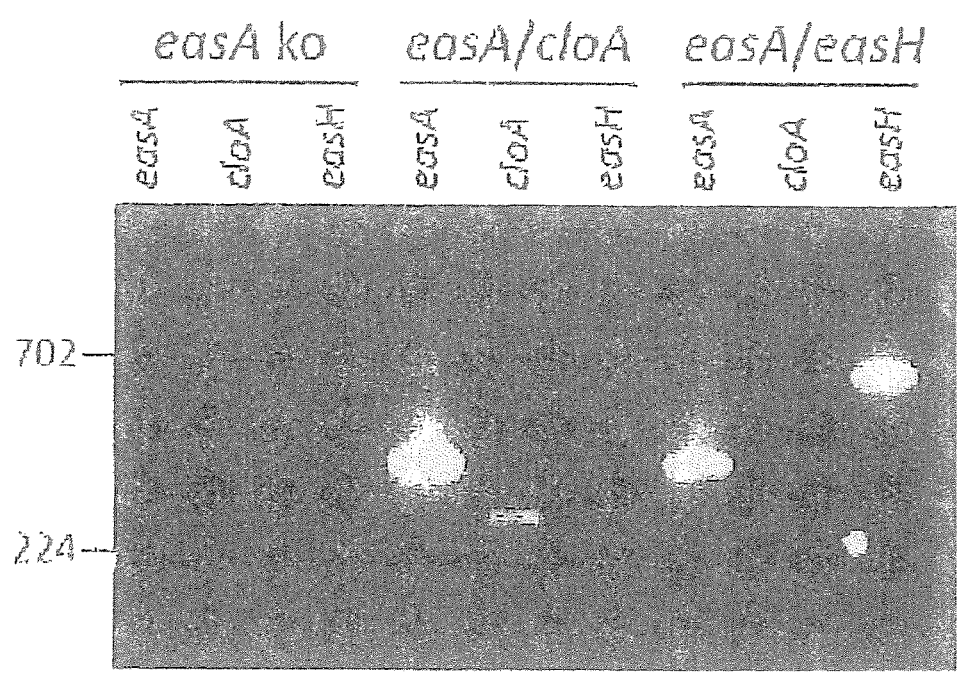

FIG. 3 shows qualitative RT-PCR demonstrating accumulation of mRNA from indicated genes in *A. fumigatus* easA ko transformants.

FIG. 4 shows an analysis of ergot alkaloids from transformed strains of *A. fumigatus.*

FIG. 5 shows mass spectra of two unknown alkaloids with hypothesized structures.

FIG. 6 shows (A) branch points and critical steps in the biosynthesis of ergot alkaloids in different lineages of fungi; and (B) rarely encountered ergot alkaloids (prophetic) originating from mutant pathways.

FIG. 7 shows ergot alkaloid synthesis (eas) gene clusters from several fungi.

FIG. 8 shows dual gene expression construct for expressing easA and cloA of *E.* sp. Lp1 in *A. fumigatus* easA ko. This construct was generated using fusion PCR techniques understood by those persons skilled in the art.

FIG. 9 shows analysis of ergot alkaloids from transformed strains of *A. fumigatus.*

FIG. 10 shows alternate origins of agroclavine and the origin of setoclavine.

FIG. 11 shows knockout of easM results in accumulation of festuclavin and eliminates fumigaclavins.

FIG. 12 shows the pathway from agroclavin to lysergic acid.

FIG. 13 shows pathway from festuclavine to dihydrolysergic acid (DHLA).

FIG. 14 shows *Aspergillus fumigatus* ergot alkaloid pathway.

DETAILED DESCRIPTION OF THE INVENTION

Different lineages of fungi produce distinct classes of ergot alkaloids. Lysergic acid-derived ergot alkaloids produced by fungi in the Clavicipitaceae are particularly important in agriculture and medicine. The pathway to lysergic acid is partly elucidated, but the gene encoding the enzyme that oxidizes the intermediate agroclavine is unknown. We investigated two candidate agroclavine oxidase genes from the fungus *Epichloë festucae* var. *lolii*×*Epichloë typhina* isolate Lp1 (henceforth *E.* sp. Lp1), which produces lysergic acid-derived ergot alkaloids. Candidate genes easH and cloA were expressed in a mutant strain of the mold *Aspergillus fumigatus*, which typically produces a subclass of ergot alkaloids not derived from agroclavine or lysergic acid. Candidate genes were co-expressed with the *E.* sp. Lp1 allele of easA, which encodes an enzyme that catalyzed the synthesis of agroclavine from an *A. fumigatus* intermediate; the agroclavine then served as substrate for the candidate agroclavine oxidases. Strains expressing easA and cloA from *E.* sp. Lp1 produced lysergic acid from agroclavine, a process requiring a cumulative six electron oxidation and a double bond isomerization. Strains that accumulated excess agroclavine (as a result of *E.* sp. Lp1 easA expression in the absence of cloA) metabolized it into two novel ergot alkaloids for which structures were determined on the basis of mass spectra and precursor feeding studies. Our data indicate CloA catalyzes multiple reactions to produce lysergic acid from agroclavine and that combining genes from different ergot alkaloid pathways provides an effective strategy to engineer important pathway molecules and novel ergot alkaloids.

Ergot alkaloids derived from lysergic acid have impacted human lives for millennia, initially as toxins and more recently as pharmaceuticals; however, important aspects of lysergic acid biosynthesis remain unsolved. We combined genes from ergot alkaloid pathways from two fungal lineages to produce lysergic acid in the genetically tractable fungus *Aspergillus fumigatus*. In doing so, we demonstrated that a previously identified gene encodes additional activities required for lysergic acid biosynthesis. We also found that combining genes from ergot alkaloid pathways from different fungi resulted in production of completely novel ergot alkaloids. In some embodiments of the invention, controlling the ergot alkaloid pathway will facilitate production and development of pharmaceuticals for the treatment of dementia and other cognitive or neurological disorders.

Ergot alkaloids (EA) are agriculturally and pharmaceutically relevant secondary metabolites synthesized by several species of fungi. Historically, EA caused periodic mass poisonings due to infection of grain crops by the ergot fungus *Claviceps purpurea* (1). Agriculturally, EA in forage grasses colonized by endophytic Epichloë spp. [including many fungi recently realigned from genus *Neotyphodium* (2)] reduce weight gain and fitness in grazing animals (3, 4). Clinically, the structural similarities of EA to neurotransmitters allow EA to treat cognitive and neurological maladies including dementia, migraines, and Parkinson's disease (5-7). The neurotransmitter-mimicking activities of EA are most infamously evident in the psychoactive drug LSD, a semisynthetic EA derivative (8).

Representatives of two major families of fungi—the Clavicipitaceae and the Trichocomaceae—produce EA. All EA-producing fungi share early pathway steps before diverging to produce lineage-specific classes of EA (FIG. 1). Members of the Clavicipitaceae, including *Claviceps purpurea* or the endophytic Epichloë species such as *E. festucae* var. *loliixE. typhina* isolate Lp1 (2, 9) (henceforth called *E.* sp. Lp1), synthesize lysergic acid-based alkaloids in which the D ring of the ergoline nucleus is unsaturated between carbons 9 and 10, and carbon 17 is highly oxidized (FIG. 1) (4, 10, 11). EA-producing fungi in the Trichocomaceae, such as the opportunistic human pathogen *Aspergillus fumigatus*, produce clavine-based derivatives in which the D ring is saturated and carbon 17 remains reduced as a methyl group (12, 13).

The branch point of the pathway occurs during D ring closure. In *A. fumigatus*, the 8,9 double bond in chanoclavine aldehyde is reduced by the enzyme EasA, allowing the aldehyde group free rotation to interact with the secondary amine to promote ring closure via Schiff base formation (14-16). The resulting iminium ion is subsequently reduced by EasG to form festuclavine (16, 17), which may be modified at carbons 9 and/or 2 to form various fumigaclavine derivatives (FIG. 1). Most EA-producing fungi in the Clavicipitaceae, however, synthesize the 8,9 unsaturated clavine agroclavine from chanoclavine aldehyde via the activity of an alternate version of EasA that acts as an isomerase rather than a reductase (15, 17). In *C. purpurea* and Epichloë spp., agroclavine is oxidized to form elymoclavine, and elymoclavine is further oxidized and isomerized to form lysergic acid (FIG. 1). Lysergic acid is then incorporated into ergopeptines and/or lysergic acid amides. Lysergic acid derivatives are the EA used for pharmaceutical development, but these compounds are produced exclusively in clavicipitaceous fungi and not in model organisms that would facilitate their modification and development.

The genetics of many steps in the EA pathway has been characterized; however, the identity of the gene encoding the oxidase that converts agroclavine to elymoclavine has remained elusive. All known genes involved in ergot alkaloid synthesis (eas genes) in both *A. fumigatus* and the Clavicipitaceae have been found in clusters (FIG. 2) (11, 18-24). The roles of many of the genes in eas clusters have been determined by gene knockout or by expression of coding sequences in *Escherichia coli*. Among the genes in eas clusters of lysergic acid-producing fungi, two genes stand out as candidates to encode the enzyme that oxidizes agroclavine. The gene labeled easH encodes a product with high similarity to dioxygenases (10, 19, 25); at the time this present work was conducted, its role in the pathway had not been tested, but very recently EasH has been demonstrated to oxidize lysergyl-peptide lactams to facilitate their cyclization to ergopeptines (25). This gene is present in both *A. fumigatus* and Epichloë spp.; however, the copy found in *A. fumigatus* (which lacks agroclavine and lysergic acid derivatives) is a pseudogene (10). The gene named cloA, for clavine oxidase (26), is a second candidate. Haarmann et al. (26) showed that CloA was required for oxidation of carbon 17 of elymoclavine during synthesis of lysergic acid and speculated that CloA also oxidized the same carbon in agroclavine. Only fungi that produce lysergic acid-derived alkaloids contain cloA in their eas clusters (18-24).

To test each candidate gene, a heterologous expression system was designed using an *A. fumigatus* easA knock out (easA ko) (15) as the host strain, which allowed for precise pathway control based on insertion of an agroclavine-specific allele of easA. Constructs used for transformation contained three elements: easA from *E.* sp. Lp1, a bidirectional easA/easG promoter from *A. fumigatus*, and the candidate gene (either easH or cloA) amplified from *E.* sp. Lp1 (FIG. 2). Co-expression of the *E.* sp. Lp1 allele of easA in the easA ko background of *A. fumigatus* allows accumulation of agroclavine (15, 17), which served as substrate for the enzyme expressed from the candidate gene in the construct. This combinatorial approach allowed clear testing of the two candidate genes and identification of the gene encoding the agroclavine-oxidizing enzyme. Moreover, production of agroclavine in *A. fumigatus* allowed accumulation of novel ergot alkaloids as a result of the activity of native *A. fumigatus* enzymes on agroclavine.

Results

*Aspergillus fumigatus* easA ko was successfully transformed with constructs for expressing either easA/easH or easA/cloA of *E.* sp. Lp1. Evidence of successful transformation and expression of the *E.* sp. Lp1 genes included accumulation of mRNA from both *E.* sp. Lp1 genes introduced with a particular construct (FIG. 3). Further evidence of successful expression of the introduced genes was the altered ergot alkaloid profiles observed by HPLC with fluorescence detection (FIG. 4, Table 1). As described previously (15), the recipient strain, *A. fumigatus* easA ko, accumulated primarily chanoclavine and also small quantities of agroclavine [arising via a non-catalyzed keto-enol tautomerization of chanoclavine aldehyde (15)] and larger quantities of its oxidation product setoclavine. Transformants expressing *E.* sp. Lp1 easA/easH accumulated chanoclavine and significantly more agroclavine and setoclavine/isosetoclavine than did the non-transformed recipient strain, indicating successful expression of the easA allele of *E.* sp. Lp1 without further modification of the ergot alkaloid profile by the product of easH. The same ergot alkaloid profile was observed in a previous study in which *C. purpurea* easA was expressed in *A. fumigatus* easA ko (15). Strains that expressed the *E.* sp. Lp1 easA/cloA construct also accumulated chanoclavine, agroclavine, and setoclavine/isosetoclavine but at levels comparable to the parent strain *A. fumigatus* easA ko. In addition, the easA/cloA expressing strains accumulated a pair of polar compounds that co-eluted with lysergic acid/isolysergic acid standards (FIG. 4). The identity of the compounds as lysergic acid and its diastereoisomer was supported by LC-MS analyses in which the easA/cloA strains produced parent ions and fragments identical to those arising from the lysergic acid standard. These data indicate that CloA catalyzes a cumulative six electron oxidation of agroclavine to lysergic acid and that CloA or EasA isomerizes the 8,9 double bond in the D ring to the 9,10 position. Expression of constructs in which easA from *E.* sp. Lp1 was replaced by easA from *Claviceps fusiformis* [a species whose pathway ends at elymoclavine and thus never isomerizes an 8,9 double bond to a 9,10 double bond (21)], still resulted in production of lysergic acid. This observation supports the hypothesis that double bond isomerase activity resides on CloA rather than EasA. The amount of lysergic acid extracted from easA/cloA cultures varied depending on the solvent used. Both 98% methanol+2% acetic acid and 10% (w/v) aqueous ammonium carbonate extracted significantly more (approximately 2.5 fold) lysergic acid than did unsupplemented methanol (P=0.006).

In addition to known ergot alkaloids described above, strains transformed with constructs containing either easA/easH or easA/cloA fragments accumulated two novel alkaloids referred to as unknown A (unk A) and unknown B (unk B) (FIG. 4; Table 1). The easA/easH strain, which accumulated significantly more agroclavine and setoclavine than did the easA/cloA strain, also accumulated significantly greater quantities of unk A and B. Unk A fluoresced more intensely at the 272/372 nm wavelength settings than at the 310/410 nm wavelength settings, which is typical of ergot alkaloids lacking a double bond between positions 9 and 10 of the ergoline nucleus (12). In contrast unk B fluoresced ten times more intensely at 310/410 nm wavelengths than at the 272/372 nm wavelength setting, indicating the presence of a 9,10 double bond (12). LC-MS analyses revealed that unk A and B had molecular ions with masses of 307.3 and 323.2, respectively (FIG. 5). The molecular ion of unk A corresponds to the mass of [agroclavine+H]$^+$ with an additional prenyl group, whereas, the molecular ion of unk B corresponds to the mass of [setoclavine+H]$^+$ with an additional prenyl group.

To test the hypothesis that unk A and B correspond to prenylated version of agroclavine and setoclavine, agroclavine was fed to three isolates of *A. fumigatus*: 1) easA ko, the transformation recipient, which was derived from *A. fumigatus* isolate FGSC A1141 and contains a functional copy of the ergot alkaloid prenyl transferase gene easL (27); 2) Af 293, a wild-type strain that also has a functional copy of easL (27); and, 3) NRRL 164, a strain unable to produce the prenylated ergot alkaloid fumigaclavine C due to a mutation resulting in a premature stop codon in easL (27). Agroclavine-fed cultures of all isolates contained some unmetabolized agroclavine and its oxidation product setoclavine. However, only easA ko and Af 293, which contain functional copies of the prenyl transferase gene easL, accumulated unk A and unk B (Table 2). These data are consistent with unk A and B being agroclavine and setoclavine, respectively, prenylated by the prenyl transferase encoded by easL.

Our results demonstrate that the P450 monooxygenase encoded by cloA of *E.* sp. Lp1 catalyzes successive oxidations of agroclavine to produce lysergic acid. The data also suggest that CloA catalyzes the double bond isomerization, from position 8,9 to 9,10. Our strategy for testing the function of the genes easH and cloA through heterologous expression in an *A. fumigatus* background that was modified simultaneously to produce the substrate agroclavine was effective. Consistent with the data of Coyle et al. (15), both easA/easH and easA/cloA mutants produced agroclavine, as a result of expressing *E.* sp. Lp1 easA. In addition, both types of transformants accumulated setoclavine and isosetoclavine, diastereoisomers formed by the oxidation of agroclavine by endogenous peroxidases in *A. fumigatus* and dozens of other fungi and plants (15, 28, 29). However, only transformants containing the easA/cloA construct yielded lysergic acid. The lesser quantities of agroclavine and setoclavine observed in the easA/cloA transformants, compared to the easA/easH strains, are consistent with the easA/cloA strains having CloA to oxidize accumulating agroclavine. The accumulation of lysergic acid in CloA-expressing strains indicates that the enzyme performs multiple catalytic steps: a two electron oxidation of agroclavine to elymoclavine, then a pair of two electron oxidations to convert elymoclavine to lysergic acid, presumably via an undetected aldehyde intermediate (30). The role of CloA in catalyzing multiple oxidations to form paspalic acid or lysergic acid was previously hypothesized by Haarmann et al. (26). Our data also indicate that CloA catalyzes the double bond isomerization. Although a role for *E.* sp. Lp1 EasA (introduced on the same construct) in the double bond isomerization cannot be excluded, the observation that an easA/cloA construct containing easA from *C. fusiformis* (lacking lysergic acid and thus the need to isomerize the double bond in ring D) still produced lysergic acid, indicates that the double bond isomerase activity resides on CloA.

The lack of detectable elymoclavine—the first oxidation product of cloA acting on agroclavine—or any other intermediates in the oxidation series to lysergic acid in our positive transformants indicates that CloA may bind agroclavine and execute successive oxidations before releasing lysergic acid. The lack of detectable paspalic acid (which is the 8,9-double bond isomer of lysergic acid) in our lysergic acid-positive transformants indicates that the double bond isomerization, from position 8,9 (as in agroclavine and elymoclavine) to position 9,10 (as in lysergic acid and derivatives thereof), occurs while substrate is bound to CloA. Moreover, young cultures (<3 days old) yielded lesser quantities of lysergic acid when extracted with methanol but significantly more when extracted with acetic acid-supplemented methanol or ammonium carbonate. One interpretation of this observation is that the acid or base helped denature CloA, releasing otherwise bound product for detection.

An unexpected and important finding of this study was the accumulation of two novel alkaloids, unk A and B, from both mutants but in greater quantities in the easA/easH transformants, which accumulated greater concentrations of agroclavine and setoclavine. The structure of each unknown, with a prenyl group on carbon 2 of either agroclavine or setoclavine, comes from three observations. First, the elution time and fluorescence properties of each analyte were consistent with predicted properties of prenylated forms of agroclavine and setoclavine. Second, the molecular weights are consistent with either agroclavine or setoclavine, with a 68 amu moiety attached, which corresponds to the mass of a prenyl group. Finally, and most importantly, the accumulation of the compounds was restricted to strains of *A. fumigatus* that have a functional copy of the prenyl transferase FgaPT1 (encoded by the ergot alkaloid cluster gene easL). FgaPT1 is responsible for prenylating fumigaclavine A to fumigaclavine C (31), and the discovery of 2-prenylated versions of additional ergot alkaloids, such as 2-prenylated festuclavine and 2-prenylated fumigaclavine B (32), indicates that FgaPT1 accepts other ergot alkaloids as substrates. The easA ko mutant that served as the recipient in our transformations was derived from *A. fumigatus* FGSC A1141, which accumulates fumigaclavine C (27), demonstrating that it has a functional copy of easL. Our data demonstrates that a combinatorial approach based on expression of enzymes from a different lineage of ergot alkaloid producers in *A. fumigatus* can yield novel ergot alkaloids. Based on their structures, it is possible that unk A and unk B will have activities similar to those of fumigaclavine C, which has been shown to have anti-inflammatory activity (33).

In summation, our method of the present invention of heterologous expression of easA (to produce agroclavine substrate) along with candidate oxidase genes easH or cloA successfully demonstrated that cloA is necessary for lysergic acid production from agroclavine. The production of lysergic acid in an experimentally tractable and fast-growing organism such as *A. fumigatus* is significant because lysergic acid is used as a base for modification in numerous pharmaceutical products, including the drugs nicergoline, cabergoline, and metergoline (34). Currently, lysergic acid is mass produced by hydrolysis of more complex ergot alkaloids or isomerization of paspalic acid obtained from two-stage fermentation cultures or from ergots obtained from inoculated plants (34). In contrast, our easA/cloA mutant produces lysergic acid directly. In addition, *A. fumigatus* has the potential to be a better industrial fungus in terms of growth rate and ease of genetic manipulation. Therefore, the easA/cloA mutant of this invention is of industrial use in providing a more direct means of producing lysergic acid or derivatives thereof.

Methods and Materials

Preparation of Transformation Constructs.

Each candidate oxidase gene (easH or cloA) was incorporated into a three-component construct that contained a bidirectional promoter from *A. fumigatus* (originating from the divergently transcribed genes easA and easG) centered between the candidate oxidase gene from *E.* sp. Lp1 and the allele of easA from *E.* sp. Lp1 (FIG. 2). The bidirectional promoter drove expression of both the candidate oxidase gene and *E.* sp. Lp1 easA. The easA allele was included to generate agroclavine as substrate for the product of the candidate gene. Constructs were generated by fusion PCRs.

Fungal Transformation.

Candidate oxidase constructs were co-transformed into *A. fumigatus* easA ko (15), along with the selectable marker pAMD1, which contains the acetamidase gene of *Aspergillus nidulans* (35). Transformants capable of utilizing acetamide as a source of nitrogen were selected on acetamide medium (36). The transformation protocol was based on previously described methods (15, 18).

mRNA Analysis.

Cultures were grown in 50 mL of malt extract broth (Difco, Detroit, Mich.) in a 250 mL flask for 1 day while shaking at 80 rpm at 37° C. to form a mat of hyphae on the surface of the broth. The mat was transferred to an empty Petri dish and incubated at 37° C. for an additional day to promote conidiation. RNA was extracted from approximately 100 mg of conidiating colony with the Plant RNeasy kit (Qiagen, Gaithersburg, Md.), treated with DNaseI (Qiagen), and reverse transcribed with Superscript II (Invitrogen, Carlsbad, Calif.). The presence of transcripts from individual genes was tested by PCR with gene-specific primers The absence of genomic DNA in individual cDNA preps was confirmed by priming amplification with oligonucleotides that flank an intron.

Alkaloid Analysis.

For quantitative analyses, colonies were grown on malt extract agar [15 g malt extract+15 g agar per L] for 11 days. Samples of approximately 50 mm$^2$ surface area were collected with the broad end of a 1000-µL pipet tip. Unless otherwise indicated, alkaloids were extracted with 98% methanol+2% acetic acid at 55° C. for 30 min. Alternate extractions were conducted with 100% methanol or 10% aqueous ammonium acetate. Conidia in each extract were counted to provide an estimate of fungal biomass. Extracts clarified by centrifugation were then analyzed by reverse-phase HPLC with fluorescence detection (12). Lysergic acid standard was prepared by hydrolyzing 1 mg of ergotamine tartrate (Sigma-Aldrich, St. Louis, Mo.) in 100 µL of 1.2 M NaOH at 75° C. for 6 hr, followed by neutralization with a 1.2 M solution of HCl, purification on a C18 SPE column (Biotage, Charlotte, N.C.), and verification by LC-MS. Chanoclavine was obtained from Alfarma (Prague, Czech Republic), agroclavine was obtained from Fisher (Pittsburgh, Pa.), and setoclavine was prepared by oxidizing agroclavine as previously described (28, 29). Quantities of alkaloids among strains were compared by ANOVA and, when ANOVA indicated a significant effect of fungal strain on alkaloid quantity (P<0.05), means were separated by a Tukey-Kramer test. Statistical analyses were performed with JMP (SAS, Cary, N.C.). For LC-MS analysis, cultures were grown for 1 week on malt extract agar. Conidiating cultures were washed repeatedly with 4 mL of HPLC-grade methanol. After pelleting conidia and mycelia by centrifugation, the supernatant was concentrated to 100 µL in a speedvac, and 10 µL was analyzed by LC-MS as described previously (37).

Precursor Feeding Study.

The ability of strains of *A. fumigatus* to convert agroclavine or setoclavine into unk A or B was tested by feeding agroclavine to the following *A. fumigatus* strains: NRRL 164, which lacks a functional copy of easL, and easA ko and Af 293, which have functional copies of easL (27). Six replicate cultures of each strain were grown from 60,000 conidia in 200 µL of malt extract broth in a 2-mL microcentrifuge tube. Cultures were supplemented with 37 nmol of agroclavine in 1 µL of methanol or with 1 µL methanol as a control. An additional control was malt extract broth without conidia but with 1 µL of agroclavine (37 nmol). The cultures were incubated for 1 week at 37° C. and then extracted by the addition of 300 µL of methanol along with ten 3-mm diameter glass beads followed by bead-beating in a Fastprep 120 (Bio101, Carlsbad, Calif.) at 6 m/s for 30 s. Alkaloids were analyzed by HPLC with fluorescence detection as described above.

The above research with lysergic acid was conducted with licenses from the West Virginia Board of Pharmacy (T10555042) and the US Drug Enforcement Agency (RP0463353).

REFERENCES NOTED HEREIN

1. Matossian M K (1989) Poisons of the past: molds, epidemics, and history. Yale University Press, New Haven.
2. Leuchtmann A, Bacon C W, Schardl C L, White J F, Tadych M (2014) Nomenclatural realignment of *Neotyphodium* species with genus *Epichloë*. *Mycologia* 106: (in press).
3. Schardl C L, Young C A, Faulkner J R, Florea S, Pan, J (2012) Chemotypic diversity of epichloae, fungal symbionts of grasses. *Fungal Ecol* 5(3):331-344.
4. Panaccione D G, Beaulieu W T, Cook D (2014) Bioactive alkaloids in vertically transmitted fungal endophytes. *Funct Ecology* 28(2):299-314.
5. Baskys A, Hou A C (2007) Vascular dementia: pharmacological treatment approaches and perspectives. *Clin Interv Aging* 2(3):327-335.
6. Morren J A, Galvez-Jimenez N (2010) Where is dihydro-ergotamine mesylate in the changing landscape of migraine therapy? *Expert Opin Pharmacother* 11(18): 3085-3093.
7. Perez-Lloret S, Rascol O (2010). Dopamine receptor agonists for the treatment of early or advanced Parkinson's disease. *CNS Drugs* 24(11):941-968.
8. Hofmann A (1980) LSD—my problem child. McGraw-Hill, New York.
9. Schardl C L, Leuchtmann A, Tsai H F, Collett M A, Watt D M, Scott D B (1994) Origin of a fungal symbiont of perennial ryegrass by interspecific hybridization of a mutualist with the ryegrass choke pathogen, *Epichloë typhina*. *Genetics* 136(4):1307-1317.
10. Schardl C, Panaccione D G, Tudzynski P (2006) Ergot alkaloids—biology and molecular biology. *Alkaloids Chem Biol* 63(2006):45-86.
11. Lorenz N, Haarmann T, Pazoutov S, Jung M, Tudzynski P (2009) The ergot alkaloid gene cluster: functional analyses and evolutionary aspects. *Phytochemistry* 70(15):1822-1832.
12. Panaccione D G, Ryan K L, Schardl C L, Florea S (2012) Analysis and modification of ergot alkaloid profiles in fungi. *Methods Enzymol* 515:267-290.
13. Wallwey C, Li S-M (2011) Ergot alkaloids: structure diversity, biosynthetic gene clusters and functional proof of biosynthetic genes. *Nat Prod Rep* 28(3):496-510.
14. Cheng J Z, Coyle C M, Panaccione D G, O'Connor S E (2010) A role for old yellow enzyme in ergot alkaloid biosynthesis. *J Am Chem Soc* 132(6):1776-1777.
15. Coyle C M, Cheng J Z, O'Connor S E. Panaccione D G (2010) An old yellow enzyme gene controls the branch point between *Aspergillus fumigatus* and *Claviceps purpurea* ergot alkaloid pathways. *Appl Environ Microbiol* 76(12):3898-3903.
16. Wallwey C, Matuschek M, Li S-M (2010) Ergot alkaloid biosynthesis in *Aspergillus fumigatus*: Conversion of chanoclavine-I to chanoclavine-I aldehyde catalyzed by a shortchain alcohol dehydrogenase FgaDH. *Arch Microbiol* 192(2):127-134.
17. Cheng J Z, Coyle C M, Panaccione D G, O'Connor S E (2010) Controlling a structural branch point in ergot alkaloid biosynthesis. *J Am Chem Soc* 132(37):12835-12837.
18. Coyle C M, Panaccione D G (2005) An ergot alkaloid biosynthesis gene and clustered hypothetical genes from *Aspergillus fumigatus*. *Appl Environ Microbiol* 71(6): 3112-3118.
19. Haarmann T, et al (2005) The ergot alkaloid gene cluster in *Claviceps purpurea*: extension of the cluster sequence and intra species evolution. *Phytochemistry* 66(11):1312-1320.
20. Fleetwood D J, Scott B, Lane G A, Tanaka A, Johnson R D (2007) A complex ergovaline gene cluster in *Epichloë* endophytes of grasses. *Appl Environ Microbiol* 73(8): 2571-2579.
21. Lorenz N, Wilson E V, Machado C, Schardl C L, Tudzynski P (2007) Comparison of ergot alkaloid biosynthesis gene clusters in *Claviceps* species indicates loss of late pathway steps in evolution of *C. fusiformis*. *Appl Environ Microbiol* 73(22):7185-7191.
22. Unsöld I A, Li S. M (2005) Overproduction, purification and characterization of FgaPT2, a dimethylallyltryptophan synthase from *Aspergillus fumigatus*. *Microbiology* 151(5):1499-1505.
23. Schardl C L, et al (2013a) Plant-symbiotic fungi as chemical engineers: multi-genome analysis of the Clavicipitaceae reveals dynamics of alkaloid loci. *PLoS Genet* 9(2):e1003323.
24. Schardl C L, et al (2013b) Currencies of mutualisms: Sources of alkaloid genes in vertically transmitted epichloae. *Toxins* 5(6):1064-1088.
25. Havemann J, Vogel D, Loll B, Keller U (2014) Cyclolization of D-lysergic acid alkaloid peptides. *Chem Biol* 21(1):146-155.
26. Haarmann T, Ortel I, Tudzynski P, Keller U (2006) Identification of the cytochrome P450 monooxygenase that bridges the clavine and ergoline alkaloid pathways. *Chembiochem* 7(4):645-652.
27. Robinson S L, Panaccione D G (2012) Chemotypic and genotypic diversity in the ergot alkaloid pathway of *Aspergillus fumigatus*. *Mycologia* 104(4):804-812.
28. Béliveau J, Ramstad E (1967) 8-Hydroxylation of agroclavine and elymoclavine by fungi. *Llyodia* 29(3):234-238.
29. Panaccione D G, Tapper B A, Lane G A, Davies E, Fraser K (2003) Biochemical outcome of blocking the ergot alkaloid pathway of a grass endophyte. *J Agric Food Chem* 51(22):6429-6437.
30. Lin C L, et al. (1973) Biosynthesis of ergot alkaloids: Synthesis of 6-methyl-8-acetoxymethylene-9-ergolene and its incorporation into ergotoxine by *Claviceps*. *J Org Chem* 38(12):2249-2251.
31. Unsöld I A, Li S-M (2006) Reverse prenyltransferase in the biosynthesis of fumigaclavine C in *Aspergillus fumigatus*: gene expression, purification, and characterization of fumigaclavine C synthase FgaPT1. *Chembiochem* 7(1):158-164.
32. Ge H M, Yu Z G, Zhang J, Wu J H, Tan R X (2009) Bioactive alkaloids from endophytic *Aspergillus fumigatus*. *J Nat Prod* 72(4):753-755.
33. Du R H, Li E G, Cao Y, Song Y C, Tan R X (2011) Fumigaclavine C inhibits tumor necrosis factor α production via suppression of toll-like receptor 4 and nuclear factor κB activation in macrophages. *Life Sci* 89(7):235-240.
34. Cvak L (1999) in Ergot: The Genus *Claviceps*. eds Kren V, Cvak L (Harwood, Amsterdam), pp 373-409.
35. Hynes M J, Corrick C M, King J A (1983) Isolation of genomic clones containing the amdS gene of *Aspergillus* nidulans and their use in the analysis of structural and regulatory mutations. *Mol Cell Biol* 3(8):1430-1439.
36. Panaccione D G, Scott-Craig J S, Pocard J A, Walton J D (1992) A cyclic peptide synthetase gene required for pathogenicity of the fungus *Cochliobolus carbonum* on maize. *Proc Natl Acad Sci USA* 89(14):6590-6594.
37. Ryan K L, Moore C T, Panaccione D G (2013) Partial reconstruction of the ergot alkaloid pathway by heterologous gene expression in *Aspergillus nidulans*. *Toxins* 5(2):445-455.
Robinson, S. L., and Panaccione, D. G. 2014. Heterologous expression of lysergic acid and novel ergot alkaloids in *Aspergillus fumigatus*. Applied and Environmental Microbiology 80:6465-6472.
Agurell S, Ramstad E. 1965. A new ergot alkaloid from Mexican maize ergot. *Acta Pharm Suecica* 2:231-238.
Barrow K D, Mantle P G, Quigley F R. 1974. Biosynthesis of dihydroergot alkaloids. *Tet Lett* 16:1557-1560.
Baskys A, Hou A C. 2007. Vascular dementia: pharmacological treatment approaches and perspectives. *Clin Interv Aging* 2:327-335.
Béliveau J, Ramstad E. 1967. 8-Hydroxylation of agroclavine and elymoclavine by fungi. *Llyodia* 29:234-238.
Cheng J Z, Coyle C M, Panaccione D G, O'Connor S E. 2010a. A role for old yellow enzyme in ergot alkaloid biosynthesis. *J Amer Chem Soc* 132:1776-1777.
Cheng J Z, Coyle C M, Panaccione D G, O'Connor S E. 2010b. Controlling a structural branch point in ergot alkaloid biosynthesis. *J Amer Chem Soc* 132:12835-12837.
Coyle C M, Panaccione D G. 2005. An ergot alkaloid biosynthesis gene and clustered hypothetical genes from *Aspergillus fumigatus*. *Appl Environ Microbiol* 71:3112-3118.
Coyle C M, Cheng J Z, O'Connor S E, Panaccione D G. 2010. An old yellow enzyme gene controls the branch point between *Aspergillus fumigatus* and *Claviceps purpurea* ergot alkaloid pathways. *Appl Environ Microbiol* 76:3898-3903.
Gao, Q., Jin, K., Ying, S-H., Qiang, Zhang Y, Xiao G, Shang Y, Duan Z, Hu X, Xie X-Q, Zhou G, Peng G, Luo Z, Huang W, Wang B, Fang W, Wang 5, Zhong Y, Ma L-J, St. Leger R J, Zhao G-P, Pei Y, Feng M-G, Xia Y, Wang C. 2011. Genome sequencing and comparative transcriptomics of the model entomopathogenic fungi *Metarhizium anisopliae* and *M. acridum*. *PLoS Genet* 7:e1001264.
Goetz K E, Coyle C M, Cheng J Z, O'Connor S E, Panaccione D G. 2011. Ergot cluster-encoded catalase is required for synthesis of chanoclavine-I in *Aspergillus fumigatus*. *Curr Genet* 57:201-211.
Gröger, D., & Floss, H. G. 1997. Biochemistry of ergot alkaloids-achievements and challenges. *Alkaloids: Chem Biol* 50:171-218.
Haarmann T, Ortel I, Tudzynski P, Keller U. 2006. Identification of the cytochrome P450 monooxygenase that bridges the clavine and ergoline alkaloid pathways. *Chembiochem* 7:645-652.
Hofmann A. 1980. LSD—my problem child. McGraw-Hill, New York.
Hynes M J, Corrick C M, King J A. 1983. Isolation of genomic clones containing the amdS gene of *Aspergillus nidulans* and their use in the analysis of structural and regulatory mutations. *Mol Cell Biol* 3:1430-1439.
Langfelder, K., Jahn, B., Gehringer, H., Schmidt, A., Wanner, G., & Brakhage, A. A. 1998. Identification of a polyketide synthase gene (pksP) of *Aspergillus fumigatus* involved in conidial pigment biosynthesis and virulence. *Med Microbiol Immunol* 187:79-89.
Leuchtmann A, Bacon C W, Schardl C L, White J F, Tadych M. 2014. Nomenclatural realignment of *Neotyphodium* species with genus *Epichloë*. *Mycologia* 106: (in press) doi:10.3852/14-060.
Liu, Y. G., Chen, Y. 2007. High-efficiency thermal asymmetric interlaced PCR for amplification of unknown flanking sequences. *BioTechniques* 43:649-656.
Liu Y G, Chen Y, Zhang Q. 2005. Amplification of genomic sequences flanking T-DNA insertions by thermal asymmetric interlaced polymerase chain reaction. *Methods Mol Biol* 286:341-348.
Lorenz N, Haarmann T, Pazoutova S, Jung M, Tudzynski P. 2009. The ergot alkaloid gene cluster: functional analyses and evolutionary aspects. *Phytochemistry* 70:1822-1832.
Maier, W., Schumann, B., & Gröger, D. 1988. Microsomal oxygenases involved in ergoline alkaloid biosynthesis of various *Claviceps* strains. *J Basic Microbiol* 28:83-93.
Matossian M K. 1989. Poisons of the past: molds, epidemics, and history. Yale University Press, New Haven.
Matuschek M, Wallwey C, Xie X, Li S M. 2011. New insights into ergot alkaloid biosynthesis in *Claviceps purpurea*: an agroclavine synthase EasG catalyses, via a non-enzymatic adduct with reduced glutathione, the conversion of chanoclavine-I aldehyde to agroclavine. *Org Biomol Chem* 9:4328-4335.
Morren J A, Galvez-Jimenez N. 2010. Where is dihydroergotamine mesylate in the changing landscape of migraine therapy? *Expert Opin Pharmacother* 11:3085-3093.
Panaccione D G, Coyle C M. 2005. Abundant respirable ergot alkaloids from the common airborne fungus *Aspergillus fumigatus*. *Appl Environ Microbiol* 71:3106-3111.
Panaccione, D. G., Tapper, B. A., Lane, G. A., Davies, E., and Fraser, K. 2003. Biochemical outcome of blocking the ergot alkaloid pathway of a grass endophyte. *J Agric Food Chem* 51:6429-6437.
Panaccione D G, Cipoletti J R, Sedlock A B, Blemings K P, Schardl C L, Machado C, Seidel G E. 2006. Effects of ergot alkaloids on food preference and satiety in rabbits, as assessed with gene knockout endophytes in perennial ryegrass (*Lolium perenne*). *J Agric Food Chem* 54:4582-4587.
Panaccione D G, Ryan K L, Schardl C L, Florea S. 2012. Analysis and modification of ergot alkaloid profiles in fungi. *Methods Enzymol* 515:267-290.
Panaccione D G, Beaulieu W T, Cook D. 2014. Bioactive alkaloids in vertically transmitted fungal endophytes. *Funct Ecol* 27:299-314.
Panaccione D G. 2005. Origins and significance of ergot alkaloid diversity in fungi. *FEMS Microbiol Lett* 251:9-17.
Pažutová S. 2001. The phylogeny and evolution of the genus *Claviceps*. *Mycol Res* 105:275-283.
Perez-Lloret S, Rascol O. 2010. Dopamine receptor agonists for the treatment of early or advanced Parkinson's disease. *CNS Drugs* 24:941-968.
Riederer B, Han M, Keller U. 1996. D-Lysergyl peptide synthetase from the ergot fungus *Claviceps purpurea*. *J Biol Chem* 271:27524-27530.
Robinson S L, Panaccione D G. 2012. Chemotypic and genotypic diversity in the ergot alkaloid pathway of *Aspergillus fumigatus*. *Mycologia* 104:804-812.
Robinson, S. L., and Panaccione, D. G. 2014. Heterologous expression of lysergic acid and novel ergot alkaloids in *Aspergillus fumigatus*. Applied and Environmental Microbiology 80:6465-6472.

Rutschmann J, Kobel H, Schreier E. 1967. Heterocyclic carboxylic acids and their production. U.S. Pat. No. 3,314,961.

Ryan K L, Moore C T, Panaccione D G. 2013. Partial reconstruction of the ergot alkaloid pathway by heterologous gene expression in *Aspergillus nidulans*. *Toxins* 5:445-455.

Schardl C L, Leuchtmann A, Tsai H F, Collett M A, Watt D M, Scott D B. 1994. Origin of a fungal symbiont of perennial ryegrass by interspecific hybridization of a mutualist with the ryegrass choke pathogen, *Epichloë typhina*. *Genetics* 136:1307-1317.

Schardl C L, Panaccione D G, Tudzynski P. 2006. Ergot alkaloids—biology and molecular biology. *Alkaloids: Chem Biol* 62:45-86.

Schardl C L, Young C A, Faulkner J R, Florea S, Pan, J. 2012. Chemotypic diversity of epichloae, fungal symbionts of grasses. *Fungal Ecol* 5:331-344.

Schardl C L, Young C A, Hesse U, Amyotte S G, Andreeva K, Calie P J, Fleetwood D J, Haws D C, Moore N, Oeser B, Panaccione D G, Schweri K K, Voisey C R, Farman M L, Jaromczyk J W, Roe B A, O'Sullivan D M, Scott B, Tudzynski P, An Z, Arnaoudova E G, Bullock C T, Charlton N D, Chen L, Cox M, Dinkins R D, Florea S, Glenn A E, Gordon A, Güldener U, Harris D R, Hollin W, Jaromczyk J, Johnson R D, Khan A K, Leistner E, Leuchtmann A, Li C, Liu J G, Liu J, Liu M, Mace W, Machado C, Nagabhyru P, Pan J, Schmid J, Sugawara K, Steiner U, Takach J E, Tanaka E, Webb J S, Wilson E V, Wiseman J L, Yoshida R, Zeng Z. 2013a. Plant-symbiotic fungi as chemical engineers: multi-genome analysis of the Clavicipitaceae reveals dynamics of alkaloid loci. *PLoS Genet* 9:e1003323.

Schardl C L, Young C A, Pan J, Florea S, Takach J E. Panaccione D G, Farman M L, Webb J S, Jaromczyk J, Charlton N D, Nagabhyru P, Chen L, Shi C, Leuchtmann A. 2013b. Currencies of mutualisms: Sources of alkaloid genes in vertically transmitted epichloae. *Toxins* 5:1064-1088.

Scigelova M, Macek T, Minghetti A, Mackova M, Sedmera P, Prikrylova V, Kren V. 1995. Biotransformation of ergot alkaloids by plant cell cultures with high peroxidase activity. *Biotechnol Lett* 17:1213-1218.

Singer T, Burke E. 2003. High-throughput TAIL-PCR as a tool to identify DNA flanking insertions. *Method Mol Biol* 236:241-72.

Tooley P W, Bandyopadhyay R, Carras M M, Pažutová S. 2006. Analysis of *Claviceps africana* and *C. sorghi* from India using AFLPs, EF-1α gene intron 4, and β-tubulin gene intron 3. *Mycol Res* 110:441-451.

Tsai H-F, Chang Y C, Washburn R G, Wheeler M H, Kwon-Chung K J. 1998. The developmentally regulated alb1 gene of *Aspergillus fumigatus*: its role in modulation of conidial morphology and virulence. *J Bacteriol* 180:3031-3038.

Unsöld I A, Li S-M. 2005. Overproduction, purification and characterization of FgaPT2, a dimethylallyltryptophan synthase from *Aspergillus fumigatus*. *Microbiology* 151:1499-1505.

Wallwey C, Li S-M. 2011. Ergot alkaloids: structure diversity, biosynthetic gene clusters and functional proof of biosynthetic genes. *Nat Prod Rep* 28:496-510.

Wallwey C, Matuschek M, Xie X-L, Li S-M. 2010b. Ergot alkaloid biosynthesis in *Aspergillus fumigatus*: conversion of chanoclavine-I aldehyde to festuclavine by the festuclavine synthase FgaFS in the presence of the old yellow enzyme FgaOx3. *Org Biomol Chem* 8:3500-3508.

Winblad, B., Fioravanti, M., Dolezal, T., Logina, I., Milanov, I. G., Popescu, D. C., & Solomon, A. 2008. Therapeutic use of nicergoline. *Clin Drug Investig* 28:533-552.

FIGS. 1-5 and 9-14 Legends

FIG. 1 shows intermediates and products of the ergot alkaloid pathway (as composited from branches found in different fungi). The role of different alleles of easA (isomerase versus reductase encoding types) in controlling the branch point is indicated. Alkaloids with a 9,10 double bond (e.g., setoclavine and lysergic acid and its derivatives) often occur as diastereoisomers at position 8). Roles for genes discussed in text or illustrated in FIG. 2 are indicated. Double arrows indicate one or more omitted intermediates. Insert shows ring and position labeling referred to in text. DMAPP, dimethylallylpyrophosphate.

FIG. 2 shows ergot alkaloid synthesis (eas) clusters from *E*. sp. Lp1 (FIG. 2A) and *Aspergillus fumigatus* (FIG. 2B), and design of transformation construct (FIG. 2C). FIG. 2A shows *Epichloë* sp. Lp1 eas cluster redrawn from Schardl et al. (2013b); AT rich repeat regions (15 to 25 kb each) were compressed in the diagram to facilitate the presentation. FIG. 2B. shows *Aspergillus fumigatus* eas cluster redrawn from Coyle and Panaccione (2005); P=pseudogene. Genes unique to the *E*. sp. Lp1 cluster are shown in black, and those unique to the *A. fumigatus* cluster are indicated in white. Genes common to both clusters are shown in gray. Although both clusters contain an allele of easA, the products of those alleles differ functionally, and so they differ in shading in their respective clusters. FIG. 2C shows general design of constructs generated by fusion PCR. Candidate genes were cloA or easH from *E*. sp. Lp1. Black and white fragments correspond to *E*. sp. Lp1 or *A. fumigatus* origin, as above.

FIG. 3 shows a qualitative RT-PCR demonstrating accumulation of mRNA from indicated genes in *A. fumigatus* easA ko transformants. Horizontal strain labels: easA ko refers to non-transformed recipient stain; and, easA/cloA or easA/easH refer to transformants. Vertical gene labels refer to the *E*. sp. Lp1 gene for which amplification was attempted in that lane. Each cDNA preparation was diluted 1:1000 prior to amplification. Scale at left indicates the relative mobility of relevant fragments from BstEII-digested bacteriophage lambda.

FIG. 4 shows an analysis of ergot alkaloids from transformed strains of *A. fumigatus*. Samples were analyzed with two fluorescence detectors; excitation and emission wavelengths are indicated. Lysergic acid and other ergot alkaloids with a 9,10 double bond fluoresce more strongly at 310 nm/410 nm conditions, whereas other ergot alkaloids fluoresce maximally with settings of 272 nm/372 nm (Panaccione et al., 2012). Ergot alkaloids with 9,10 double bonds form diastereoisomers at carbon 8. Values for both diastereoisomers were added in quantitative analyses. Strain names and line colors are indicated in key. Abbreviations: LA, lysergic acid; ILA, isolysergic acid; IS, isosetoclavine; 5, setoclavine; UB, unknown B, Ch, chanoclavine; Ag, agroclavine; UA, unknown A.

FIG. 5 shows mass spectra of two unknown alkaloids with hypothesized structures. Spectra were collected from LC-MS analyses with electrospray ionization in positive mode. Further evidence of prenylation is presented in Table 2.

FIG. 9 shows the analysis of ergot alkaloids from transformed strains of *A. fumigatus*. Samples were analyzed with two fluorescence detectors; excitation and emission wavelengths are indicated. Lysergic acid and other ergot alkaloids with a 9, 10 double bond fluoresce more strongly at 310 nm/410 nm conditions, whereas other ergot alkaloids fluoresce maximally with settings of 272 nm/372 nm (Panaccione et al., 2012). In protic solvents, lysergic acid forms diastereoisomers (with isolysergic acid) at C8. Values for both diastereoisomers were added in quantitative analyses. Strain names and line colors are indicated in key. Abbreviations: LA, lysergic acid; ILA, isolysergic acid; S, setoclavine; Ch, chanoclavine; Ag, agroclavine.

FIG. 10 shows alternate origins of agroclavine and origin of setoclavine. Pathway spurs leading to setoclavine are indicated in green. When easA is knocked out, chanoclavine aldehyde that accumulates can keto-enol tautomerize. Tautomers that resolve with the aldehyde in close proximity to the secondary amine can undergo ring closure via Schiff base formation. The resulting iminium ion (FIG. 6) is reduced by EasG to form agroclavine (Coyle et al., 2010). Agroclavine that accumulates can be oxidized at C8 to form setoclavine by non-specific peroxidase activity present in many organisms (e.g., Béliveau and Ramstad, 1967; Panaccione et al., 2003; Coyle et al., 2010).

Figure 14:
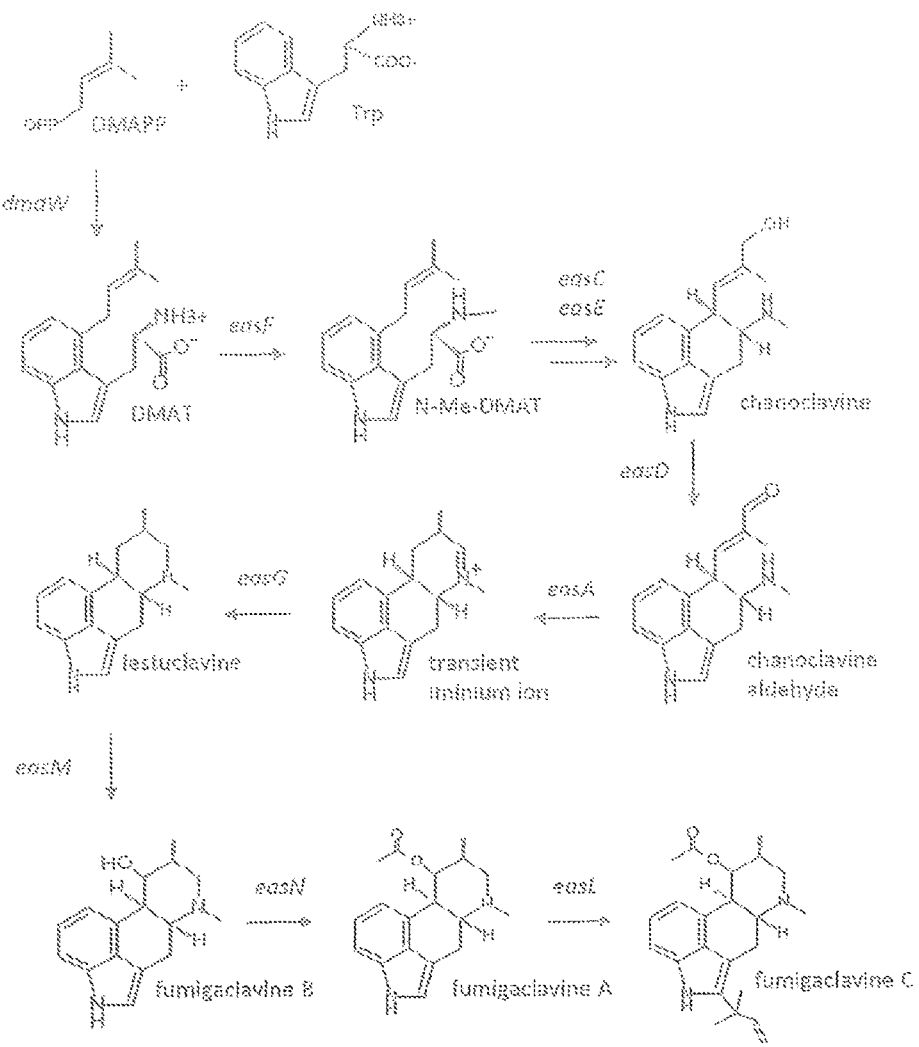

FIG. 14 shows ergot alkaloid pathway of *Aspergillus fumigatus*. Roles for genes are indicated between intermediates or products. Double arrow indicates one or more ncharacterized intermediates: DMAPP, dimethylallylpyrophosphate; DMAT, dimethylallyltryptophan; Trp, tryptophan.

TABLE 2

Ergot alkaloids (nmol per culture) in strains fed 37 nmol agroclavine and controls [a]

| strain/treatment | agro-clavine | seto-clavine [b] | unknown A | unknown B |
|---|---|---|---|---|
| Af 293/agroclavine | 22 ± 1 B | 2.5 ± 0.1 A | 0.56 ± 0.04 A | 0.040 ± 0.001 A |
| NRRL 164/agroclavine | 24 ± 2 B | 2.1 ± 0.2 AB | n.d. | n.d. |
| easA ko/agroclavine | 21 ± 0.3 B | 1.9 ± 0.08 B | 0.22 ± 0.03 B | 0.0078 ± 0.0007 B |
| medium/agroclavine | 31 ± 0.5 A | 0.89 ± 0.05 C | n.d. | n.d. |
| Af 293/methanol | n.d. | n.d. | n.d. | n.d. |
| NRRL 164/methanol | n.d. | n.d. | n.d. | n.d. |
| easA ko/methanol | 0.041 ± 0.002 C | 0.0023 ± 0.0003 D | n.d. | n.d. |

[a] Data are means of six samples ± standard error; means followed by a different letter within a column differ significantly ($\alpha = 0.05$) in a Tukey-Kramer test.
[b] Values calculated from sums of both diastereoisomers.

Specific Embodiments of this Invention

We combined genes from ergot alkaloid pathways from two fungal lineages to produce lysergic acid in the genetically tractable fungus *Aspergillus fumigatus*. In doing so, we demonstrated that a previously identified gene encodes additional activities required for lysergic acid biosynthesis. This unique expression platform will allow for testing of the functions of additional alleles of these key genes in the pathway to lysergic acid. Our data indicate that the enzymes involved have unique multifunctional capabilities. CloA catalyzes successive oxidations at C17 and also may catalyze a double bond isomerization. Alternatively, the isomerase form of EasA, which catalyzes an isomerization activity critical for closure of the fourth and final ring of the ergoline nucleus, may catalyze the double bond isomerization. Our in vivo approach allows testing of the functions of genes without needing to rely on in vitro expression of the P450 monooxygenase encoded by cloA. Our in vivo expression platform provides the method for production of additional and novel ergot alkaloids.

I. Background

Figure 6:
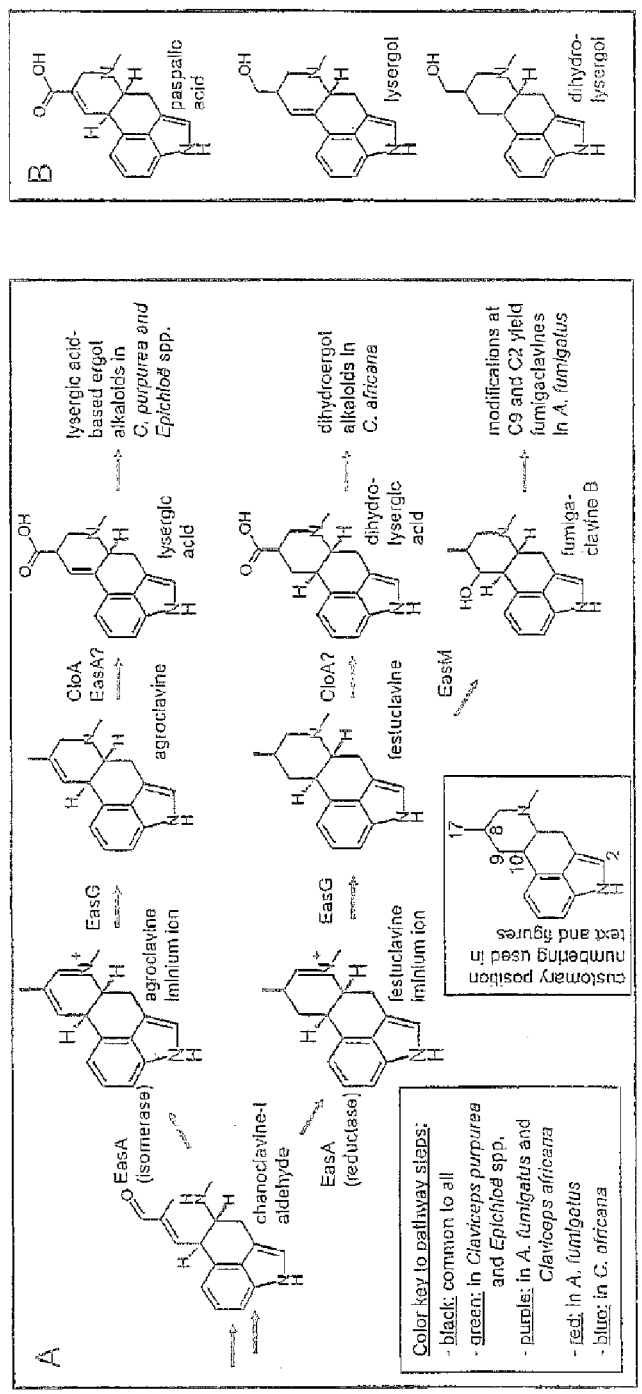

Representatives of two major families of fungi—the Clavicipitaceae and the Trichocomaceae—produce ergot alkaloids. All ergot alkaloid-producing fungi share early pathway steps before diverging to produce lineage-specific classes of ergot alkaloids (Panaccione, 2005) (FIG. 6). Several ergot alkaloid-producing members of the Clavicipitaceae including *Claviceps purpurea*, *C. paspali*, several *Epichloë* species [such as *E. festucae* var. *loliixE. typhina* isolate Lp1 (Schardl et al., 1994; Leuchtmann et al., 2014) (henceforth called *E.* sp. Lp1)], and several *Periglandula* species synthesize lysergic acid-based alkaloids in which the

TABLE 1

Ergot alkaloid accumulation (amol/conidium) in cultures of modified strains of *A. fumigatus*[a]

| Strain | chano clavine | lysergic acid[b] | agroclavine | setoclavine[b] | unknown A | unknown B |
|---|---|---|---|---|---|---|
| easA ko | 0.42 ± 0.04 | n.d. | 0.055 ± 0.01 B | 0.16 ± 0.01 B | n.d. | n.d. |
| easA/cloA | 0.58 ± 0.1 | 1.0 ± 0.1 | 0.27 ± 0.04 B | 0.60 ± 0.07 B | 0.16 ± 0.04 B | 0.062 ± 0.01 B |
| easA/easH | 0.59 ± 0.07 | n.d. | 0.81 ± 0.1 A | 2.0 ± 0.2 A | 0.38 ± 0.06 A | 0.22 ± 0.05 A |

[a]Data are means of six samples ± standard error; means followed by a different letter within a column differ significantly ($\alpha = 0.05$) in a Tukey-Kramer test.
[b]Values calculated from sums of both diastereoisomers.

Figure 1:
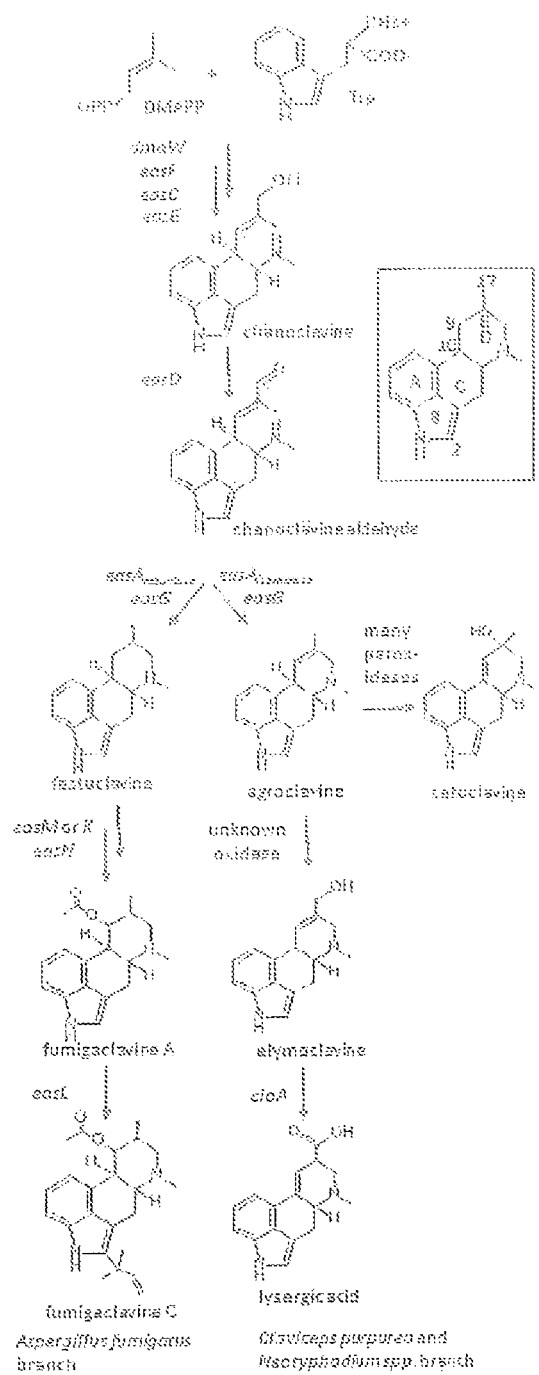
Figure 2:
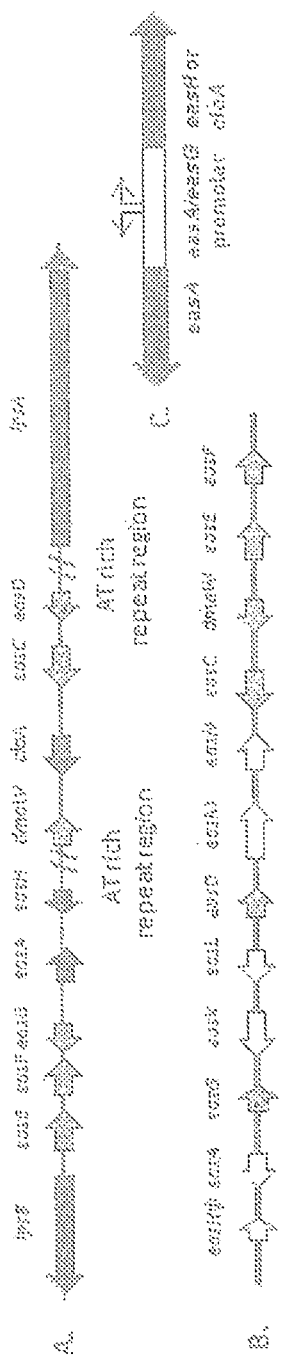
Figure 4:
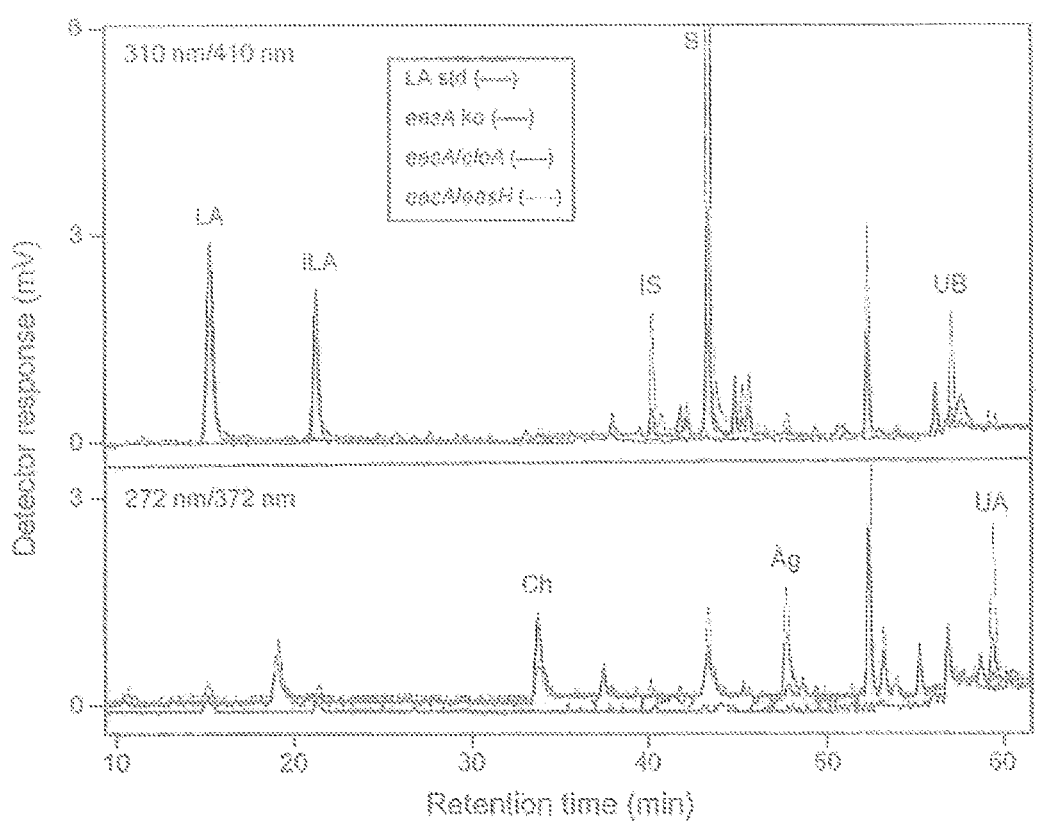
Figure 5:
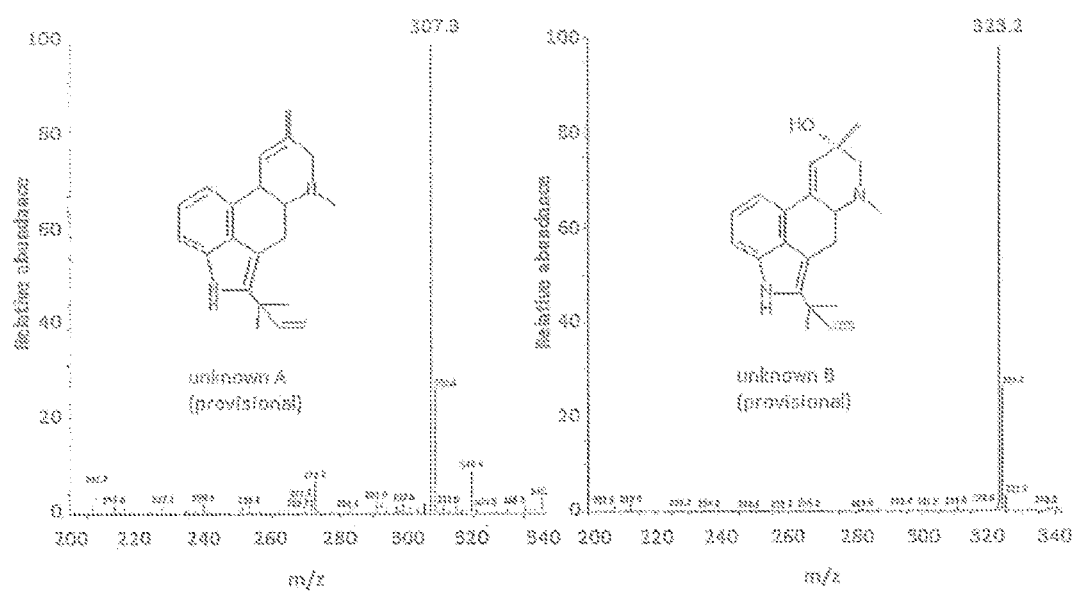

D ring (fourth or last ring to form) of the ergoline nucleus is unsaturated between carbons 9 and 10, and carbon 17 is highly oxidized (FIG. 1)(reviewed in Schardl et al., 2006; Lorenz et al., 2009; Panaccione et al., 2014). Two exceptional members of the Clavicipitaceae—*C. africana* and *C. gigantea*—produce dihydroergot alkaloids (DHergot alkaloids), which lack the double bond in the D ring but still may be oxidized or substituted at carbon 17 (Agurell, 1966; Barrow et al., 1974). In the other lineage (Trichocomaceae) are a few fungi such as *Aspergillus fumigatus* that produce clavine-based ergot alkaloids (festuclavine and fumigaclavines) in which the D ring is saturated and carbon 17 remains reduced as a methyl group (Wallwey and Li, 2011; Panaccione et al., 2012) (FIG. 1). Several of the lysergic acid derivatives and DHergot alkaloids of the Clavicipitaceae are valued for their pharmacological activity and used as described above (see Significance section; Table 1). The fumigaclavines of *A. fumigatus* have not been used clinically.

The first branch point of the pathways found in these two fungal lineages occurs during D ring closure. In *A. fumigatus*, *C. africana*, and *C. gigantea*, the 8,9 double bond in chanoclavine aldehyde is reduced by the enzyme EasA, allowing the aldehyde group free rotation to interact with the secondary amine to promote ring closure via Schiff base formation (Coyle et al., 2010; Cheng et al., 2010b; Wallwey et al., 2011). The resulting iminium ion is subsequently reduced by EasG to form festuclavine (Wallwey et al., 2010; Cheng et al., 2010b). Most common ergot alkaloid-producing fungi in the Clavicipitaceae, however, diverge from *A. fumigatus* at the first branch point and synthesize the 8,9 unsaturated clavine agroclavine from chanoclavine aldehyde via the activity of an alternate version of EasA that acts as an isomerase rather than a reductase (Coyle et al., 2010; Cheng et al., 2010b). In *C. purpurea*, *C. paspali*, and *Epichloë* spp., agroclavine is oxidized at C17 to form elymoclavine, and elymoclavine is further oxidized and isomerized to form lysergic acid (FIG. 1). Lysergic acid is then incorporated into ergopeptines and/or lysergic acid amides. Our easA knockout strain (easA ko) of *A. fumigatus* (Coyle et al., 2010) provides an excellent background for reprogramming of the *A. fumigatus* ergot alkaloid pathway to a lysergic acid-based pathway. FIG. 6 shows (A) branch points and critical steps in the biosynthesis of ergot alkaloids in different lineages of fungi, and (B) rarely encountered ergot alkaloids originating from mutant pathways.

A second branch point—this one between members of the Trichocomaceae such as *A. fumigatus* and the DHergot alkaloid producers *C. africana* and *C. gigantea*—occurs after formation of festuclavine. In *A. fumigatus* and relatives, festuclavine may be modified at carbons 9 and/or 2 to form various fumigaclavine derivatives (FIG. 1). Alternatively, in *C. africana* and *C. gigantea*, festuclavine in oxidized at C17 and, in the case of *C. africana*, incorporated into more complex dihydroergot alkaloids. Our easM ko of *A. fumigatus* provides an ideal background for analysis of pathway genes downstream from festuclavine in the DHergot alkaloid producers *C. africana* and *C. gigantea*.

Figure 7:
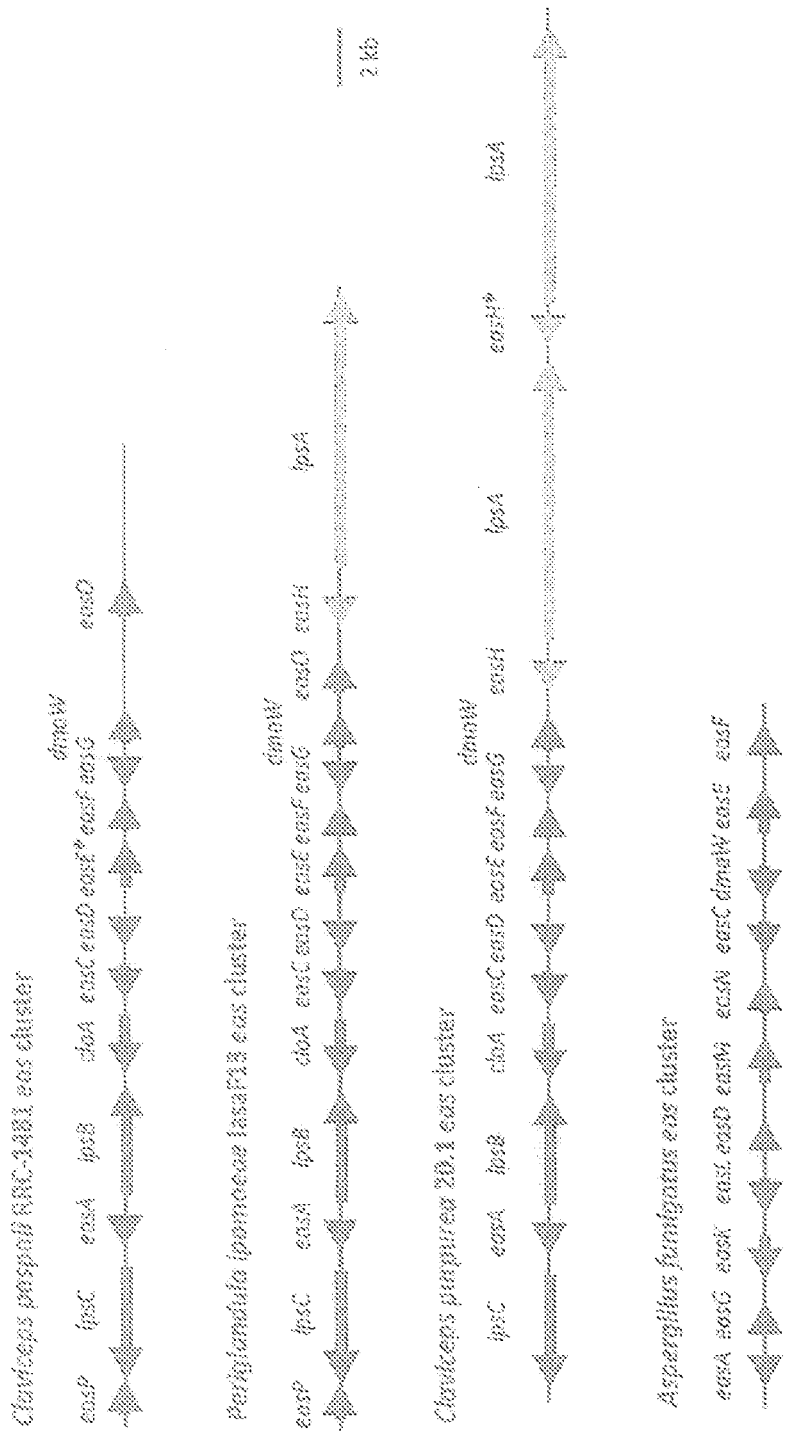

Another important background point to emphasize is that genes involved in ergot alkaloid biosynthesis are clustered in the genes of the producing fungus (FIG. 7). These gene clusters (referred to as eas clusters for ergot alkaloid synthesis) contain core genes that are conserved among all ergot alkaloid producers as well as lineage-specific genes required for producing the unique alkaloids found in different fungi. The clusters of *C. purpurea*, *C. paspali*, and the more distantly related *P. ipomoeae* (Schardl et al., 2013a), *Metarhizium robertsii* (formerly *Metarhizium anisopliae*), and *M. acriduin* (Gao et al., 2011) are well conserved in terms of relative gene order and orientation. The clusters of *Epichloë* spp. show much more variability in gene order and orientation; the variability may be related to interspersion of numerous transposable elements in the eas clusters of these *Epichloë* spp. (Schardl et al., 2013a). In the Trichomocaeae ergot alkaloid biosynthesis genes also are clustered but the order and orientation differs from that observed in the Clavicipitaceae (Panaccione and Coyle, 2005; Unsold and Li, 2005; Wallwey and Li, 2011). Genes shown in FIG. 7 that are in heavy black print represent genes that are common to all ergot alkaloid producers. Other genes are involved in incorporating lysergic acid into ergopeptines. Other genes are thought to be required for assembling of a specific lysergic acid amide. While other genes are unique to *A. fumigatus*.

An Embodiment of the Present Invention

Figure 9:
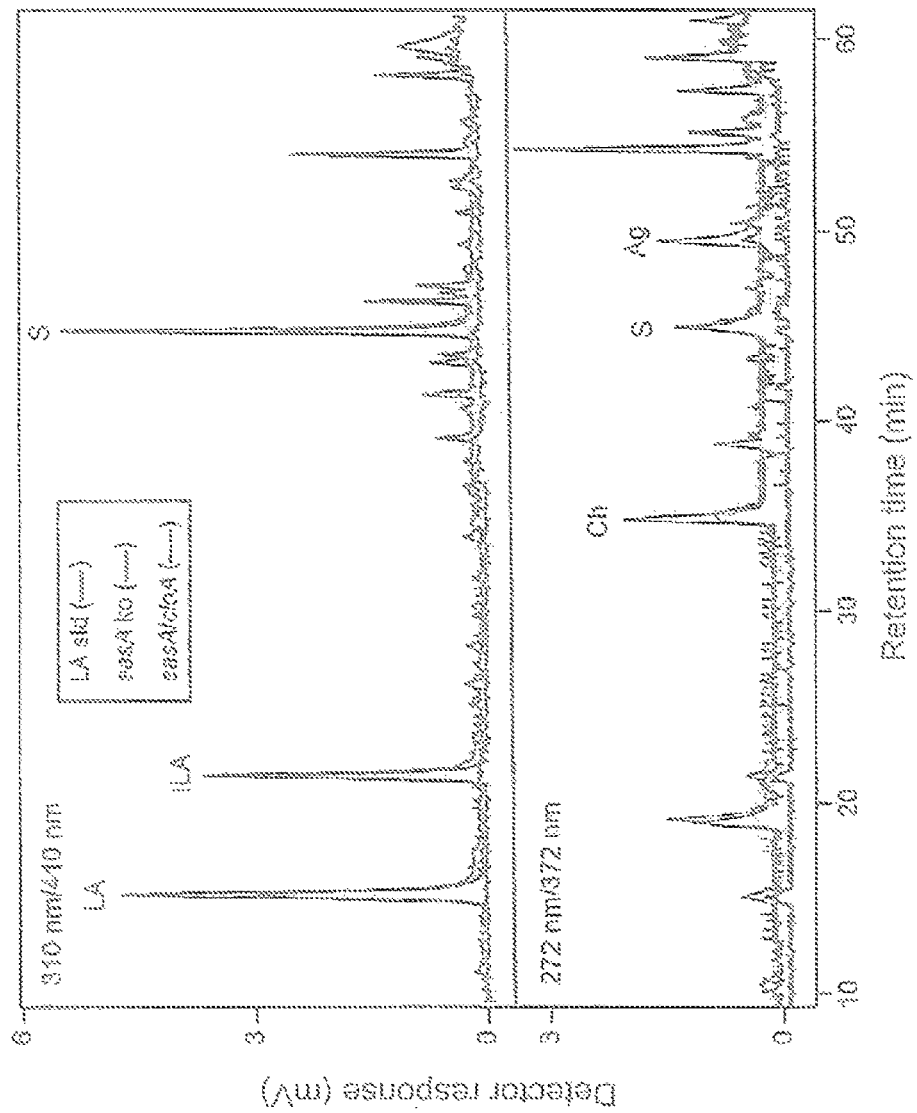
Figure 10:
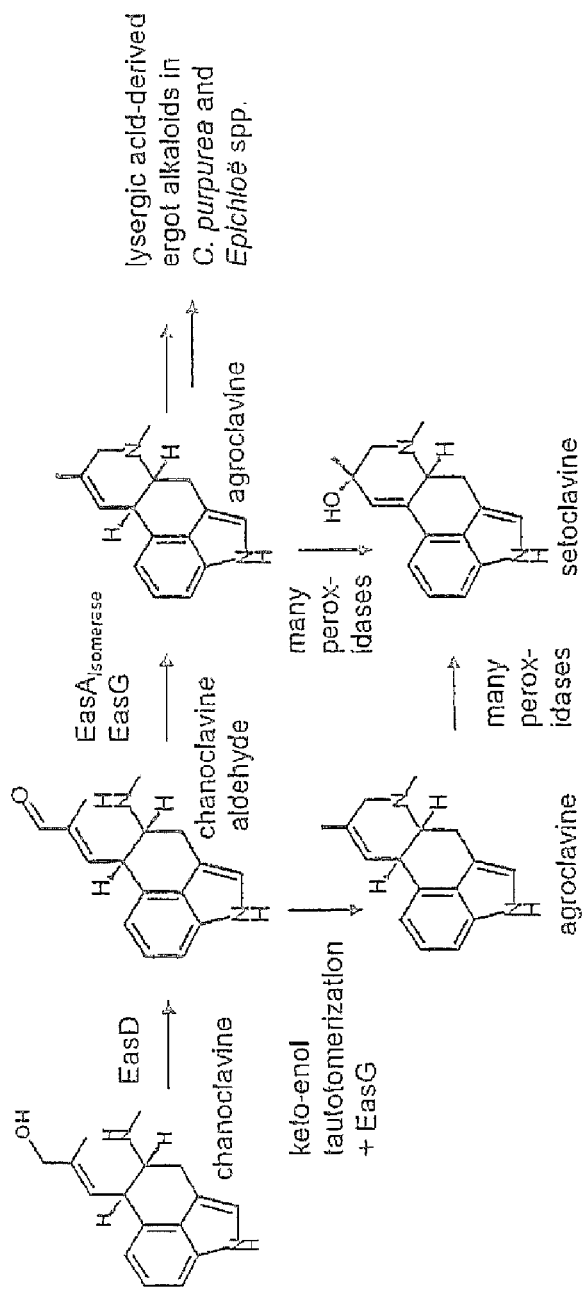

Reprogramming *A. fumigatus* to Produce Lysergic Acid (LA) Via Exchange of easA Alleles and Addition of cloA Our previous work showed that different lineages of ergot alkaloid producers carry different alleles of easA that determine the first branch point of the ergot alkaloid pathway (Coyle et al., 2010). By expressing the allele of easA found in *C. purpurea* (Coyle et al., 2010), *Epichloë festucae* var. *lolii* (formerly *Neotyphodium lolii*) (Cheng et al., 2010b), or *E.* sp. Lp1 (Robinson and Panaccione, 2014) in *A. fumigatus* in which its native easA allele is knocked out (*A. fumigatus* easA ko), we have engineered *A. fumigatus* to produce agroclavine as opposed to festuclavine, which starts *A. fumigatus* down the pathway to LA-based ergot alkaloids (refer to FIG. 6). We used the bidirectional easA/easG promoter of *A. fumigatus* to drive expression of each of several candidate oxidase genes (easD, easH, or cloA from *E.* sp. Lp1) along with expression of the isomerase allele easA from *E.* sp. Lp1 (FIG. 8) in the *A. fumigatus* easA ko background. Strains expressing EasA/EasD or EasA/EasH accumulated agroclavine (as a result of expression of the isomerase allele of easA) but strains expressing EasA/CloA produced lysergic acid and its diastereoisomers isolysergic acid (FIG. 9). The data demonstrate that the ergot alkaloid cluster gene cloA encodes an enzyme that catalyzes all the oxidations of agroclavine to lysergic acid (FIG. 9). Moreover, since only lysergic acid (and not its 8,9 double bond isomer paspalic acid) was produced in our EasA/CloA strain, the double bond isomerization is catalyzed by one of the expressed enzymes (EasA or CloA) as opposed to happening spontaneously over time. The EasA/CloA strain of *A. fumigatus* easA ko is the first fungus known to produce lysergic acid as its biosynthetic endpoint in culture, and our data clearly show that expression of two genes from a lysergic acid-producing fungus is sufficient (in conjunction with the product of the native allele of easG in *A. fumigatus*) to produce lysergic acid from the common pathway intermediate chanoclavine aldehyde. In this particular study, we could not distinguish CloA or EasA as the source of the double bond isomerase activity because of the need to express EasA to produce agroclavine as substrate for CloA; however, in the proposed project we will distinguish EasA or CloA as the source of double bond isomerase activity by reciprocally pairing genes from different sources.

The ergot alkaloid profiles of the strains shown in FIG. 9 require a more detailed explanation. Analyses of *A. fumigatus* easA ko (even without expression of or *E.* sp. easA allele) shows that it accumulates small quantities of agroclavine (FIG. 9). This agroclavine likely derives from keto-enol tautomerization of chanoclavine aldehyde, which builds up in this strain in the absence of a functional EasA. The enol tautomer can rotate around C8 and then tautomerize back to the aldehyde form. After this isomerization, D ring formation may occur as described above (via Schiff base formation and reduction by EasG). Agroclavine that accumulates is readily oxidized at C8 to form setoclavine by non-specific peroxidases from many sources (Beliveau and Ramstad, 1967; Panaccione et al., 2003; Coyle et al., 2010)]. The presence of agroclavine in easA ko and setoclavine in easA ko or its lysergic acid-producing derivative are explained in FIG. 10 and its legend.

Figure 11:
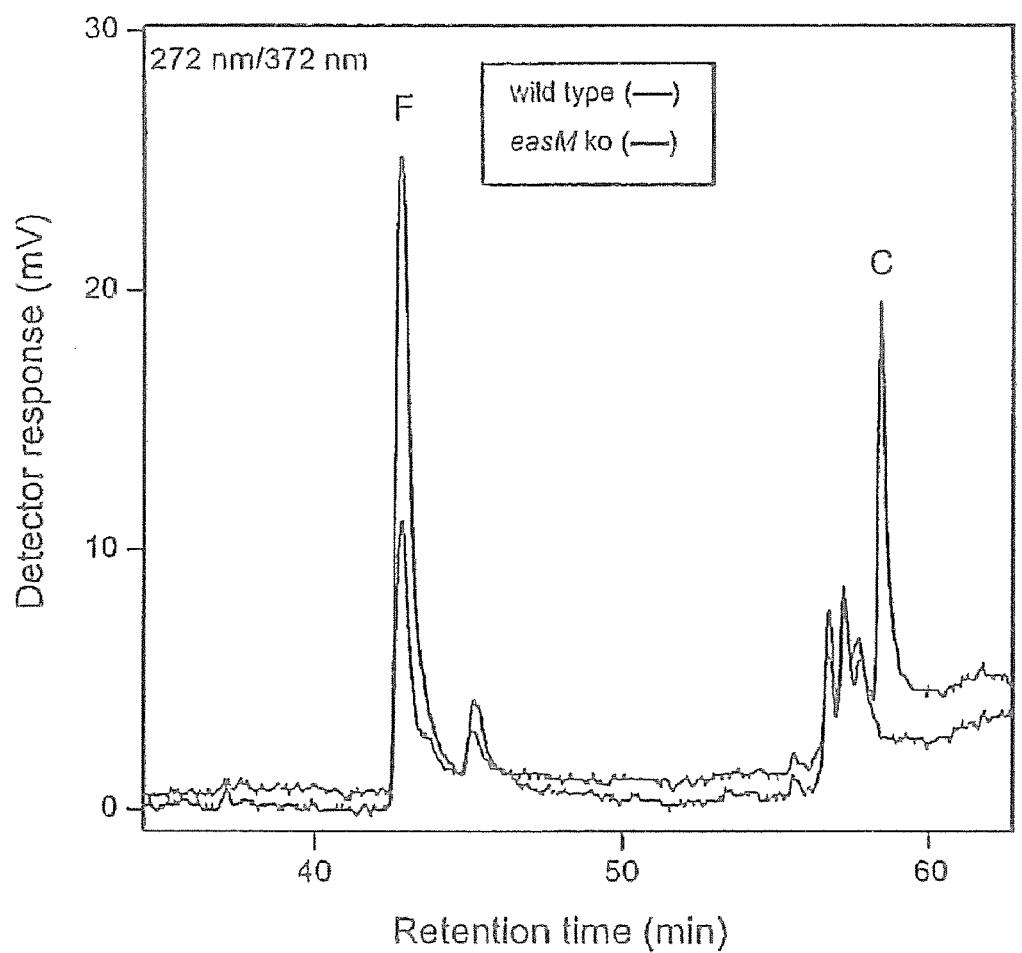
FIG. 11 shows fluorescence HPLC chromatogram showing festuclavine (F) accumulating to higher concentration in easM ko strain and lack of pathway end product fumigaclavine C in the easM ko.
Figure 12:
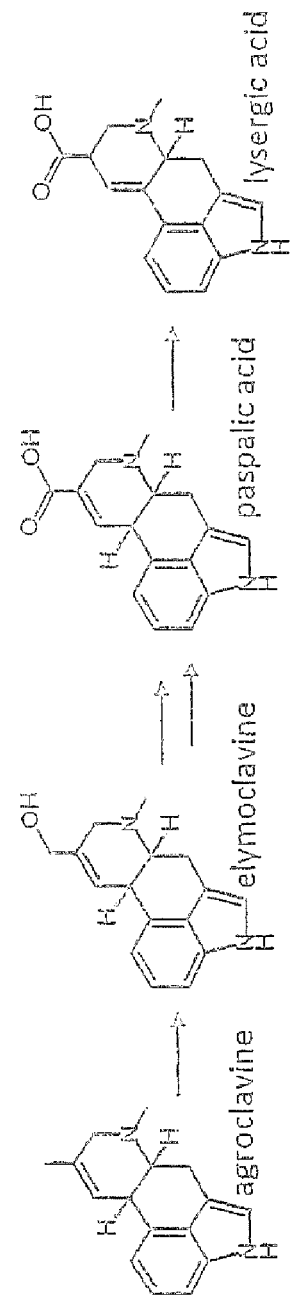
FIG. 12 shows a pathway from agroclavine to lysergic acid. Double arrow: aldehyde intermediate omitted.

Engineering of Festuclavine-Accumulating Strain of *A. fumigatus* to Serve as Host for Studies on Dihydroergot Alkaloid Biosynthesis by Knockout of eas Whereas the easA knockout of *A. fumigatus* is the ideal recipient strain for expression studies designed to elucidate the origins of paspalic acid and lysergol, to study genes involved in dihydroergot alkaloid synthesis, the ideal recipient strain should accumulate festuclavine, which is the reduced analog of agroclavine and will serve as substrate for genes involved in dihydroergot alkaloid biosynthesis. We have already prepared such a strain by knocking out gene easM of *A. fumigatus*. Sequence data indicate that easM encodes a P450 monooxygenase, and our knockout data demonstrate that this enzyme is required for oxidizing festuclavine into downstream fumigaclavines (FIG. 11). In the easM knockout, festuclavine accumulates and no downstream fumigaclavines are produced. In some embodiments of the invention, a strain of *A. fumigatus* with a knockout of gene easM will be used.

Disarming of *A. fumigatus*

Since *A. fumigatus* is an opportunistic pathogen, any strain that may eventually be used commercially must be disarmed by knocking out a virulence gene. We have knocked out alb1 (Tsai et al., 1999) which encodes a polyketide synthase required for melanin biosynthesis and virulence in *A. fumigatus*. The albino nature of the mutants provides a convenient visual marker for these strains as well. We have made this mutation in the *A. fumigatus* easA ko background. In certain embodiments of the invention, a strain of *A. fumigatus* with a knockout alb1 in the easM ko background will be used. We have routinely used acetamidase (Hynes et al., 1983) as a third selectable marker for transformation in *A. fumigatus*, allowing a round of manipulations beyond those described in manipulating the ergot alkaloid pathway (which require hygromycin and phleomycin resistance markers).

Methods for Genome Sequencing that Will Support Both Specific Aims:

General Methods:

In specific embodiments of the invention, specific ergot alkaloid biosynthesis genes from various *Claviceps* or *Periglandula* species, or in some cases *E.* sp. Lp1, are amplified to produce unique ergot alkaloids, fuse those genes to *A. fumigatus* promoters, and express them in one of two different *A. fumigatus* mutant backgrounds (easA ko or easM ko). These mutant backgrounds do not complete the typical *A. fumigatus* pathway but instead accumulate substrates for the enzymes encoded by the introduced genes. These include routine molecular biology work and PCR, as well as fusion PCR for preparing promoter-coding sequence constructs for transformation (e.g., FIG. 8). We routinely transform *A. fumigatus* with three different selectable markers (hygromycin resistance, phleomycin resistance, and acetamide utilization as a nitrogen source). We have extensive experience with analyzing ergot alkaloids from *A. fumigatus* and other fungi by fluorescence HPLC (e.g., FIGS. 9 and 10) and LC/MS (e.g., Panaccione and Coyle, 2005; Coyle and Panaccione, 2005; Panaccione et al., 2006; Coyle et al., 2010; Goetz et al., 2011; Robinson and Panaccione, 2012; Panaccione et al., 2012; Ryan et al., 2103).

Genome Sequencing

Considering the current low price of genome sequencing, the small size of fungal genomes (~40 Mb), and extensive information on ergot alkaloid gene clusters available for comparison (Schardl et al., 2013ab), in some embodiments of the invention, the genomes of the fungi are sequenced. This sequencing can be done quickly in a single MiSeq flow cell. Having sequence data available offers several advantages over the alternate approach of using existing sequences of related genomes to prepare degenerate primers to clone genes of interest, then (in some cases) relying on TAIL-PCR to acquire flanking regions, and finally sequencing assembled clones, stepwise, with Sanger technology. One advantage is that we will be able to prepare specific primers to amplify the relevant genes directly, rather than taking the steps outlines in the previous sentence, thus allowing us to avoid pitfalls and also save time and money when all the genes from several fungi are considered. A second advantage is that we will obtain information about all genes in each fungus's ergot alkaloid gene cluster. A third advantage is that the genome sequences will strengthen the institutional capacity for research as well as that of the greater fungal toxin research community. The genomes of the *Periglandula* species were not sequenced wherein because those fungi are obligate symbionts of plants, and their genomes are present in a relatively low proportion compared to that of the more complex genomes of their plant hosts. We already have access to sequence data from one exceptional *Periglandula* species—*P. ipomoeae*—which grows superficially on leaves such that its hyphae are separable from plant tissue (Schardl et al., 2013a).

Barcoded libraries of genomes of haploid fungi *C. paspali* NRRL 3080, *C. africana*, and *C. gigantea* may be prepared with the Illumina TruSeq kit and sequenced to approximately 50-fold coverage in a single MiSeq flow cell at the University of Kentucky Advanced Genomics Technology Center [which has led sequencing efforts on 19 other fungi with ergot alkaloid synthesis clusters (Schardl et al., 2013ab)]. The MiSeq platform offers the advantage of relatively long reads (2×250 nt per cluster) and 15 million clusters per flow cell. Estimating a mean genome size of 38 Mb for each of the *Claviceps* spp. [based on the mean genome size of *C. purpurea, C. fusiformis*, and *C. paspali* RRC-1481 (Schardl et al., 2013a)], we should achieve approximately 50-fold coverage for each genome. Genomes will be assembled with Newbler or, if the number of read is too great for that program, CLCBio from CLC Genome Workbench. Assembled genomes will be queried with sequences from homologues of easA, cloA, and other ergot alkaloid synthesis genes available from *C. purpurea, C. paspali* RRC-1481, several *Epichloë* species, and *Periglandula ipomoeae.*

Biosynthetic Origin of Lysergol (Prophetic):

Lysergol is the delta 9,10 double bond isomer of elymoclavine. Elymoclavine (an isomer of lysergol carrying an 8,9 double bond) is the first oxidation step in the oxidation series of agroclavine into lysergic acid. Lysergol appears to be a biosynthetic dead end, as it cannot be further oxidized to lysergic acid (Maier et al., 1988; Groger and Floss, 1997). These observations indicate that after isomerization of the double bond from the 8,9 to the 9,10 position, CloA is not able to further oxidize C17, and that in a fully functioning pathway, double bond isomerization takes place after oxidation.

Fungi that accumulate lysergol clearly have the enzymatic capacity to isomerize the double bond but appear to do so prematurely such that isomerization occurs when C17 is at a preliminary oxidation state. Once lysergol forms it cannot be further oxidized (Groger and Floss, 1997; Maier et al., 1988).

Testing Lysergol:

In some embodiments of the invention, alleles of easA and cloA are amplified from *Periglandula* species, which are symbiotic fungi associated with high lysergol-producing morning glory species. We have infected plant material from *Stictocardia tiliifolia, S. beraviensis*, and *Argyreia speciosa* each of which accumulates lysergol such that it comprises >98% of the total ergot alkaloid yield (see Table 3 set forth below). We also have several accessions of *Ipomoea parasitica* in which lysergol comprises >50% of the total ergot alkaloid yield.

TABLE 3

Lysergol and other ergot alkaloids (μg/g seed) extracted from morning glory symbiota

| Plant (accession) | chano-clavine[1] | lysergol | ergo-pep-tines[2] | proportion lysergol | PCR of fungal genes |
|---|---|---|---|---|---|
| Stictocardia tiliifolia | 0 | 276 | 0 | 1.0 | n.a.[3] |
| S. beraviensis 323 | 0 | 623 | 0 | 1.0 | n.a. |
| S. beraviensis 324 | 5 | 1510 | 0 | >0.99 | yes |
| Argyreia speciosa | 1 | 38 | 0 | 0.98 | n.a. |
| Ipomoea parasitica 630 | 254 | 978 | 675 | 0.51 | n.a. |
| I. parasitica 674 | 152 | 551 | 199 | 0.61 | n.a. |

[1]early pathway intermediate that frequently accumulates (FIG. Y)
[2]sum of ergobalansine and ergosine
[3]not attempted Because of their obligately symbiotic nature, the *Periglandula* spp. associated with high lysergol-yielding morning glories will not be sequenced. Instead isolated mixed fungus-plant DNA directly from infected plant material with Zymogen kit may be used successfully for this purpose. In our preferred approach to amplify the entirety of the cloA locus, PCR can be primed from a primer designed to anneal near the 3'-end of the coding sequences of lpsB and another designed to anneal near the 3'-end of the coding sequences of easC. These two genes flank cloA in the eas clusters of *P. ipomoeae, C. paspali* RRC-1481, and *C. purpurea* (FIG. 7), as well as in more distantly related members of the Clavicipitaceae *Metarhizium robertsii* (formerly classified as *M. anisopliae*) and *Metarhizium acridum* (Gao et al., 2011). (Eas clusters from *Metarhizium* spp. are not pictured in FIG. 7, but they are identical in gene composition, order, and orientation with that of *C. paspali* RRC-1481.) The PCR product (expected to be 5 kb) can be Sanger sequenced, synthesizing new primers for successive steps. The complete easA gene can be amplified from primers designed to anneal near the 5'-ends of the coding sequences of lpsB and lpsC which flank easA in the diverse genomes listed immediately above, and Sanger sequenced. An alternate approach to cloning these genes is outlined under alternate plans lysergol set forth below. A further alternative is to express alleles of easA and cloA from an isolate of *Epichloë coenophiala* which produces lysergol and for which genome sequence is available. Coding sequences and 3'UTRs of cloA and easA can be fused to the bidirectional easA/easG promoter of *A. fumigatus* (FIG. 8) in combination with the alleles of the alternate gene from *E.* sp. Lp1 by fusion PCR. The *E.* sp. Lp1 alleles represent alleles from a pathway able to complete all required steps to lysergic acid from agroclavine. In some embodiments of the invention, the following combinations of alleles are expressed in *A. fumigatus* easA ko, Periglandula sp. easA and P. sp. cloA
P. sp. easA and Epichloë sp. Lp1 cloA
E. sp. Lp1 easA and P. sp. cloA
Epichloë coenophiala easA and Epichloë coenophiala cloA Translational Implications (Lysergol):

Lysergol can be used directly for synthesizing the pharmaceutically important ergot alkaloids nicergoline and pergolide. A cultivable source of lysergol is useful for preparation of pharmaceuticals that are derived from lysergol and also is useful in engineering of novel compounds. Lysergol is not a controlled substance, simplifying the conduct of business, and it cannot be as easily adapted to illicit drug manufacturing as lysergic acid.

Alternate Plans (Lysergol):

The lysergol experiments are the most demanding from a technical perspective, because we will not have direct sequence data for the fungi. Only one *Periglandula* species has been sequenced, but its eas cluster and eas sequences match well with those of *Claviceps* and *Metarhizium* spp. (Schardl et al., 2013a). Our primary strategy for cloning easA and cloA is based on the assumption that clusters will be organized the same as in *P. ipomoeae* (and as they are in *Claviceps* and *Metarhizium* spp.). In certain embodiments of the invention, conserved internal regions of easA and cloA will be amplified based on degenerate primers designed to anneal to most versions of each gene. Then the remainders of each coding sequence and some 3'-UTR can be amplified by TAIL-PCR (Singer and Burke, 2003; Liu et al., 2005; Liu and Chen, 2007). We have already cloned internal portions of other genes from the *P.* sp. symbiont of *S. beraviensis* with degenerate primers.

Figure 13:
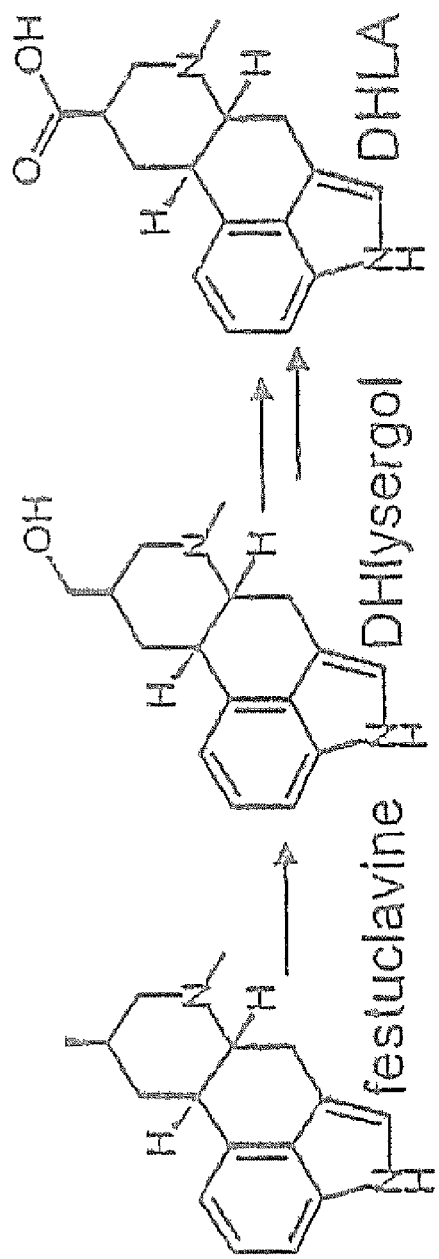
FIG. 13 shows a pathway from festuclavine to dihydrolysergic acid (DHLA). Double arrow: aldehyde intermediate omitted.

The Biosynthetic Origin of Dihydroergot Alkaloids:
Biosynthetic Origin of Dihydrolysergic Acid (DHLA)(Prophetic):

*Claviceps africana* produces DHLA-derived ergot alkaloids such as dihydroergosine. The reduction of the 8,9 double bond to the reduced dihydro state appears to occur after the chanoclavine stage and before or during closure of the D ring (to yield festuclavine, in this case) (Barrow et al., 1974). We have DNA from *C. africana* and have used it to successfully clone the easA gene (sequence appears in supplement to Cheng et al., 2010b) by PCR with degenerate primers based on sequence data from other *Claviceps* spp. We also have prepared a recipient strain of *A. fumigatus* that accumulates the dihydrolysergic acid precursor festuclavine by knocking out the P450 monooxygenase gene easM (Bilovol and Panaccione, unpublished data; Section II. B). Festuclavine is the 8,9 reduced version of agroclavine and should serve as substrate for versions of CloA that are capable of producing DHLA through a series of oxidations at C17 (FIG. 13). The idea that CloA from a lysergic acid producer will accept the dihydroergot alkaloid festuclavine as substrate (as opposed to its typical, delta-8,9 substrate agroclavine) is supported by the observations that the next enzyme in the pathway of lysergic acid producers, lysergyl peptide synthetase 2 (encoded by lpsB) accepts dihydrolysergic acid with a K similar to which it acts on lysergic acid (Riederer et al., 1996).

Testing DHLA:

We have generated a strain of the fungus *A. fumigatus* that produces festuclavine as its biosynthetic end point by knockout of the *A. fumigatus* gene easM. This festuclavine accumulator may serve as recipient for transformations, because festuclavine is the intermediate oxidized to DHLA in the DHLA-based pathway of *C. africana* (Barrow et al., 1974). In some embodiments of the invention, the expression of cloA of *E.* sp. Lp1 is under the control of the *A. fumigatus* easA promoter for the production of DHLA. In other embodiments of the invention, cloA is amplified from the DHLA producer *C. africana* and express it in *A. fumigatus* easM ko under the control of the *A. fumigatus* easA promoter. The coding sequences and ~300 by or 3'-UTR can be PCR amplified from *C. africana* based on specific primers designed based on genomic sequence data.

Translational Implications (DHLA):

Dihydrolysergic acid is a preferred starting point for the synthesis of most of the major pharmaceutically important ergot alkaloids (with the exception of bromocriptine). Direct production of the compound (as opposed to purifying it after hydrolysis of ergopeptines to lysergic acid and reduction of lysergic acid) will benefit pharmaceutical industries. DHLA is not listed as a controlled substance by the US Drug Enforcement Agency (DEA) and would not be readily useful for illegal drug biosynthesis.

Alternate Plans (DHLA):

In certain embodiments of the invention, easA from the DHLA producer *C. africana* along with cloA from *E.* sp. Lp1 and *C. africana* are used. These dual-gene expression constructs can be set up with the two genes divergently transcribed from the *A. fumigatus* easA/easG promoter, as we have done successfully with easA and cloA from *E.* sp. Lp1 (FIG. 8).

The biosynthetic origin and engineering of dihydrolysergol DHlysergol) (Prophetic):

The maize ergot fungus produces dihydrolysergol as the end product of its ergot alkaloid pathway. Dihydrolysergol also occurs in the biosynthetic pathway to DHLA and DHLA derivatives in *C. africana* (Barrow et al., 1974). The reason that *C. gigantea* stops its pathway at DHlysergol is unknown but will be revealed by expression studies and eas cluster sequence analysis.

Testing DHlysergol:

In certain embodiments of the invention, the coding sequences of cloA is amplified from the initiation codon through the termination codon, along with about 300 by of 3'UTR. Primers can be designed based on *C. gigantea* genomic sequence. In further embodiments of the invention, the cloA fragment is joined to the easA promoter of *A. fumigatus* and introduced into *A. fumigatus* easM ko by cotransformation with pBCphleo (while selecting on phlemomycin). Transformants can be analyzed by fluorescence HPLC and LC/MS as described previously.

Translational Implications (DHlysergol):

DHlysergol would be an excellent starting molecule for several of the more important pharmaceutical ergot alkaloids, such as nicergoline, cabergoline, and pergolide (Table 3). As the end product of the engineered strain, dihydrolysergol would not need to be hydrolyzed and purified from more complex ergot alkaloids or reduced to the dihydro state. DHlysergol would not be regulated as a controlled substance, simplifying business practices and would not be easily exploited for illicit drug synthesis.

Alternate Plans (DHlysergol):

In other embodiments of the invention, *C. gigantea* cloA is expressed in conjunction with *C. gigantea* easA.

Outcomes:

The present invention has a strong basic rationale founded in the historical and medicinal importance of the ergot alkaloids and novel and interesting enzymatic activities. Those persons skilled in the art will understand that the present invention has strong translational possibilities as set forth herein.

Generally, the present invention provides a strain of a fungus for expressing one or more genes of the ergot alkaloid biosynthesis pathways from one or more fungus. The fungus may be for example, but not limited to, *Aspergillus fumigatus, Penicillium commune*, or any fungus having a pathway similar to *Aspergillus fumigatus*, as the host fungus for gene expression.

It will be understood by those persons skilled in the art that the present invention includes using easA or cloA genes from ergot alkaloid producing fungi that are functionally similar to the genes, for example but not limited to, from *Claviceps purpurea* or any of *Epichloë* species.

Generally, the present invention provides producing novel ergot alkaloids in *A. fumigatus* by the following method: expressing ergot alkaloid synthesis genes from other fungi in *A. fumigatus* easA knockout or easM knockout and letting the native prenyl transferase EasL act on any ergot alkaloids so produced in order to produce novel prenylated alkaloids. This method of this invention produces novel alkaloids by expressing ergot alkaloid pathway genes from other sources.

Preferred embodiments of the present invention provide:

1. A strain of fungus comprising *Aspergillus fumigatus* (*A. fumigatus*) and expressing one or more genes of the ergot alkaloid biosynthesis pathways from one or more fungus selected from the group consisting of:

a. *Epichloë festucae* var. *lolii*×*Epichloë typhina* isolate Lp1 (*E.* sp. Lp1);

b. *Claviceps* species;

c. *Claviceps africana* (*C. africana*);

d. *Claviceps gigantea* (*C. gigantea*);

e. *Periglandula* species; and f. *Epichloë coenophiala,* wherein gene easA or gene easM is inactivated in said *A. fumigatus.*

2. The strain of embodiment 1 above, wherein said one or more genes of the ergot alkaloid biosynthesis are selected from the group consisting of:

a. easA; and b. cloA.

3. The strain of embodiment 2 above, wherein said gene easA is inactivated in said *A. fumigatus*, and said one or more fungus is *E.* sp. Lp1.

4. The strain of embodiment 2 above, wherein said gene easA is inactivated in said *A. fumigatus*, and said one or more fungus is a *Periglandula* species or *Epichloë coenophiala* that produces lysergol.

5. The strain of embodiment 2 above, wherein said gene easA is inactivated in said *A. fumigatus*, and said one or more fungi are a *Periglandula* species or *Epichloë coenophiala* and *E.* sp. Lp1, wherein said expressing gene easA is from a *Periglandula* species or *Epichloë coenophiala* and said expressing gene cloA is from *E.* sp. Lp1.

6. The strain of embodiment 2 above, wherein said gene easA is inactivated in said *A. fumigatus*, and said one or more fungi are a *Periglandula* species or *Epichloë coenophiala* and *E.* sp. Lp1, wherein said expressing gene cloA is from a *Periglandula* species or *Epichloë coenophiala* and said expressing gene easA is from *E.* sp. Lp1.

7. The strain of embodiment 2 above, wherein said gene easM is inactivated in *A. fumigatus*, said one or more fungus is *E.* sp. Lp1, and said expressing one or more genes of the ergot alkaloid biosynthesis is cloA.

8. The strain of embodiment 2 above, wherein said gene easM is inactivated in *A. fumigatus*, said one or more fungus is *C. africana*, and said expressing one or more genes of the ergot alkaloid biosynthesis is cloA.
9. The strain of embodiment 2 above, wherein said gene easM is inactivated in said *A. fumigatus*, said one or more fungus is *C. gigantea*, and said expressing one or more genes of the ergot alkaloid biosynthesis is cloA.
10. A method for producing lysergic acid comprising inactivating an ergot alkaloid biosynthesis pathway gene from the fungus *A. fumigatus* and expressing genes easA and cloA from the fungus *E.* sp. Lp1, wherein said inactivated ergot alkaloid biosynthesis pathway gene is easA of *A. fumigatus*.
11. A method for producing novel ergot alkaloids comprising inactivating an ergot alkaloid biosynthesis pathway gene from the fungus *A. fumigatus* and expressing genes easA and cloA from the fungus *E.* sp. Lp1, wherein said inactivated ergot alkaloid biosynthesis pathway gene is easA of *A. fumigatus*.
12. A method for producing dihydrolysergic acid (DHLA) comprising inactivating gene easM in *A. fumigatus* and expressing gene cloA from *E.* sp. Lp1 or gene cloA from *C. africana* in said *A. fumigatus* strain.
13. A method for producing dihydrolysergol (DHlysergol) comprising inactivating gene easM in *A. fumigatus* and expressing one or more genes of the ergot alkaloid biosynthesis from *C. gigantea* selected from the group consisting of:
a. cloA; and
b. cloA and easA,
wherein said gene(s) from *C. gigantea* are expressed in said *A. fumigatus* strain.
14. A strain of fungus comprising a species of a fungus and expressing one or more genes of the ergot alkaloid biosynthesis pathways from one or more of said fungus, wherein said fungus has a pathway similar to *A. fumigatus.*
15. The strain of embodiment 14 set forth above, wherein said one or more genes of the ergot alkaloid biosynthesis are selected from the group consisting of:
a. easA; and
b. cloA.
16. The strain of embodiment 15 set forth above wherein said easA or cloA genes from said ergot alkaloid producing fungi are functionally similar to the genes from *Claviceps purpurea* or any of *Epichloë* species.
17. A method of producing ergot alkaloids in *A. fumigatus* comprising expressing ergot alkaloid synthesis genes from other fungi in *A. fumigatus* easA knockout or easM knockout, allowing native prenyl transferase EasL act on any ergot alkaloids so produced for producing prenylated alkaloids.
18. A method of producing ergot alkaloids in a strain of *A. fumigatus* comprising expressing a bidirectional easA/easG promoter of *A. fumigatus* to drive expression of oxidase genes in the *A. fumigatus* EasA knock-out background for producing ergot alkaloids.
19. The method of embodiment 18 set forth above, wherein a EasA gene from *E.* sp. Lp1 is expressed in said *A. fumigatus* EasA knock-out background.
20. The method of embodiment 19 set forth above, wherein said EasA gene from *E.* sp. Lp1 includes expression of cloA.
21. A method for the production of lysergic acid comprising providing for the expression of EasA/CloA in *A. fumigatus* easA knockout for producing lysergic acid.
22. A method of producing a festuclavine-accumulating strain of *A. fumigatus* comprising a knock-out of the easM allele for producing a festuclavine accumulating strain of *A. fumigatus.*
23. A method for producing lysergic acid in *A. fumigatus* easA knock-out providing amplifying *E.* sp. Lp1 easA and *E.* sp. Lp1 cloA for producing lysergic acid.
24. A method for accumulating lysergol comprising amplifying easA and cloA from *Periglandula* in plant material selected from the group consisting of *Stictocardia tiliifolia, S. beraviensis, Argyreia*, and *Ipomoea* species or by amplifying easA and cloA from *Epichloë coenophiala* for accumulating lysergol.
25. A method for producing lysergol comprising providing expressing *Periglandula* sp. easA and *P.* sp. cloA or *Epichloë coenophiala* easA and *Epichloë coenophiala* cloA in a *A. fumigatus* easA knock-out strain for producing lysergol.
26. A method for producing lysergol comprising expressing *P.* sp. easA or *Epichloë coenophiala* easA and *Epichloë* sp. Lp1 cloA in a *A. fumigatus* easA knock-out strain for producing lysergol.
27. A method for producing lysergol comprising *A. fumigatus* easA knock-out strain through expression of *E.* sp. Lp1 easA and *P.* sp. cloA or *Epichloë coenophiala* cloA for producing lysergol.
28. The method according to embodiments 25, 26, and 27, set forth above, including amplifying said easA and cloA based on degenerate primers designed to anneal to versions of each gene.
29. A method for producing dihydrolysergic acid comprising expressing *C. africana* cloA under the control of a *A. fumigatus* easA promoter in *A. fumigatus* easM knock-out strain for producing dihydrolysergic acid.
30. A method for producing dihydrolysergic acid comprising expressing *C. africana* easA, *C. africana* cloA, and *E.* sp. Lp1 cloA using a *A. fumigatus* easA/easG promoter for producing dihydrolysergic acid.
31. A method for producing dihydrolysergol comprising expressing *C. gigantea* cloA in *A. fumigatus* easM knock-out for producing dihydrolysergol.
32. The method of embodiment 31 set forth above, including joining said cloA to a easA promoter of *A. fumigatus* to form a cloA construct and introducing said cloA construct into *A. fumigatus* easM knock-out utilizing cotransformation with pBCphleo.
33. The method of embodiment 32 set forth above, including adding a *C. gigantea* easA expressed from a *A. fumigatus* easA promoter to said cotransformation of the *A. fumigatus* easM knockout.
34. A strain of fungus comprising SEQ ID NO:4.
35. A strain of fungus comprising SEQ ID NO: 7.

Production of Lysergic Acid by Genetic Modification of an Industrially Relevant Fungus The following pages set forth the following:

*Aspergillus fumigatus* easA; *Epichloë festucae* var. *lolii*×*Epichloë typhina* isolate Lp1 easA; *Epichloë festucae* var. *lolii*×*Epichloë typhina* isolate Lp1 cloA; *Aspergillus fumigatus* ergot alkaloid pathway;

Dual-gene transformation construct to express easA and cloA from *Epichloë festucae* var. *lolii*×*Epichloë typhina* isolate Lp1 in *Aspergillus fumigatus*; Recipient strain *Aspergillus fumigatus* easA knockout description; and Details of disarmed strain of *Aspergillus fumigatus*.

*Aspergillus fumigatus* easA
Nucleotide sequence
(coding sequence, which for this gene naturally lacks introns)
ATGCGAGAAGAACCGTCCTCTGCTCAGCTATTCAAGCCGCTCAAGGTGGGAAGATGTCATCTCCAACATAGGATGAT

CATGGCGCCGACAACTCGATTCCGGGCCGATGGACAGGGGGTCCCGCTTCCTTTTGTACAAGAGTATTACGGTCAGC

GTGCATCGGTTCCTGGCACCCTCCTCATCACCGAAGCAACAGACATCACCCCCAAGGCGATGGGTTACAAACATGTC

CCGGGGATATGGAGTGAGCCGCAGCGCGAGGCGTGGAGAGAGATTGTTTCTAGAGTCCATTCGAAAAAATGCTTTAT

TTTCTGCCAGTTATGGGCGACCGGCCGCGCCGCAGATCCGGACGTACTCGCCGACATGAAGGACCTGATCTCTAGTA

GCGCCGTGCCTGTAGAAGAGAAGGGACCTCTTCCCCGAGCTCTGACTGAGGACGAAATCCAGCAGTGCATCGCAGAT

TTTGCGCAGGCGGCCCGAAACGCCATCAATGCTGGGTTCGATGGGGTGGAGATCCATGGTGCCAATGGGTACCTCAT

CGACCAGTTCACACAGAAGTCTTGCAACCACCGCCAGGATCGATGGGGCGGAAGCATCGAGAATCGAGCTCGTTTTG

CGGTCGAGGTAACACGGGCGGTTATCGAGGCCGTGGGTGCCGATCGTGTCGGCGTCAAACTCTCCCCCTACAGTCAG

TATCTGGGGATGGGAACAATGGACGAGCTTGTGCCACAGTTTGAGTATCTCATTGCCCAGATGCGGCGATTGGATGT

CGCATATCTCCATCTTGCCAACTCCCGATGGCTTGATGAGGAAAAGCCCCATCCTGACCCTAATCATGAGGTGTTTG

TGCGTGTCTGGGGTCAATCCTCACCTATCCTGCTGGCAGGCGGGTATGATGCGGCATCGGCAGAGAAGGTGACGGAG

CAGATGGCGGCAGCGACTTACACCAATGTGGCCATTGCTTTTGGGAGGTACTTTATCTCGACTCCAGACCTGCCCTT

TCGGGTCATGGCTGGCATCCAGCTTCAAAAGTACGATCGTGCCTCTTTCTATAGCACGCTATCAAGAGAAGGCTACC

TTGATTACCCTTTCAGCGCTGAATATATGGCATTGCATAATTTCCCCGTCTAA

GenBank: XM_751040.1
Amino acid sequence (deduced from above)
MREEPSSAQLFKPLKVGRCHLQHRMIMAPTTRFRADGQGVPLPFVQEYYGQRASVPGTLLITEATDITPKAMGYKHV

PGIWSEPQREAWREIVSRVHSKKCFIFCQLWATGRAADPDVLADMKDLISSSAVPVEEKGPLPRALTEDEIQQCIAD

FAQAARNAINAGFDGVEIHGANGYLIDQFTQKSCNHRQDRWGGSIENRARFAVEVTRAVIEAVGADRVGVKLSPYSQ

YLGMGTMDELVPQFEYLIAQMRRLDVAYLHLANSRWLDEEKPHPDPNHEVFVRVWGQSSPILLAGGYDAASAEKVTE

QMAAATYTNVAIAFGRYFISTPDLPFRVMAGIQLQKYDRASFYSTLSREGYLDYPFSAEYMALHNFPV

*Epichloë* festucae var. *lolii* × *Epichloë* typhina isolate Lp1 easA

Note on the name of the fungus

Genes easA and cloA were cloned from the fungus "*Epichloë* festucae var. *lolii* × *Epichloë* typhina isolate Lp1". This is one name for a single fungus with a hybrid origin; thus, the apparent multiple names within a long name. In the original disclosure, the fungus was called *Neotyphodium lolii* × *Epichloë* typhina isolate Lp1. After we submitted that disclosure, the fungus was renamed *Epichloë* festucae var. *lolii* × *Epichloë* typhina isolate Lp1.

Nucleotide sequence (coding sequence, which for this gene naturally lacks introns)
ATGTCAACTTCAAATCTTTTCACGCCGCTCCAATTTGGAAAATGTCTCCTCCAGCACAAGCTAGTCCTCTCACCGAT

GACTCGTTTTCGTGCGGATAATGAAGGCGTCCCGCTTCCCTATGTCAAGACTTACTACTGTCAACGAGCATCTCTCC

CTGGCACCCTGCTTCTTACCGAAGCTACTGCCATCTCTCGCCGAGCCAGAGGGTTTCCCAATGTCCCCGGGATTTGG

AGTCAGGAGCAAATTGCAGGCTGGAAAGAGGTAGTTGATGCTGTGCATGCGAAGGGGTCTTATATCTGGCTGCAGCT

TTGGGCGACTGGACGAGCAGCCGAGGTTGGTGTTCTGAAAGCGAATGGATTTGATCTCGTATCCAGCAGTGCCGTTC

CAGTCTCCCCCGGTGAGCCCACACCCCGGGCGCTCAGCGACGATGAGATCAACTCATACATCGGTGATTTCGTTCAA

GCAGCCAAAAATGCAGTCCTAGAAGCAGGATTTGACGGAGTCGAACTCCACGGTGCCAATGGATTTCTCATCGATCA

GTTTCTCCAATCTCCTTGCAACCAACGTACCGATCAATGGGCGGTTGCATTGAGAATCGCTCACGGTTCGGTCTTG

AAATCACCCGGCGAGTCATCGACGCTGTCGGTAAAGACCATGTGGGCATGAAGCTTTCCACTTGGAGTACCTTCCAG

GGAATGGGCACCATGGACGACCTCATACCTCAGTTCGAGCATTTCATCATGCGCCTTCGTGAGATAGGCATTGCCTA

TCTACACCTTGCTAACTCTCGCTGGGTAGAGGAGGAAGACCCCACCATCAGAACACATCCAGATATTCATAATGAGA

-continued

```
CTTTTGTGCGCATGTGGGGGAAAGAGAAGCCTGTCCTTTTGGCTGGTGGCTACGGCCCGGAGTCCGCCAAGCTTGTG

GTAGATGAAACATACTCTGACCACAAGAACATCGGTGTCGTTTTTGGACGACACTATATATCCAACCCAGATCTTCC

ATTCCGGCTGAAAATGGGACTCCCTCTTCAAAAGTACAATCGGGAAACTTTCTACATTCCGTTCTCTGACGAGGGAT

ACTTGGATTACCCCTATAGTGAGGAATACATAACAGAGAACAAGAAGCAGGCAGTTCTAGCATAA
```

GenBank: KC989613.1
Amino acid sequence (deduced from above)

```
MSTSNLFTPLQFGKCLLQHKLVLSPMTRFRADNEGVPLPYVKTYYCQRASLPGTLLLTEATAISRRARGFPNVPGIW

SQEQIAGWKEVVDAVHAKGSYIWLQLWATGRAAEVGVLKANGFDLVSSSAVPVSPGEPTPRALSDDEINSYIGDFVQ

AAKNAVLEAGEDGVELHGANGFLIDQFLQSPCNQRTDQWGGCIENRSRFGLEITRRVIDAVGKDHVGMKLSTWSTFQ

GMGTMDDLIPQFEHFIMRLREIGIAYLHLANSRWVEEEDPTIRTHPDIHNETFVRMWGKEKPVLLAGGYGPESAKLV

VDETYSDHKNIGVVFGRHYISNPDLPFRLKMGLPLQKYNRETFYIPFSDEGYLDYPYSEEYITENKKQAVLA
```

*Epichloë* festucae var. *lolii* × *Epichloë* typhina isolate Lp1 cloA

Nucleotide sequence (coding sequence with introns)
```
ATGATATTACCATGGTTATCCCAGCTTCAATCGGTCTCACTAGGGACGATTTTCCTCACGCTATTCCTCGTTATATT

GACTCCTTTGGTTTTCACAAGCGTTTACCGTCTGTATTTTCATCCTCTTCGCAAAATTCCTGGACCACGAACCGGGG

GTTTGACAAGTTTCTATGGGTTCTATTGGAACTGGATACGAGATGAAGGATACTCTAAGCTCTTCAATCCCCTGCAT

AAACAATATAGTAAGGTTTATTTCCCGAATAAATACCCCTTGTGAATGCTAAGATGCATCAAGATTCCCATATCATA

CGTATCGGCCCAAACCATGTTCACATCAACCAACCGCAAGCTTTTGATGAGTTCGTACAAGACTCCTCTACACTTCT

AAACTGTGGAGGGCTCACACAAATAAAAATTAGGATATTCAAAGTTGGAACAACATGGCGCAAAGACAGCTCATTTT

ACAAGTATTTTAACGGCTTGGACGCCATGATTGAGCCGACGCAATATCGCACCTACCGAACTCACTTGGCCCCTTTA

TACGCACAACGCTCCATTGATGGCTTAACACCAAAGCTCCATGACGACCTCGTGGTAACTGCCGAAAGGATGGCCAA

GAGCATCGAAAATGGTGAACCTGTGAACATGGTGAAGATATTGCGGACATTGAGTGTAAGTATATAGTGGTTGTTCA

AAAACCACTGTATTTCGACTAACGGCCAACGGGAATAGACCTCAATGATGCTTTATACTTTGTATTCGCAGGACATC

CCGCTCTCTCAATATGATGGGTATCACCCGTTTCTAGAAGCTTTTGAGCTGCTCATGACCCAAAGTTGGCTAAGTGA

GTCTGTATCACATTTCAGGTCACAGTTTGCTTTATTGTATACAGGAACGCTGATAATTTGTTTCTGTACAAAGTGAT

CAATTATCCCATGATGGGTATGATCCTTGGCCTAATTCCCGGCACGAGCTTTGCGAAATTCAATGCCGCTTTCGGAA

CCTTCTTGAAGGTTAGTTAACTTGCGGAGTAACAAGGGACAAAGCACACAAATTGCTAAAAGAATGTTAATTTACAG

TACTGTAAAGAGTGGAACGACGAGGATGAACGCATTCAAAAGCTTGAAACTGCTGAATCACTGCGGGACTCCCACAT

GAAACGATACCTTGCCATTGACCCAAATAACGAGATCAAAAAGAAGGTCGTGCCGCATCCCCTGGAGGATATATTTA

ACTTTATCGCAGGCGGTAGTGACACTACTTCATATACAGCTGCATGTGCATTCTTCCATGTTCTCTCGTCGTCTGAG

GTGCACTCTAAGCTCGTGGCGGAGCTCGATCAAGCTTCTTCAGTGATCAGGGATACCTTTGATTACAATAAGATTCA

AAACTTGCCATATCTGGTGTGTATACGATTAAGAGTTTACCTATCATCATTTTTCCCGGACCCTCTTCTGAAAGTAG

GCTCTAACCATGGATGTTGCAGAATGCCGTGATCAAGGAGACGCTTCGTATCTCTTGTCCGGTACCAGGGTGTCTTC

CCCGAGTCGTCCCTGAGGGGGGAATGAATCTGGGTTCAGTAAATCTTCCAGCCGGTGTAAGCTCCATTTATACAACC

TTGTATAAGACTAGTGACTTGCTAACGTTGTGATATGCGAACAGACAGTGGTGTCAATCTCCCAGCTAGCCATCCAC

TTTAATGAGACGATTTTCTCGTCACCTGACAAGTTCATCCCCGAAAGATGGCTTGGGGACGATAGAAAATCGATTGA

GAAGTGGAATATCGCTTTTAGCAGAGGACCTCGACAGTGCATTGGGACAACGTAAGTCTTCCCCCCCCCCCGATCCG

GTGATAGTATCAAAATACCACCATTCTCTGCTATTGTAGATGAATGAATGCTGAGTTTTAACGTTTTTTGTTCCATA

GTCTCGCTTATATGGAACTACGCTGCGTCCTCGCTTATTTCTTCTCCCGCTTTGAATTTAAGTTAACGGGTAGCTGT

GGAGATAAGTTGCGCTGGGTTGATCGATTTGTCTCAGTCAACTTGGACGATGTCGAGGTCACTATCGTGAAGGACCG

ATGGGCGTAA
```

GenBank: KC989583.1
Amino acid sequence (deduced from above)
MILPWLSQLQSVSLGTIFLTLFLVILTPLVFTSVYRLYFHPLRKIPGPRTGGLTSFYGFYWNWIRDEGYSKLFNPLH

KQYNSHIIRIGPNHVHINQPQAFDEIFKVGTTWRKDSSFYKYFNGLDAMIEPTQYRTYRTHLAPLYAQRSIDGLTPK

LHDDLVVTAERMAKSIENGEPVNMVKILRTLSTSMMLYTLYSQDIPLSQYDGYHPFLEAFELLMTQSWLMINYPMMG

MILGLIPGTSFAKFNAAFGTFLKYCKEWNDEDERIQKLETAESLRDSHMKRYLATDPNNEIKKKVVPHPLEDIFNFI

AGGSDTTSYTAACAFFHVLSSSEVHSKLVAELDQASSVIRDTFDYNKIQNLPYLNAVIKETLRISCPVPGCLPRVVP

EGGMNLGSVNLPAGTVVSISQLAIHFNETIFSSPDKFIPERWLGDDRKSIEKWNIAFSRGPRQCIGTTLAYMELRCV

LAYFFSRFEFKLTGSCGDKLRWVDRFVSVNLDDVEVTIVKDRWA

15

The *Aspergillus fumigatus* ergot alkaloid pathway is set forth in FIG. 14. Ergot alkaloid pathway of *Aspergillus fumigatus*. Roles for genes are indicated between intermediates or products. Double arrow indicates one or more uncharacterized intermediates: DMAPP, dimethylallylpyrophosphate; DMAT, dimethylallyltryptophan; Trp, tryptophan.

Figure 8:
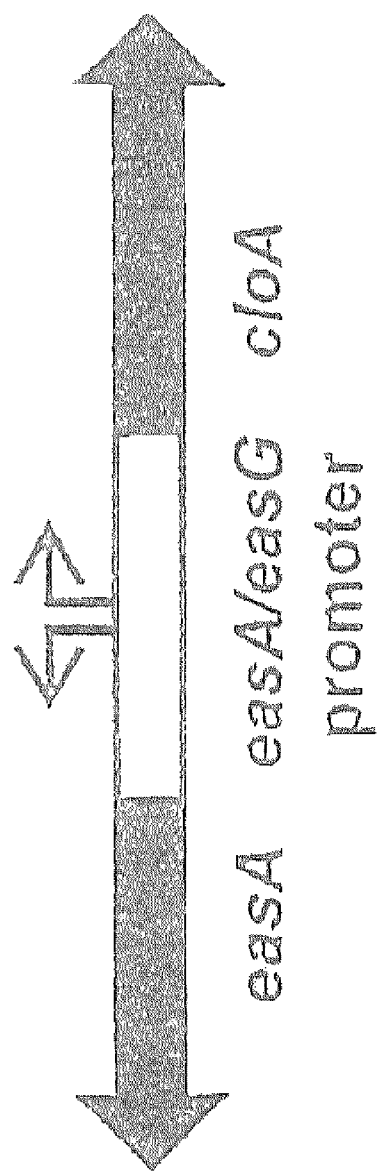

FIG. 8 shows Dual-gene transformation construct (construct corresponding to SEQ ID NO:4) to express easA and cloA from *Epichloë festucae* var. *loliix*Epichloë typhina* isolate Lp1 in *Aspergillus fumigatus*. The coding sequences and 3' untranslated sequences from easA and cloA were joined divergently and at alternate ends of the bidirectional easA/easG promoter from *Aspergillus fumigatus* (GenBank: NC_007195.1). The construct was prepared by fusion PCR, and the sequence of the completed construct is provided below (in a manner that corresponds to the diagram set forth in FIG. 8). The first shaded portion corresponds to the reverse complement of the *Epichloë festucae* var. *loliix Epichloë typhina* isolate Lp1 easA sequence (including 264 by of 3' untranslated sequence), the central, unshaded portion is the *Aspergillus fumigatus* promoter, and the second shaded portion is the *Epichloë festucae* var. *loliix*Epichloë typhina* isolate Lp1 cloA sequences (including 634 by of 3' untranslated sequence).

```
CGTATCACCGAGACAAAGAGGCGCATCATTCACTATCAATTATTTTCAGAGATATCTAAATGAAACAAAATGACTAC

AGTATTGTATAATGATCACGGAGCACCAAAGACTAAGAAGACAATGATAAAGATAACTTAATGAACGAAATACAAAA

GCCATACCACACTAGTGTACCTATTCGGTATAAGATTTAACTCTTAGAGGAATCATTTATAAGGCTAATCCAAAAGA

ATGCAAAAGCATTGCCTGGACTGCGATAATGATTTATGCTAGAACTGCCTGCTTCTTGTTCTCTGTTATGTATTCCT

CACTATAGGGGTAATCCAAGTATCCCTCGTCAGAGAACGGAATGTAGAAAGTTTCCCGATTGTACTTTTGAAGAGGG

AGTCCCATTTTCAGCCGGAATGGAAGATCTGGGTTGGATATATAGTGTCGTCCAAAAACGACACCGATGTTCTTGTG

GTCAGAGTATGTTTCATCTACCACAAGCTTGGCGGACTCCGGGCCGTAGCCACCAGCCAAAAGGACAGGCTTCTCTT

TCCCCCACATGCGCACAAAAGTCTCATTATGAATATCTGGATGTGTTCTGATGGTGGGGTCTTCCTCCTCTACCCAG

CGAGAGTTAGCAAGGTGTAGATAGGCAATGCCTATCTCACGAAGGCGCATGATGAAATGCTCGAACTGAGGTATGAG

GTCGTCCATGGTGCCCATTCCCTGGAAGGTACTCCAAGTGGAAAGCTTCATGCCCACATGGTCTTTACCGACAGCGT

CGATGACTCGCCGGGTGATTTCAAGACCGAACCGTGAGCGATTCTCAATGCAACCGCCCCATTGATCGGTACGTTGG

TTGCAAGGAGATTGGAGAAACTGATCGATGAGAAATCCATTGGCACCGTGGAGTTCGACTCCGTCAAATCCTGCTTC

TAGGACTGCATTTTTGGCTGCTTGAACGAAATCACCGATGTATGAGTTGATCTCATCGTCGCTGAGCGCCCGGGGTG

TGGGCTCACCGGGGGAGACTGGAACGGCACTGCTGGATACGAGATCAAATCCATTCGCTTTCAGAACACCAACCTCG

GCTGCTCGTCCAGTCGCCCAAAGCTGCAGCCAGATATAAGACCCCTTCGCATGCACAGCATCAACTACCTCTTTCCA

GCCTGCAATTTGCTCCTGACTCCAAATCCCGGGGACATTGGGAAACCCTCTGGCTCGGCGAGAGATGGCAGTAGCTT

CGGTAAGAAGCAGGGTGCCAGGGAGAGATGCTCGTTGACAGTAGTAAGTCTTGACATAGGGAAGCGGGACGCCTTCA

TTATCCGCACGAAAACGAGTCATCGGTGAGAGGACTAGCTTGTGCTGGAGGAGACATTTTCCAAATTGGAGCGGCGT

GAAAAGATTTGAAGTTGACATTGCTTCTAATCCACCAAGTACTTGGAACACGGTGAATGTCGAAGCTCAGTCTGACC

AGTGGAGGTATCGACGCGAACTTTTCAGGTCATGGAAGTGTGGAGTATGGTCTACAGGCTTGGAGGACTTTGTATTG
```

-continued

```
ATTCTGGCATCGATAACTGAGCAGACAAGACGCCATTCGGGCACAATTTCTTTCTGCTGGACAATTCTCATACAGCC
ATGTCGTCCCCCTTGCCGAGCCAACGCCACTATTTGTTTATGTGTCTATTATTCGATATTCACGGGGAAAGGTGAGC
TGACTTGTACGTACTCTGTCTACTCCAATGCCCTCACCTTTCTTCAGCTGCAGAGCCGTGGAGCGGAACTCCTTGCT
TCCCCGTTTACATACTTGGGAATTGAAATCAGGACCCATATCTCCATGACGAGTCTTTTATCATGCACATGGGAAAT
GGCGGTCAGTTAAAACATGATCAATACTACTGTTACGCCTTTACTCCAATGCACCGATAGCTAATAAGAAGAGCTCC
TCCACCCTCCCACAAAGAGGCAAGGGAGAGCCAGAAGAGACTGAGGGTGGTGGGCGAAAACAGCTCCAAGCGTATAT
GTGCTACTGTGCCCAAGACTTCACCGTACTTTCTCAATGTGTGAATAATGAGGACTAGACGAGACACTCTTAATAAG
AGATCATCTACCAGAAAGGGCGTACGTTACTACCAAACTCTGTGTGATTAAATGTACACACATTCTTTCAACAAACA
AATTTGATCCATCTTCTATAGAGTAGGCACTCCGCACCATGATATTACCATGGTTATCCCAGCTTCAATCGGTCTCA
CTAGGGACGATTTTCCTCACGCTATTCCTCGTTATATTGACTCCTTTGGTTTTCACAAGCGTTTACCGTCTGTATTT
TCATCCTCTTCGCAAAATTCCTGGACCACGAACCGGGGGTTTGACAAGTTTCTATGGGTTCTATTGGAACTGGATAC
GAGATGAAGGATACTCTAAGCTCTTCAATCCCCTGCATAAACAATATAGTAAGGTTTATTTCCCGAATAAATACCCC
TTGTGAATGCTAAGATGCATCAAGATTCCCATATCATACGTATCGGCCCAAACCATGTTCACATCAACCAACCGCAA
GCTTTTGATGAGTTCGTACAAGACTCCTCTACACTTCTAAACTGTGGAGGGCTCACACAAATAAAAATTAGGATATT
CAAAGTTGGAACAACATGGCGCAAAGACAGCTCATTTTACAAGTATTTTAACGGCTTGGACGCCATGATTGAGCCGA
CGCAATATCGCACCTACCGAACTCACTTGGCCCCTTTATACGCACAACGCTCCATTGATGGCTTAACACCAAAGCTC
CATGACGACCTCGTGGTAACTGCCGAAAGGATGGCCAAGAGCATCGAAAATGGTGAACCTGTGAACATGGTGAAGAT
ATTGCGGACATTGAGTGTAAGTATATAGTGGTTGTTCAAAAACCACTGTATTTCGACTAACGGCCAACGGGAATAGA
CCTCAATGATGCTTTATACTTTGTATTCGCAGGACATCCCGCTCTCTCAATATGATGGGTATCACCCGTTTCTAGAA
GCTTTTGAGCTGCTCATGACCCAAAGTTGGCTAAGTGAGTCTGTATCACATTTCAGGTCACAGTTTGCTTTATTGTA
TACAGGAACGCTGATAATTTGTTTCTGTACAAAGTGATCAATTATCCCATGATGGGTATGATCCTTGGCCTAATTCC
CGGCACGAGCTTTGCGAAATTCAATGCCGCTTTCGGAACCTTCTTGAAGGTTAGTTAACTTGCGGAGTAACAAGGGA
CAAAGCACACAAATTGCTAAAAGAATGTTAATTTACAGTACTGTAAAGAGTGGAACGACGAGGATGAACGCATTCAA
AAGCTTGAAACTGCTGAATCACTGCGGGACTCCCACATGAAACGATACCTTGCCATTGACCCAAATAACGAGATCAA
AAAGAAGGTCGTGCCGCATCCCCTGGAGGATATATTTAACTTTATCGCAGGCGGTAGTGACACTACTTCATATACAG
CTGCATGTGCATTCTTCCATGTTCTCTCGTCGTCTGAGGTGCACTCTAAGCTCGTGGCGGAGCTCGATCAAGCTTCT
TCAGTGATCAGGGATACCTTTGATTACAATAAGATTCAAAACTTGCCATATCTGGTGTGTATACGATTAAGAGTTTA
CCTATCATCATTTTTCCCGGACCCTCTTCTGAAAGTAGGCTCTAACCATGGATGTTGCAGAATGCCGTGATCAAGGA
GACGCTTCGTATCTCTTGTCCGGTACCAGGGTGTCTTCCCCGAGTCGTCCCTGAGGGGGAATGAATCTGGGTTCAG
TAAATCTTCCAGCCGGTGTAAGCTCCATTTATACAACCTTGTATAAGACTAGTGACTTGCTAACGTTGTGATATGCG
AACAGACAGTGGTGTCAATCTCCCAGCTAGCCATCCACTTTAATGAGACGATTTTCTCGTCACCTGACAAGTTCATC
CCCGAAAGATGGCTTGGGGACGATAGAAAATCGATTGAGAAGTGGAATATCGCTTTTAGCAGAGGACCTCGACAGTG
CATTGGGACAACGTAAGTCTTCCCCCCCCCCCGATCCGGTGATAGTATCAAAATACCACCATTCTCTGCTATTGTAG
ATGAATGAATGCTGAGTTTTAACGTTTTTTGTTCCATAGTCTCGCTTATATGGAACTACGCTGCGTCCTCGCTTATT
TCTTCTCCCGCTTTGAATTTAAGTTAACGGGTAGCTGTGGAGATAAGTTGCGCTGGGTTGATCGATTTGTCTCAGTC
AACTTGGACGATGTCGAGGTCACTATCGTGAAGGACCGATGGGCGTAAGCTGAAAGCGTCCAAAAGTGCCCGGGAGG
```

-continued

```
CGTAGGCACGGCCAGAGGGATGTATCTTGACTTGGAGAAAATTAAGGGCGGGAAGCAAGTTAAACTAGGATCTTTCC

ATAGTACTATTTAATGAGCTAACCCTATGAAGTGTGAGGGGACAAGGGTATTAACGAGTTCAAATGCCGCTTACATA

TAGCGATTTTTCACGAGAGACAGAGATTCCTAAATGCCTTAGTTATATTAAGTAACTAAAAACTGTAACTTAAGCCT

CGCTAGTAATTGCACAATATTTATAAAGTGAGACATTTATCAAATATAAAAGCCACATCGTTCTTTTACGTGGAGCA

CATTTTAGGAGACATAGGGAAAGGTATAAGAGGGAACACTGTTACAGTATTCTCAGACTTTATAATAATAACAGTCA

ATGTTAGAGAAAATATATGGTTCTTTGAGATTTGTTAACACAGAGCCATTAAGACGTTGTTTAGGCAATGTCTTAAT

AGTGGTGAGTTACCGCGTAGTAATGTGCATGTATTTTAATTAGCCATAGCAGGCATACGTGCCTTTAGTTAGTTACT

TATGCTTATTGCTTACCTAAATACACGCCATACCTAACGCTTATCGCTTGTTGCCCTTAGCGTGTT
```

Recipient Strain *Aspergillus fumigatus* easA Knockout Description:

The *Aspergillus fumigatus* easA knockout mutant was prepared previously. The properties of the mutant are described in detail in the following publication: Coyle, C. M., Cheng, J. Z., O'Connor, S. E., Panaccione, D. G. 2010. An old yellow enzyme gene controls the branch point between *Aspergillus fumigatus* and *Claviceps purpurea* ergot alkaloid pathways. *Applied and Environmental Microbiology* 76:3898-3903.

Briefly, the coding sequence of *Aspergillus fumigatus* easA (unshaded below) was disrupted after nucleotide 777 of the 1131-nt coding sequence by insertion of a plasmid, pCR2.1 (shaded below) (product of Invitrogen, Life Technologies, Grand Island, N.Y.).

```
ATGCGAGAAGAACCGTCCTCTGCTCAGCTATTCAAGCCGCTCAAGGTGGGAAGATGTCATCTCCAACATAGGATGAT

CATGGCGCCGACAACTCGATTCCGGGCCGATGGACAGGGGGTCCCGCTTCCTTTTGTACAAGAGTATTACGGTCAGC

GTGCATCGGTTCCTGGCACCCTCCTCATCACCGAAGCAACAGACATCACCCCCAAGGCGATGGGTTACAAACATGTC

CCGGGGATATGGAGTGAGCCGCAGCGCGAGGCGTGGAGAGAGATTGTTTCTAGAGTCCATTCGAAAAAATGCTTTAT

TTTCTGCCAGTTATGGGCGACCGGCCGCGCCGCAGATCCGGACGTACTCGCCGACATGAAGGACCTGATCTCTAGTA

GCGCCGTGCCTGTAGAAGAGAAGGGACCTCTTCCCCGAGCTCTGACTGAGGACGAAATCCAGCAGTGCATCGCAGAT

TTTGCGCAGGCGGCCCGAAACGCCATCAATGCTGGGTTCGATGGGGTGGAGATCCATGGTGCCAATGGGTACCTCAT

CGACCAGTTCACACAGAAGTCTTGCAACCACCGCCAGGATCGATGGGGCGGAAGCATCGAGAATCGAGCTCGTTTTG

CGGTCGAGGTAACACGGGCGGTTATCGAGGCCGTGGGTGCCGATCGTGTCGGCGTCAAACTCTCCCCCTACAGTCAG

TATCTGGGGATGGGAACAATGGACGAGCTTGTGCCACAGTTTGAGTATCTCATTGCCCAGATGCGGCGATTGGATGT

CGCATATAGCGCCCAATACGCAAACCGCCTCTCCCCGCGCGTTGGCCGATTCATTAATGCAGCTGGCACGACAGGTT

TCCCGACTGGAAAGCGGGCAGTGAGCGCAACGCAATTAATGTGAGTTAGCTCACTCATTAGGCACCCCAGGCTTTAC

ACTTTATGCTTCCGGCTCGTATGTTGTGTGGAATTGTGAGCGGATAACAATTTCACACAGGAAACAGCTATGACCAT

GATTACGCCAAGCTTGGTACCGAGCTCGGATCCACTAGTAACGGCCGCCAGTGTGCTGGAATTCGGCTTAAGCCGAA

TTCTGCAGATATCCATCACACTGGCGGCCGCTCGAGCATGCATCTAGAGGGCCCAATTCGCCCTATAGTGAGTCGTA

TTACAATTCACTGGCCGTCGTTTTACAACGTCGTGACTGGGAAAACCCTGGCGTTACCCAACTTAATCGCCTTGCAG

CACATCCCCCTTTCGCCAGCTGGCGTAATAGCGAAGAGGCCCGCACCGATCGCCCTTCCCAACAGTTGCGCAGCCTG

AATGGCGAATGGGACGCGCCCTGTAGCGGCGCATTAAGCGCGGCGGGTGTGGTGGTTACGCGCAGCGTGACCGCTAC

ACTTGCCAGCGCCCTAGCGCCCGCTCCTTTCGCTTTCTTCCCTTCCTTTCTCGCCACGTTCGCCGGCTTTCCCCGTC

AAGCTCTAAATCGGGGGCTCCCTTTAGGGTTCCGATTTAGAGCTTTACGGCACCTCGACCGCAAAAAACTTGATTTG

GGTGATGGTTCACGTAGTGGGCCATCGCCCTGATAGACGGTTTTTCGCCCTTTGACGTTGGAGTCCACGTTCTTTAA
```

-continued

```
TAGTGGACTCTTGTTCCAAACTGGAACAACACTCAACCCTATCGCGGTCTATTCTTTTGATTTATAAGGGATTTTGC
CGATTTCGGCCTATTGGTTAAAAAATGAGCTGATTTAACAAATTCAGGGCGCAAGGGCTGCTAAAGGAACCGGAACA
CGTAGAAAGCCAGTCCGCAGAAACGGTGCTGACCCCGGATGAATGTCAGCTACTGGGCTATCTGGACAAGGGAAAAC
GCAAGCGCAAAGAGAAAGCAGGTAGCTTGCAGTGGGCTTACATGGCGATAGCTAGACTGGGCGGTTTTATGGACAGC
AAGCGAACCGGAATTGCCAGCTGGGGCGCCCTCTGGTAAGGTTGGGAAGCCCTGCAAAGTAAACTGGATGGCTTTCT
TGCCGCCAAGGATCTGATGGCGCAGGGGATCAAGATCTGATCAAGAGACAGGATGAGGATCGTTTCGCATGATTGAA
CAAGATGGATTGCACGCAGGTTCTCCGGCCGCTTGGGTGGAGAGGCTATTCGGCTATGACTGGGCACAACAGACAAT
CGGCTGCTCTGATGCCGCCGTGTTCCGGCTGTCAGCGCAGGGGCGCCCGGTTCTTTTTGTCAAGACCGACCTGTCCG
GTGCCCTGAATGAACTGCAGGACGAGGCAGCGCGGCTATCGTGGCTGGCCACGACGGGCGTTCCTTGCGCAGCTGTG
CTCGACGTTGTCACTGAAGCGGGAAGGGACTGGCTGCTATTGGGCGAAGTGCCGGGGCAGGATCTCCTGTCATCTCG
CCTTGCTCCTGCCGAGAAAGTATCCATCATGGCTGATGCAATGCGGCGGCTGCATACGCTTGATCCGGCTACCTGCC
CATTCGACCACCAAGCGAAACATCGCATCGAGCGAGCACGTACTCGGATGGAAGCCGGTCTTGTCGATCAGGATGAT
CTGGACGAAGAGCATCAGGGGCTCGCGCCAGCCGAACTGTTCGCCAGGCTCAAGGCGCGCATGCCCGACGGCGAGGA
TCTCGTCGTGATCCATGGCGATGCCTGCTTGCCGAATATCATGGTGGAAAATGGCCGCTTTTCTGGATTCAACGACT
GTGGCCGGCTGGGTGTGGCGGACCGCTATCAGGACATAGCGTTGGATACCCGTGATATTGCTGAAGAGCTTGGCGGC
GAATGGGCTGACCGCTTCCTCGTGCTTTACGGTATCGCCGCTCCCGATTCGCAGCGCATCGCCTTCTATCGCCTTCT
TGACGAGTTCTTCTGAATTGAAAAAGGAAGAGTATGAGTATTCAACATTTCCGTGTCGCCCTTATTCCCTTTTTTGC
GGCATTTTGCCTTCCTGTTTTTGCTCACCCAGAAACGCTGGTGAAAGTAAAAGATGCTGAAGATCAGTTGGGTGCAC
GAGTGGGTTACATCGAACTGGATCTCAACAGCGGTAAGATCCTTGAGAGTTTTCGCCCCGAAGAACGTTTTCCAATG
ATGAGCACTTTTAAAGTTCTGCTATGTCATACACTATTATCCCGTATTGACGCCGGGCAAGAGCAACTCGGTCGCCG
GGCGCGGTATTCTCAGAATGACTTGGTTGAGTACTCACCAGTCACAGAAAAGCATCTTACGGATGGCATGACAGTAA
GAGAATTATGCAGTGCTGCCATAACCATGAGTGATAACACTGCGGCCAACTTACTTCTGACAACGATCGGAGGACCG
AAGGAGCTAACCGCTTTTTTGCACAACATGGGGGATCATGTAACTCGCCTTGATCGTTGGGAACCGGAGCTGAATGA
AGCCATACCAAACGACGAGAGTGACACCACGATGCCTGTAGCAATGCCAACAACGTTGCGCAAACTATTAACTGGCG
AACTACTTACTCTAGCTTCCCGGCAACAATTAATAGACTGGATGGAGGCGGATAAAGTTGCAGGACCACTTCTGCGC
TCGGCCCTTCCGGCTGGCTGGTTTATTGCTGATAAATCTGGAGCCGGTGAGCGTGGGTCTCGCGGTATCATTGCAGC
ACTGGGGCCAGATGGTAAGCCCTCCCGTATCGTAGTTATCTACACGACGGGGAGTCAGGCAACTATGGATGAACGAA
ATAGACAGATCGCTGAGATAGGTGCCTCACTGATTAAGCATTGGTAACTGTCAGACCAAGTTTACTCATATATACTT
TAGATTGATTTAAAACTTCATTTTTAATTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGATCAAAGGATCTTCTTGAGATCCTTTTT
TTCTGCGCGTAATCTGCTGCTTGCAAACAAAAAAACCACCGCTACCAGCGGTGGTTTGTTTGCCGGATCAAGAGCTA
CCAACTCTTTTTCCGAAGGTAACTGGCTTCAGCAGAGCGCAGATACCAAATACTGTCCTTCTAGTGTAGCCGTAGTT
AGGCCACCACTTCAAGAACTCTGTAGCACCGCCTACATACCTCGCTCTGCTAATCCTGTTACCAGTGGCTGCTGCCA
GTGGCGATAAGTCGTGTCTTACCGGGTTGGACTCAAGACGATAGTTACCGGATAAGGCGCAGCGGTCGGGCTGAACG
GGGGGTTCGTGCACACAGCCCAGCTTGGAGCGAACGACCTACACCGAACTGAGATACCTACAGCGTGAGCATTGAGA
```

```
-continued
AAGCGCCACGCTTCCCGAAGGGAGAAAGGCGGACAGGTATCCGGTAAGCGGCAGGGTCGGAACAGGAGAGCGCACGA

GGGAGCTTCCAGGGGGAAACGCCTGGTATCTTTATAGTCCTGTCGGGTTTCGCCACCTCTGACTTGAGCGTCGATTT

TTGTGATGCTCGTCAGGGGGCGGAGCCTATGGAAAAACGCCAGCAACGCGGCCTTTTTACGGTTCCTGGCCTTTTG

CTGGCCTTTTGCTCACATGTTCTTTCCTGCGTTATCCCCTGATTCTGTGGATAACCGTATTACCGCCTTTGAGTGAG

CTGATACCGCTCGCCGCAGCCGAACGACCGAGCGCAGCGAGTCAGTGAGCGAGGAAGCGGAAGCTCCATCTTGCCAA

CTCCCGATGGCTTGATGAGGAAAAGCCCCATCCTGACCCTAATCATGAGGTGTTTGTGCGTGTCTGGGGTCAATCCT

CACCTATCCTGCTGGCAGGCGGGTATGATGCGGCATCGGCAGAGAAGGTGACGGAGCAGATGGCGGCAGCGACTTAC

ACCAATGTGGCCATTGCTTTTGGGAGGTACTTTATCTCGACTCCAGACCTGCCCTTTCGGGTCATGGCTGGCATCCA

GCTTCAAAAGTACGATCGTGCCTCTTTCTATAGCACGCTATCAAGAGAAGGCTACCTTGATTACCCTTTCAGCGCTG

AATATATGGCATTGCATAATTTCCCCGTCTAA
```

Description of Disarming Mutation in the alb1 Gene of *Aspergillus fumigatus*

Nucleotides 1,278 through 2,705 of the 6,662-bp coding sequence of the alb1 gene of *Aspergillus fumigatus* (Gen-Bank: XP_756095.1) were deleted by homologous recombination with a construct designed as illustrated. The replacement of 1,427 by of alb1 sequences with any sequences would create a similar knockout mutation. Successful knockout of the alb1 gene results in an albino fungus (whereas the wild type is dark gray-green) and a loss of virulence as experimentally demonstrated by Tsai et al. (1998). Tsai, H. F., Chang, Y. C., Washburn, R. G., Wheeler, M. H., and Kwon-Chung, K. J. 1998. The developmentally regulated alb1 gene of *Aspergillus fumigatus*: Its role in modulation of conidial morphology and virulence. Journal of Bacteriology 180:3031-3038.

Nucleotide sequence of the alb1 gene of *Aspergillus fumigatus*
(required for melanin biosynthesis)

SEQ ID NO: 6

ATGGAGGATCTCCATCGCCTCTATCTCTTTGGAGATCAGACAATCAGCTGTGACGAAGGCCTCCGCAACCTCTTGCA

GGCGAAGAACCATACTATCGTCGCCTCGTTCATCGAAAGATGCTTCCATGCACTGCGTCAGGAAATCACCAGGCTGC

CGCCTTCTCAGCGCACGCTCTTCCCGCGGTTTACCAGCATCGCCGACTTGCTTGCTCAGCATCGTGAGTCAGGGACA

AACCCTGCGCTGGGGAGCGCGCTGACCTGTATCTATCAACTGGGGTGTTTCATCGAGTAAGTCGCCTTGCAAGGTAT

TCTGGACTGTGGCTGATCCTGGATAGTTACCACGGTGATCGTGGACATCCATATCCGTCCTCGGATGACGGCCTTCT

GGGTTCATGTACGGGTATGTTGAGTTGCACCGCAGTCAGCTCGTGCAAGAATGTCGGAGAACTACTGCCGCTGGCAG

TCGAGATTGTCAGATTGACTATCCACCTCGGGCTCTGTGTCATGAGAGTCCGAGAGATGGTGGACTCGACGGAGTCA

TCCTCCGGCAGCTGGTCAATCCTCGTCTCGGAGATCAACGAGGCAGATGCCACCAGCCTGATTGGCAATTTTGTCAA

GAAGCGAGTAAGTACAGTGTACGACCATTGGAAGAAGAATATTGACAATACCAGGGAATTCCCCCCTCGTCGCAACC

GTACATCAGCGCGGTTGGATCGAAAGGTCTCACCATCAGTGCACCACCCGAAATTCTCGACAACTTTATCGAAGAAG

GTCTTCCGAAGGAGTACAAACACTTCAAGGCTCCTGGAGTCAGTGGTCCGTACCACGCGCCCCATCTGTACAATGAC

CGAGAAATTCGCAATATCCTCAGCTTCTGCTCCGAGGACGTGATTCTGCGCCACACACCACGGGTTCCACTGGTCTC

GAGCAACACAGGGAAGCTGGTCCAGGTAAAGAGCATGCGTGATCTGCTAAAGGTGGCTCTGGAGGAAATCCTCTTGC

GCAAGATCTGCTGGGACAAAGTCACCGAGTCATGCCTTTCCATCGTTCAGGCTACCAACGACAAGCCCTGGAGGATT

CTCCCTATCGCCAGCAACGCCACGCAAGGCTTGGTTACTGCACTCCAGCGTATGGGAAACTGCCAGATCGAGGTAGA

CACCGGGGTCGGCGCTCCTCAAATGGACCCGGCCGCTCCCAATGCAACGGGCAATGCTTCACGGTCTAAGATCGCCA

TCATCGGAATGTCTGGGCGGTTCCCTGAGGCAGATGGTATCGAGGCCTTTTGGGACTTGTTGTATAAAGGTCTGGAT

GTTCACAAAAAGGTCCCACCTGAGCGATGGGATGTGGACGCGCACGTGGACTTGACCGGCACAAAGAGAAACACCAG

CAAGGTCCCATACGGTTGCTGGATCAACGAGCCCGGCCTGTTCGATGCCCGTTTCTTCAACATGTCTCCTCGGGAAG

CACTCCAGGCAGACCCTGCGCAGCGACTGGCGCTGCTGTCGGCTTACGAGGCCCTGGAAATGGCAGGCTTCGTTCCG

AACAGCAGTCCATCGACTCAGAGAGACCGCGTCGGCATCTTCATGGGTATGACCAGCGACGACTACCGTGAGATCAA

CAGCGGTCAGGATATCGACACATACTTCATTCCTGGAGGGAACCGAGCATTCACGCCTGGTCGTATCAACTACTACT

-continued

```
TCAAGTTCAGTGGGCCTAGTGTCAGTGTCGACACCGCCTGCTCGTCCAGTCTTGCTGCCATCCACTTGGCCTGCAAC
GCCATCTGGAGGAATGACTGCGATACCGCCATCAGTGGTGGTGTAAACCTCCTTACTAACCCGGACAACCATGCCGG
TCTGGATCGCGGCCACTTTCTGTCTCGGACAGGAAACTGCAACACCTTCGACGACGGCGCGGATGGCTACTGCCGGG
CGGACGGGGTGGGCACGATCGTCCTGAAGCGCCTGGAGGATGCTGAGGCTGACAACGATCCCATTCTGGGAGTCATT
AACGCGGCCTACACCAACCACTCGGCCGAAGCCGTCTCCATTACCCGCCCTCACGTCGGCGCGCAGGCGTTCATCTT
CAACAAGCTCCTCAACGACACCAACACCAACCCACACGAGATTGGCTACGTGGAAATGCACGGAACAGGTACTCAGG
CGGGCGACGCCGTTGAGATGCAGTCCGTCCTCGACGTCTTCGCACCCGACTACCGCCGGGCCGGCCAATTCCCTT
TATCTGGGTTCCGCCAAATCGAACATCGGCCACGGGGAATCAGCTTCCGGAGTGACATCCTTGGTCAAGGTCCTGTT
GATGTTGAAGCAGAACATGATCCCGCCCCACTGCGGAATCAAAACAAAGATCAATCACAACTTCCCCACGGATCTGG
CCCAGCGCAATGTCCATATTGCCTTCAAGCCAACCCCCTGGAACAGACCGGTCTCGGGCAAGCGGAAGATGTTCATC
AACAACTTCTCTGCTGCGGGCGGCAACACCGCTCTCCTGATGGAAGATGCCCCCCTGCGTGAGATCACAGGGCAGGA
TCCCCGGAATGTGCATGTGGTGTCTGTGACGGCACGGTCGCAGACTGCGCTGAAGCGTAACATCAACGCGTTGATCA
AGTACATCAACACGCATGCGCCCTCGTCGCCGGCGAATGAGCGACGGTTCCTGGCCAGTCTGGCTTATACTACTACC
GCGCGTCGCATGCATCACCCCTTCAGGGTCACCGCAGTGGGGTCGAGCGTGAAGGATATCCGGGAGGTCCTGCGTCA
ACGTGCCGATCAGGATGTCACCACCCCCGTCCCTGCGACAGCCCCCAAGACTGGGTTCGTCTTCACCGGTCAGGGAG
CTCAGTACACAGGGATGGGCAAGCAATTGTACGAGGACTGTGCCACATTCAGAAGCACGATTCACCGACTCGATTGC
ATTGCTCAAAGCCAAGGGTTCCCCTCCATTCTACCGTTGATTGACGGTAGTATGCCTGTGGAAGAACTGAGCCCTGT
CGTGACCCAGCTAGGAACCACATGCCTGCAGATGGCTCTGGTCGACTACTGGAAGGGTCTTGGTGTCACTCCTGCGT
TTGTTCTGGGACATAGTCTGGGAGACTACGCAGCGTTGAACAGTGCGGGCGTCTTGTCCACCAGCGATACGATTTAC
CTCTGTGGCCGTCGCGCGCAGCTTCTCACGCAGCAGTGTCAGATGGGGACCCACGCCATGCTTGCCGTCAAGGCTGC
CGTCTCCGAGATTCAACATCTGCTCGATCCAGACGTCCACGCCGTCGCCTGCATCAATGGACCAACCGAAACGGTCA
TCAGCGGGCTCAGCGGTCGAATCGATGAATTGGCACAGCAGTGCTCCAGCCAAAATCTCAAGTCCACCAAGCTCAAA
GTGCCGTTCGCGTTCCACTCGGCCCAAGTGGACCCGATTCTCGAGTCGTTCGAAGAGAGTGCTCAGGGGGTCATCTT
CCACGAACCTGCCGTCCCGTTCGTCTCTGCTCTGAACGGAGAGGTAATCACGGAGTCGAACTACAGCGTGCTGGGCC
CCACGTATATGGTGAAGCATTGTCGGGAAGCCGTCAATTTCCTTGGCGCTCTTGAGGCGACCCGGCACGCCAAGTTG
ATGGATGACGCCACACTCTGGGTCGAAGTGGGATCCCATCCCATTTGCTCGGGTATGATCAAGTCCACCTTTGGCCC
GCAGGCGACTACCGTTCCTTCGCTCCGCCGCGACGACGATCCATGGAAAATCCTCTCCAACAGCCTCTCCACGCTGC
ACCTTGCAGGCGTCGAGCTCAACTGGAAGGAATTCCACCAGGACTTCAGCTCGGCTCACGAGGTTCTCGAGTTACCC
CGGTACGGCTGGGATCTGAAGAATTACTGGATCCCCTACACGAACAACTTCTGCCTTACCAAGGGGGGTCCCGTTAC
CGCGGAGGTATCGGCGCCCAAGTCTACCTTCCTCACGACCGCGGCGCAAAAGATTGTGGAATGCCGGGAGGACGGAA
ACACGGCGACATTGGTAGTTGAGAATAATATCGCAGAGCCAGAACTCAACCGTGTTATCCAAGGTCACAAGGTCAAT
GGAGTGGCTCTTACGCCATCGGTGAGTTTGAACTGCACTCACCACTCTGGAATAGAAAGCTAATCCCTATACGTAGT
CTCTCTACGCTGATATTGCGCAAACGCTTGTCGACCACTTGATCACAAAATACAAACCAGAGTACCAGGGCCTAGGT
CTGGACGTGTGCGACATGACTGTGCCCAAGCCTCTCATAGCCAAGTCCGGAGATCAATTCTTCAGAGTCTCGGCGGT
GATGAGCTGGGCCGAGCAGAAGGCGAGCGTGCAAGTCTGGTCTGTGAACGGAGACGGCAAGAAAATGGCCGAGCACG
CCCATTGCACTGTCAAGCTCTTCAACTGCGCCGAGCGCGAGACGGAGTGGAAGAGAAACTCCTACCTCATCAAACGA
AGTGTCTCTCTCCTGCAGGACAAGGCGCAGACCGGCGAGGCTCACCGCATGCAGCGAGGAATGGTGTACAAGCTGTT
TGCTGCTCTGGTGGACTATGACGAAAACTTCAAGGCCATCCAGGAAGTCATCCTGGACAGCAATGAGCATGAAGCCA
CGGCGCGAGTCAAGTTCCAAGCCCCTCCGGGCAACTTCCACCGGAACCCCTTCTGGATCGATAGTTTCGGGCATCTG
TCTGGGTTCATCATGAATGCGAGCGATGCGACCGACTCCAAGAACCAGGTATTCGTCAACCACGGATGGGATTCCAT
```

-continued

```
GCGCTGCCTGAAGAAGTTCTCCGGCGACGCTACATACCAGACATATGTGAAGATGCAGCCGTGGAAGGACTCCATCT

GGGCGGGTGACGTCTATGTCTTTGAAGGGGATGACATTATCGCTGTGTACGGGGGGGTCAAGGTATGTCTCTAAATT

ACAATTGAAAAGAAAAAAAAAAAAAAAAAATAATTTTACTAACGGCGGCCTATACAGTTCCAAGCGCTGGCTCGAAA

GATCTTGGATACCGTTCTCCCTCCAATCGGAGGATCCAAGACCGTCGGTGCGCCGGCGCCGGCGCCAGCAAGGCCCA

TTGGGGAGAAGAAAGCTCCTCCCCCGATCAAGGTCACTGGTCCTCCCAAGCCCAACCCCAGCAACGCACGTGCTGCA

TCACCGGTGGTTGCACGGGCATTGGAGATCCTGGCTGCGGAGGTCGGTCTGTCCGAGGCTGAAATGACCGACAGTCT

CAACTTCGCCGACTACGGGGTCGACTCGCTGCTTTCCTTGACGGTGACCGGCAGGTATCGTGAAGAACTGAACCTTG

ATCTGGAATCGTCCGTGTTCATGGATTACCCGACCATCAAGGATTTCAAGGCCTACCTGGCCGAGAAGGGCTTCTGC

GACAGCAGCAGTCCCGAGCCGTCCAGCGAGCCCGAGTCCAAGTTCTCGTTCAACAGCGACGCATCATCCGAAGCTTC

CAGCGGACTTACCACTCCTGGAATTACATCTCCTGTGAAGCATGAGGCGCCCAAGGGCGGACAGAACAAAGTCTGGA

AAAGCATCTGCAGTATCATCGCCGAGGAAATCGGGGTGTCGGTCGGAGACATTGACCCGAGCGACAACTTGCCAGAG

ATGGGCATGGACTCGCTGCTGTCCCTGACCGTGCTCGGTCGGATCCGAGAGACACTTGGCATGGATCTGCCGGCAGA

GTTCTTCCTCGAGAACCCGACCCTCGATGCGGTGCAAGCTGCGCTGGATCTGAAGCCCAAGATGGTCCCCGCCGCGA

CGCCGGTCTCCGAACCCATCCGGCTCCTCGAGACAATCGACAACACGAAGCCCAAGACGTCTCGACATCCTCCGGCG

ACCTCGATTCTTCTCCAGGGCAACCCCCACACCGCCACCAAGAAGCTCTTCATGTTCCCGGACGGCTCGGGCTCCGC

CTCCTCCTACGCGACGATTCCGGCCCTCTCCCCGGATGTCTGTGTGTATGGTCTCAATTGCCCTTACATGAAGACGC

CTCAGAACCTCACGTGCAGTCTTGACGAGCTGACCGAGCCCTATCTGGCGGAGATCCGCCGACGTCAGCCCAAGGGA

CCGTACAGCTTTGGTGGTTGGTCGGCGGGTGGCATCTGCGCCTTTGACGCCGCGCGCCAGCTGATCCTCGAGGAAGG

GGAGGAGGTGGAGCGGTTGCTGCTGCTCGACTCGCCCTTCCCCATCGGTCTGGAGAAGCTGCCTCCTCGTCTGTACA

AGTTCTTCAACTCGATTGGGCTCTTTGGCGACGGGAAGCGGGCGCCTCCCGACTGGCTCCTCCCCCACTTCCTCGCC

TTCATCGACTCGCTCGACGCCTACAAAGCGGTTCCGCTGCCGTTCAACGACAGCAAATGGGCTAAGAAGATGCCCAA

GACCTACCTGATCTGGGCCAAGGACGGAGTCTGCGGCAAGCCGGGCGATCCCCGGCCGGAGCCTGCAGAGGATGGAT

CCGAGGACCCCCGCGAAATGCAGTGGCTGCTCAACGACCGAACGGATCTGGGACCAAACAAATGGGATACTTTGGTG

GGCCCGCAAAACATTGGCGGAATCCATGTGATGGAGGACGCGAATCATTTCACCATGACGACGGGACAGAAGGCGAA

GGAGTTGTCGCAATTCATGGCCACGGCCATGAGTTCCTAG
```

Description of Construct Designed to Mutate alb1 of *Aspergillus fumigatus*

The unshaded sequences are from *Aspergillus fumigatus* alb1 to help direct the knockout construct to the alb1 locus in the fungus. In this particular construct, the sequences with lighter gray shading are from the alcA gene of *Aspergillus nidulans* (GenBank: DQ076245.1), and the darker gray shaded sequences are from the brlA gene of *Aspergillus fumigatus* (GenBank: XM_747933.1). The construct SEQ ID NO:7 was assembled from known sequences.

```
Nucleotide sequence of the alb1 knock out construct
GATAGCGGCCGCCTTGCAGGCGAAGAACCATACTATCGTCGCCTCGTTCATCGAAAGATGCTTCCATGCACTGCGTC

AGGAAATCACCAGGCTGCCGCCTTCTCAGCGCACGCTCTTCCCGCGGTTTACCAGCATCGCCGACTTGCTTGCTCAG

CATCGTGAGTCAGGGACAAACCCTGCGCTGGGGAGCGCGCTGACCTGTATCTATCAACTGGGGTGTTTCATCGAGTA

AGTCGCCTTGCAAGGTATTCTGGACTGTGGCTGATCCTGGATAGTTACCACGGTGATCGTGGACATCCATATCCGTC

CTCGGATGACGGCCTTCTGGGTTCATGTACGGGTATGTTGAGTTGCACCGCAGTCAGCTCGTGCAAGAATGTCGGAG

AACTACTGCCGCTGGCAGTCGAGATTGTCAGATTGACTATCCACCTCGGGCTCTGTGTCATGAGAGTCCGAGAGATG

GTGGACTCGACGGAGTCATCCTCCGGCAGCTGGTCAATCCTCGTCTCGGAGATCAACGAGGCAGATGCCACCAGCCT

GATTGGCAATTTTGTCAAGAAGCGAGTAAGTACAGTGTACGACCATTGGAAGAAGAATATTGACAATACCAGGGAAT

TCCCCCCTCGTCGCAACCGTACATCAGCGCGGTTGGATCGAAAGGTCTCACCATCAGTGCACCACCCGAAATTCTCG

ACAACTTTATCGAAGAAGGTCTTCCGAAGGAGTACAAACACTTCAAGGCTCCTGGAGTCAGTGGTCCGTACCACGCG

CCCCATCTGTACAATGACCGAGAAATTCGCAATATCCTCAGCTTCTGCTCCGAGGACGTGATTCTGCGCCACACACC
```

-continued

```
ACGGGTTCCACTGGTCTCGAGCAACACAGGGAAGCTGGTCCAGGTAAAGAGCATGCGTGATCTGCTAAAGGTGGCTC

TGGAGGAAATCCTCTTGCGCAAGATCTGCTGGGACAAAGTCACCGAGTCATGCCTTTCCATCGTTCAGGCTACCAAC

GACAAGCCCTGGAGGATTCTCCCTATCGCCAGCAACGCCACGCAAGGCTTGGTTACTGCACTCCAGCGTATGGGAAA

CTGCCAGATCGAGGTAGACACCGGGGTCGGCGCTCCTCAAATGGACCCGGCCGCTCCCAATGCAACGGGCAATGCTT

CACGGTCTAAGATCGCCATCATCGGAATGTCTGGGCGGTTCCCTGAGGCAGATGGTATCGAGGCCTGGCGTTCCGTT

CTGCTTAGGGTATTTGGGAACAATCAATGTTCAATGTACATTTAATCCACGATTTTATAAAACGTCATCCTTTGCCC

TCCCTTCTTATTTGCCAATACCAAAAATCTTACTCCAGTGGTTCGGTAATCGCAGAGTTAAATCTGGGCTCGGTGGC

AGATCTGCGATGCTCCATAACCGTTCAGATGTTGATTGGAACTGGGTGGGGTAGACAGCTCGAAGACCGAGTGAACG

TATACCTAAGACACTTTGACACGGCCGGAACACTGTAAGTCCCTTCGTATTTCTCCGCCTGTGTGGAGCTACCATCC

AATAACCCCCAGCTGAAAAGCTGATTGTGATAGTTCCCACTTGTCCGTCCGCATCGGCATCCGCAGCTCGGGATAGT

TCCGACCTAGGATTGGATGCATGCGGAACCGCACGAGGGCGGGGCGGAAATTGACACACCACTCCTCTCCACGCACC

GTTCAAGAGGTACGCGTATAGAGCCGTATAGAGCAGAGACGGAGCACTTTCTGGTACTGTCCGCACGGGATGTCCGC

ACGGAGAGCCACAAACGAGCGGGGCCCCGTACGTGCTCTCCTACCCCAGGATCGCATCCCCGCATAGCTGAACATCT

ATATAAAGACCCCCAAGGTTCTCAGTCTCACCAACATCATCAACCAACAATCAACAGTTCTCTACTCAGTTAATTAG

AACTCTTCCAATCCTATCACCTCGCCTCAAAATGAGATCCCAGGCTAATATGTCTGATCGCCTGGGCGTTGAAGTCG

ACTGCCACTCACTCGGCTCCAACGAATGTCCGTCTATGGGCTCCAGCTTCTCGCCTTTGGAATCGCCCACACCTACC

CCTACGAGCATCTACAGTCAAGGTTCACTTGCTTCCCCAAGCTGGCCAGAAAACCGGTCATACCCGGGCCACGCTTA

CGACAGAGGTACCCGATCGACACCCATACGCGGCCACTTCCGTCTCGCCAGTATGCCCTCGCACGAGAACATGGGTC

TGCCACCATACAGCAGCCTGGATGGGCAGGATCGCATGGCGCTTACAGACTTCCTGCCTTCGTATGACGAGAACGCG

GATCAGTTCTGGCTCCCCTCGGATGTTCCCAAGACCTACGATCACCATGTCCATGGACTGCCATGCCCGCCGTCCAT

GCACCAATATCCGCCAATGCTTCGCAGCAACTACCGCCACCACCCCGCTCCGTATTTCCCTGAATCGGCCACCAACC

CGTGCCTGTCGCGCCCTATCTTCCATCATCAACCCGAGCGCCTGCCACCATCGTTATCCATGAGCCATATGATGCCC

TGGATGGGCCATACGGAGTCGATTGCACCGGAGACCATTGCTCCGTCCCAAGTTGCACCGGTAACCCCTCCTCCTTC

CTACACGGATTTCTCCAACTCTATCAACACCTTCAAGACGCACTCGCCGGACACCCCCATCCGCTCGTGCTCTCTAG

GCACTCGTCTCTGGAGCGGACACACCTTTGAGCCGTCTCTCTGGCGGCGCTGGTGAGTACATGGATGGTGCCACCAG

TCGCCTATCTACCGAGATGCGTCAGGCGTTCGTCTGCAGCGGCAGCCATCCCGCAAGATGGCGCGGAAGCACCTTC

CAAGCAGAGCTTGTCACTAGAGAACCTGCCATCCATCATCAACAGGTGCAGTTCAAGTGCAAAGAACCTGGCTGCA

AGGGTCGCTTCAAGCGACAGGAACACCTCAAGCGCCACATGAAGAGCCACTCCAAGGAAAAGCCTCATGTCTGCTGG

GTTCCTGGCTGCCATCGAGCCTTTTCACGCAGTGACAACCTCAATGCCCATTACACCAAGACCCACAGCAAACGCGG

AGGCCGGCAACCGCTATGTGGCCACCCTTGGATGAGACGAGTCCCGACTACAACCCGGACTATCGGGGGCCACTTACTG

CTGACGGTCGCCCCATGCCCGGTGGGACGCTGGACGAGTCCATGCCTTCCGGCGAGATCAGTATGGAATGGGATGAG

TAAAAAAAAAAGACGAAAAAGAAAACAAACAACAGAAAAAGAACAACAAGGATTTTCCTTCAAAACGAAACGG

AAGCTACCGACAGACTACGAAGAGATTAATGCGTGGATCGGAACCATGATACCCTTGTGACGCAGTCGACACAAAT

TTCCTTGAGTGATTTAGATGGGCACAGACATATAGGGTCCAAGAGACCCCGGTCGGCGCTTCGTGGCGTTATTTTTC

CCTGTCTTCAACCTCGCCCCCTTCCTTTTCCTGTTGTATAACATGCGTCCTGGCTTCGAATTCCTTGATTGGATGATG

CATCACCCCTTCAGGGTCACCGCAGTGGGGTCGAGCGTGAAGGATATCCGGGAGGTCCTGCGTCAACGTGCCGATCA
```

-continued

```
GGATGTCACCACCCCCGTCCCTGCGACAGCCCCCAAGACTGGGTTCGTCTTCACCGGTCAGGGAGCTCAGTACACAG

GGATGGGCAAGCAATTGTACGAGGACTGTGCCACATTCAGAAGCACGATTCACCGACTCGATTGCATTGCTCAAAGC

CAAGGGTTCCCCTCCATTCTACCGTTGATTGACGGTAGTATGCCTGTGGAAGAACTGAGCCCTGTCGTGACCCAGCT

AGGAACCACATGCCTGCAGATGGCTCTGGTCGACTACTGGAAGGGTCTTGGTGTCACTCCTGCGTTTGTTCTGGGAC

ATAGTCTGGGAGACTACGCAGCGTTGAACAGTGCGGGCGTCTTGTCCACCAGCGATACGATTTACCTCTGTGGCCGT

CGCGCGCAGCTTCTCACGCAGCAGTGTCAGATGGGGACCCACGCCATGCTTGCCGTCAAGGCTGCCGTCTCCGAGAT

TCAACATCTGCTCGATCCAGACGTCCACGCCGTCGCCTGCATCAATGGACCAACCGAAACGGTCATCAGCGGGCTCA

GCGGTCGAATCGATGAATTGGCACAGCAGTGCTCCAGCCAAAATCTCAAGTCCACCAAGCTCAAAGTGCCGTTCGCG

TTCCACTCGGCCCAAGTGGACCCGATTCTCGAGTCGTTCGAAGAGAGTGCTCAGGGGGTCATCTTCCACGAACCTGC

CGTCCCGTTCGTCTCTGCTCTGAACGGAGAGGTAATCACGGAGTCGAACTACAGCGTGCTGGGCCCCACGTATATGG

TGAAGCATTGTCGGGAAGCCGTCAATTTCCTTGGCGCTCTTGAGGCGACCCGGCACGCCAAGTTGATGGATGACGCC

ACACTCTGGGTCGAAGTGGGATCCCATCCCATTTGCTCGGGTATGATCAAGTCCACCTTTGGCGGCCGCAGAG
```

Whereas particular embodiments of this invention have been described for purposes of illustration, it will be understood by those persons skilled in the art that numerous variations of the details of the present invention may be made without departing from the invention as defined in the appended claims.

---

What is claimed is:

1. A method for producing lysergic acid comprising inactivating an ergot alkaloid biosynthesis pathway gene from the fungus *Aspergillus fumigatus* and expressing genes easA and cloA from the fungus *Epichloe* sp. Lp1, wherein said inactivated ergot alkaloid biosynthesis pathway gene is easA of *Aspergillus fumigatus*.

2. A method for producing ergot alkaloids comprising inactivating an ergot alkaloid biosynthesis pathway gene from the fungus *A. fumigatus* and expressing genes easA and cloA from the fungus *E.* sp. Lp1, wherein said inactivated ergot alkaloid biosynthesis pathway gene is easA of *A. fumigants*.

3. A method for producing dihydrolysergic acid (DHLA) comprising inactivating gene easM in *A. fumigatus* and expressing gene cloA from *Claviceps gigantea* or gene cloA from *Claviceps africana* in said *A. fumigatus* strain.

4. A method for producing dihydrolysergol (DHlysergol) comprising inactivating gene easM in *A. fumigatus* and expressing one or more genes of the ergot alkaloid biosynthesis from *Claviceps gigantea* selected from the group consisting of:
   a. cloA; and
   b. cloA and easA,
   wherein said gene(s) from *C. gigantea* are expressed in said *A. fumigants* strain.

5. A method of producing ergot alkaloids in a strain of *A. fumigatus* comprising expressing a bidirectional easA/easG promoter of *A. fumigatus* to drive expression of cloA oxidase genes in the *A. fumigatus* EasA knock-out background.

6. The method of claim 5, wherein a EasA gene from *E.* sp. Lp1 is expressed in said *A. fumigatus* EasA knock-out background.

7. The method of claim 6, wherein said EasA gene from *E.* sp. Lp1 includes expression of cloA.

8. A method for the production of lysergic acid comprising providing for the expression of ergot alkaloid producing fungi EasA/CloA in *A. fumigants* easA knockout or easM knockout.

9. A method for producing lysergic acid in *A. fumigatus* easA knock-out providing amplifying *E.* sp. Lp1 easA and *E.* sp. Lp1 cloA for producing lysergic acid.

10. A method for accumulating lysergol comprising amplifying easA and cloA from *Periglandula* in plant material selected from the group consisting of *Stictocardia tiliifolia*, *S. beraviensis*, *Argyreia*, and *Ipomoea* species or by amplifying easA and cloA from *Epichloë coenophiala* for accumulating lysergol.

11. A method for producing lysergol comprising providing expressing *Periglandula* sp. easA and *P.* sp. cloA or *Epichloë coenophiala* easA and *Epichloë coenophiala* cloA in a *A. fumigants* easA knock-out strain for producing lysergol.

12. A method for producing lysergol comprising *A. fumigatus* easA knock-out strain through expression of *E.* sp. Lp1 easA and *P.* sp. cloA or *Epichloë coenophiala* cloA for producing lysergol.

13. The method according to claim 12, including amplifying said easA and cloA based on degenerate primers designed to anneal to versions of each gene.

14. A method for producing dihydrolysergic acid comprising expressing *C. africana* cloA under the control of a *A. fumigatus* easA promoter in *A. fumigants* easM knock-out strain for producing dihydrolysergic acid.

15. A method for producing dihydrolysergic acid comprising expressing *C. africana* easA, *C. africana* cloA, and

*E*. sp. Lp1 cloA using a *A. fumigatus* easA/easG promoter in a *A. fumigatus* easM knock-out strain for producing dihydrolysergic acid.

16. A method for producing dihydrolysergol comprising expressing *C. gigantea* cloA in *A. fumigatus* easM knock-out for producing dihydrolysergol.

17. The method of claim 16, including joining said cloA to a easA promoter of *A. fumigatus* to form a cloA construct and introducing said cloA construct into *A. fumigants* easM knock-out utilizing cotransformation with pBCphleo.

18. The method of claim 17, including adding a *C. gigantea* easA operably linked to a *A. fumigants* easA promoter to said cotransformation of the *A. fumigatus* easM knockout.

* * * * *

SEQUENCE LISTING

<160> NUMBER OF SEQ ID NOS: 7

<210> SEQ ID NO 1
<211> LENGTH: 1131
<212> TYPE: DNA
<213> ORGANISM: Artificial Sequence
<220> FEATURE:
<223> OTHER INFORMATION: Aspergillus fumigatus easA
<220> FEATURE:
<221> NAME/KEY: Unsure
<222> LOCATION: (1)..(1131)

<400> SEQUENCE: 1

```
atgcgagaag aaccgtcctc tgctcagcta ttcaagccgc tcaaggtggg aagatgtcat      60
ctccaacata ggatgatcat ggcgccgaca actcgattcc gggccgatgg acaggggtc     120 ccgcttcctt ttgtacaaga gtattacggt cagcgtgcat cggttcctgg caccctcctc     180
atcaccgaag caacagacat caccccccaag gcgatgggtt acaaacatgt cccggggata     240
tggagtgagc cgcagcgcga ggcgtggaga gagattgttt ctagagtcca ttcgaaaaaa     300
tgctttattt tctgccagtt atgggcgacc ggccgcgccg cagatccgga cgtactcgcc     360
gacatgaagg acctgatctc tagtagcgcc gtgcctgtag aagagaaggg acctcttccc     420
cgagctctga ctgaggacga aatccagcag tgcatcgcag attttgcgca ggcggcccga     480
aacgccatca atgctgggtt cgatggggtg gagatccatg gtgccaatgg gtacctcatc     540
gaccagttca cacagaagtc ttgcaaccac cgccaggatc gatgggcgg aagcatcgag      600 aatcgagctc gttttgcggt cgaggtaaca cgggcggtta tcgaggccgt gggtgccgat     660
cgtgtcggcg tcaaactctc cccctacagt cagtatctgg ggatgggaac aatggacgag     720
cttgtgccac agtttgagta tctcattgcc cagatgcggc gattggatgt cgcatatctc     780
catcttgcca actcccgatg gcttgatgag gaaaagcccc atcctgaccc taatcatgag     840
gtgtttgtgc gtgtctgggg tcaatcctca cctatcctgc tggcaggcgg gtatgatgcg     900
gcatcggcag agaaggtgac ggagcagatg gcggcagcga cttacaccaa tgtggccatt     960
```

```
gcttttggga ggtactttat ctcgactcca gacctgccct ttcgggtcat ggctggcatc    1020
cagcttcaaa agtacgatcg tgcctctttc tatagcacgc tatcaagaga aggctacctt    1080 gattacccttt tcagcgctga atatatggca ttgcataatt tccccgtcta a            1131
```

<210> SEQ ID NO 2
<211> LENGTH: 1143
<212> TYPE: DNA
<213> ORGANISM: Artificial Sequence
<220> FEATURE:
<223> OTHER INFORMATION: Epichloe festucae var. lolii x Epichloe typhina
      isolate Lp1 easA
<220> FEATURE:
<221> NAME/KEY: Unsure
<222> LOCATION: (1)..(1143)

<400> SEQUENCE: 2

```
atgtcaactt caaatctttt cacgccgctc caatttggaa atgtctcct ccagcacaag      60 ctagtcctct caccgatgac tcgttttcgt gcggataatg aaggcgtccc gcttccctat    120
gtcaagactt actactgtca acgagcatct ctccctggca ccctgcttct taccgaagct    180
actgccatct ctcgccgagc cagagggttt cccaatgtcc ccgggatttg gagtcaggag    240
caaattgcag gctggaaaga ggtagttgat gctgtgcatg cgaaggggtc ttatatctgg    300
ctgcagcttt gggcgactgg acgagcagcc gaggttggtg ttctgaaagc gaatggattt    360
gatctcgtat ccagcagtgc cgttccagtc tccccggtg agcccacacc ccgggcgctc     420
agcgacgatg agatcaactc atacatcggt gatttcgttc aagcagccaa aaatgcagtc    480
ctagaagcag gatttgacgg agtcgaactc acggtgcca atggatttct catcgatcag     540
tttctccaat ctccttgcaa ccaacgtacc gatcaatggg gcggttgcat tgagaatcgc    600
tcacggttcg gtcttgaaat cacccggcga gtcatcgacg ctgtcggtaa agaccatgtg    660
ggcatgaagc tttccacttg gagtaccttc cagggaatgg gcaccatgga cgacctcata    720
cctcagttcg agcatttcat catgcgcctt cgtgagatag gcattgccta tctacacctt    780
gctaactctc gctgggtaga ggaggaagac cccaccatca gaacacatcc agatattcat    840
aatgagactt ttgtgcgcat gtgggggaaa gagaagcctg tccttttggc tggtggctac    900
ggcccggagt ccgccaagct tgtggtagat gaaacatact ctgaccacaa gaacatcgt     960 gtcgtttttg gacgcactaa tatccaacc cagatcttc cattccggct gaaaatggga     1020
ctccctcttc aaaagtacaa tcgggaaact ttctacattc cgttctctga cgagggatac    1080
ttggattacc cctatagtga ggaatacata acagagaaca gaagcaggc agttctagca    1140 taa                                                                  1143
```

<210> SEQ ID NO 3
<211> LENGTH: 2089
<212> TYPE: DNA
<213> ORGANISM: Artificial Sequence
<220> FEATURE:
<223> OTHER INFORMATION: Epichloe festucae var. lolii x Epichloe typhina
      isolate Lp1 cloA
<220> FEATURE:
<221> NAME/KEY: Unsure
<222> LOCATION: (1)..(2089)

<400> SEQUENCE: 3

```
atgatattac catggttatc ccagcttcaa tcggtctcac tagggacgat tttcctcacg     60
ctattcctcg ttatattgac tcctttggtt ttcacaagcg tttaccgtct gtattttcat    120
cctcttcgca aaattcctgg accacgaacc ggggggtttga caagtttcta tgggttctat   180
```

-continued

```
tggaactgga tacgagatga aggatactct aagctcttca atcccctgca taaacaatat    240
agtaaggttt atttcccgaa taaatacccc ttgtgaatgc taagatgcat caagattccc    300
atatcatacg tatcggccca aaccatgttc acatcaacca accgcaagct tttgatgagt    360
tcgtacaaga ctcctctaca cttctaaact gtggagggct cacacaaata aaaattagga    420
tattcaaagt tggaacaaca tggcgcaaag acagctcatt ttacaagtat tttaacggct    480
tggacgccat gattgagccg acgcaatatc gcacctaccg aactcacttg gccccttat     540
acgcacaacg ctccattgat ggcttaacac caaagctcca tgacgacctc gtggtaactg    600
ccgaaaggat ggccaagagc atcgaaaatg gtgaacctgt gaacatggtg aagatattgc    660
ggacattgag tgtaagtata tagtggttgt tcaaaaacca ctgtatttcg actaacggcc    720
aacgggaata gacctcaatg atgctttata ctttgtattc gcaggacatc ccgctctctc    780
aatatgatgg gtatcacccg tttctagaag cttttgagct gctcatgacc caaagttggc    840
taagtgagtc tgtatcacat ttcaggtcac agtttgcttt attgtataca ggaacgctga    900
taatttgttt ctgtacaaag tgatcaatta tcccatgatg ggtatgatcc ttggcctaat    960
tcccggcacg agctttgcga aattcaatgc cgctttcgga accttcttga aggttagtta   1020
acttgcggag taacaaggga caaagcacac aaattgctaa aagaatgtta atttacagta   1080
ctgtaaagag tggaacgacg aggatgaacg cattcaaaag cttgaaactg ctgaatcact   1140
gcgggactcc cacatgaaac gataccttgc cattgaccca aataacgaga tcaaaaagaa   1200
ggtcgtgccg catcccctgg aggatatatt taactttatc gcaggcggta gtgacactac   1260
ttcatataca gctgcatgtg cattcttcca tgttctctcg tcgtctgagg tgcactctaa   1320
gctcgtggcg gagctcgatc aagcttcttc agtgatcagg gataccttg  attacaataa   1380
gattcaaaac ttgccatatc tggtgtgtat acgattaaga gtttacctat catcattttt   1440
cccggaccct cttctgaaag taggctctaa ccatggatgt tgcagaatgc cgtgatcaag   1500
gagacgcttc gtatctcttg tccggtacca gggtgtcttc cccgagtcgt ccctgagggg   1560
ggaatgaatc tgggttcagt aaatcttcca gccggtgtaa gctccattta tacaaccttg   1620
tataagacta gtgacttgct aacgttgtga tatgcgaaca gacagtggtg tcaatctccc   1680
agctagccat ccactttaat gagacgattt tctcgtcacc tgacaagttc atccccgaaa   1740
gatggcttgg ggacgataga aaatcgattg agaagtggaa tatcgctttt agcagaggac   1800
ctcgacagtg cattgggaca acgtaagtct tccccccccc ccgatccggt gatagtatca   1860
aaataccacc attctctgct attgtagatg aatgaatgct gagttttaac gttttttgtt   1920
ccatagtctc gcttatatgg aactacgctg cgtcctcgct tatttcttct cccgctttga   1980
atttaagtta acgggtagct gtggagataa gttgcgctgg gttgatcgat ttgtctcagt   2040
caacttggac gatgtcgagg tcactatcgt gaaggaccga tgggcgtaa               2089
```
<210> SEQ ID NO 4
<211> LENGTH: 4917
<212> TYPE: DNA
<213> ORGANISM: Artificial Sequence
<220> FEATURE:
<223> OTHER INFORMATION: easA & cloA from E. festucae var lolii x E. typhina isolate Lp1 in A. fumigatus
<220> FEATURE:
<221> NAME/KEY: Unsure
<222> LOCATION: (1)..(4917)

<400> SEQUENCE: 4

```
cgtatcaccg agacaaagag gcgcatcatt cactatcaat tattttcaga gatatctaaa      60
tgaaacaaaa tgactacagt attgtataat gatcacggag caccaaagac taagaagaca     120
atgataaaga taacttaatg aacgaaatac aaaagccata ccacactagt gtacctattc     180
ggtataagat ttaactctta gaggaatcat ttataaggct aatccaaaag aatgcaaaag     240
cattgcctgg actgcgataa tgatttatgc tagaactgcc tgcttcttgt tctctgttat     300
gtattcctca ctatagggt aatccaagta tccctcgtca gagaacggaa tgtagaaagt      360
ttcccgattg tacttttgaa gagggagtcc cattttcagc cggaatggaa gatctgggtt     420
ggatatatag tgtcgtccaa aaacgacacc gatgttcttg tggtcagagt atgtttcatc     480
taccacaagc ttggcggact ccgggccgta gccaccagcc aaaaggacag gcttctcttt     540
cccccacatg cgcacaaaag tctcattatg aatatctgga tgtgttctga tggtggggtc     600
ttcctcctct acccagcgag agttagcaag gtgtagatag gcaatgccta tctcacgaag     660
gcgcatgatg aaatgctcga actgaggtat gaggtcgtcc atggtgccca ttccctggaa     720
ggtactccaa gtggaaagct tcatgcccac atggtctttta ccgacagcgt cgatgactcg     780
ccgggtgatt tcaagaccga accgtgagcg attctcaatg caaccgcccc attgatcggt     840
acgttggttg caaggagatt ggagaaactg atcgatgaga atccattgg caccgtggag      900
ttcgactccg tcaaatcctg cttctaggac tgcattttg gctgcttgaa cgaaatcacc      960
gatgtatgag ttgatctcat cgtcgctgag cgcccgggt gtgggctcac cggggggagac    1020
tggaacggca ctgctggata cgagatcaaa tccattcgct ttcagaacac caacctcggc    1080
tgctcgtcca gtcgcccaaa gctgcagcca gatataagac cccttcgcat gcacagcatc    1140
aactacctct ttccagcctg caatttgctc ctgactccaa atcccgggga cattgggaaa    1200
ccctctggct cggcgagaga tggcagtagc ttcggtaaga agcagggtgc cagggagaga    1260
tgctcgttga cagtagtaag tcttgacata gggaagcggg acgccttcat tatccgcacg    1320
aaaacgagtc atcggtgaga ggactagctt gtgctggagg agacattttc caaattggag    1380
cggcgtgaaa agatttgaag ttgacattgc ttctaatcca ccaagtactt ggaacacggt    1440
gaatgtcgaa gctcagtctg accagtggag gtatcgacgc gaacttttca ggtcatggaa    1500
gtgtggagta tggtctacag gcttggagga ctttgtattg attctggcat cgataactga    1560
gcagacaaga cgccattcgg gcacaatttc tttctgctgg acaattctca tacagccatg    1620
tcgtcccct tgccgagcca acgccactat ttgtttatgt gtctattatt cgatattcac    1680
ggggaaaggt gagctgactt gtacgtactc tgtctactcc aatgccctca cctttcttca    1740
gctgcagagc cgtggagcgg aactccttgc ttccccgttt acatacttgg gaattgaaat    1800
caggacccat atctccatga cgagtctttt atcatgcaca tgggaaatgg cggtcagtta    1860
aaacatgatc aatactactg ttacgccttt actccaatgc accgatagct aataagaaga    1920
gctcctccac cctcccacaa agaggcaagg gagagccaga agagactgag ggtggtgggc    1980
gaaaacagct ccaagcgtat atgtgctact gtgcccaaga cttcaccgta ctttctcaat    2040
gtgtgaataa tgaggactag acgagacact cttaataaga gatcatctac cagaaagggc    2100
gtacgttact accaaactct gtgtgattaa atgtacacac attctttcaa caaacaaatt    2160
tgatccatct tctatagagt aggcactccg caccatgata ttaccatggt tatcccagct    2220
tcaatcggtc tcactaggga cgattttcct cacgctattc ctcgttatat tgactccttt    2280
ggttttcaca agcgtttacc gtctgtattt tcatcctctt cgcaaaattc ctggaccacg    2340
aaccgggggt ttgacaagtt tctatggggtt ctattggaac tggatacgag atgaaggata   2400
```

```
ctctaagctc ttcaatcccc tgcataaaca atatagtaag gtttatttcc cgaataaata    2460 cccttgtga atgctaagat gcatcaagat tcccatatca tacgtatcgg cccaaaccat     2520
gttcacatca accaaccgca agcttttgat gagttcgtac aagactcctc tacacttcta    2580
aactgtggag ggctcacaca aataaaaatt aggatattca aagttggaac aacatggcgc    2640
aaagacagct cattttacaa gtattttaac ggcttggacg ccatgattga gccgacgcaa    2700
tatcgcacct accgaactca cttggcccct ttatacgcac aacgctccat tgatggctta    2760
acaccaaagc tccatgacga cctcgtggta actgccgaaa ggatggccaa gagcatcgaa    2820
aatggtgaac ctgtgaacat ggtgaagata ttgcggacat tgagtgtaag tatatagtgg    2880
ttgttcaaaa accactgtat ttcgactaac ggccaacggg aatagacctc aatgatgctt    2940
tatactttgt attcgcagga catcccgctc tctcaatatg atgggtatca cccgtttcta    3000
gaagcttttg agctgctcat gacccaaagt tggctaagtg agtctgtatc acatttcagg    3060
tcacagtttg ctttattgta tacaggaacg ctgataattt gtttctgtac aaagtgatca    3120
attatcccat gatgggtatg atccttggcc taattcccgg cacgagcttt gcgaaattca    3180
atgccgcttt cggaaccttc ttgaaggtta gttaacttgc ggagtaacaa gggacaaagc    3240
acacaaattg ctaaaagaat gttaatttac agtactgtaa agagtggaac gacgaggatg    3300
aacgcattca aaagcttgaa actgctgaat cactgcggga ctcccacatg aaacgatacc    3360
ttgccattga cccaaataac gagatcaaaa agaaggtcgt gccgcatccc ctggaggata    3420
tatttaactt tatcgcaggc ggtagtgaca ctacttcata tacagctgca tgtgcattct    3480
tccatgttct ctcgtcgtct gaggtgcact ctaagctcgt ggcggagctc gatcaagctt    3540
cttcagtgat cagggatacc tttgattaca ataagattca aaacttgcca tatctggtgt    3600
gtatacgatt aagagtttac ctatcatcat ttttcccgga ccctcttctg aaagtaggct    3660
ctaaccatgg atgttgcaga atgccgtgat caaggagacg cttcgtatct cttgtccggt    3720
accagggtgt cttccccgag tcgtccctga gggggaatg aatctgggtt cagtaaatct     3780
tccagccggt gtaagctcca tttatacaac cttgtataag actagtgact tgctaacgtt    3840
gtgatatgcg aacagacagt ggtgtcaatc tcccagctag ccatccactt taatgagacg    3900
attttctcgt cacctgacaa gttcatcccc gaaagatggc ttggggacga tagaaaatcg    3960
attgagaagt ggaatatcgc ttttagcaga ggacctcgac agtgcattgg acaacgtaa     4020 gtcttccccc cccccgatc cggtgatagt atcaaaatac caccattctc tgctattgta     4080
gatgaatgaa tgctgagttt taacgttttt tgttccatag tctcgcttat atggaactac    4140
gctgcgtcct cgcttatttc ttctcccgct ttgaatttaa gttaacgggt agctgtggag    4200
ataagttgcg ctgggttgat cgatttgtct cagtcaactt ggacgatgtc gaggtcacta    4260
tcgtgaagga ccgatgggcg taagctgaaa gcgtccaaaa gtgcccggga ggcgtaggca    4320
cggccagagg gatgtatctt gacttggaga aaattaaggg cgggaagcaa gttaaactag    4380
gatctttcca tagtactatt taatgagcta accctatgaa gtgtgagggg acaagggtat    4440
taacgagttc aaatgccgct tacatatagc gattttcac gagagacaga gattcctaaa     4500
tgccttagtt atattaagta actaaaaact gtaacttaag cctcgctagt aattgcacaa    4560
tatttataaa gtgagacatt tatcaaatat aaaagccaca tcgttctttt acgtggagca    4620
cattttagga gacatagga aaggtataag agggaacact gttacagtat tctcagactt     4680
tataataata acagtcaatg ttagagaaaa tatatggttc tttgagattt gttaacacag    4740
```

```
agccattaag acgttgttta ggcaatgtct taatagtggt gagttaccgc gtagtaatgt    4800
gcatgtattt taattagcca tagcaggcat acgtgccttt agttagttac ttatgcttat    4860
tgcttaccta aatacacgcc atacctaacg cttatcgctt gttgcccetta gcgtgtt      4917
```

<210> SEQ ID NO 5
<211> LENGTH: 5037
<212> TYPE: DNA
<213> ORGANISM: Artificial Sequence
<220> FEATURE:
<223> OTHER INFORMATION: Recipient strain Aspergillus fumigatus easA
      knockout
<220> FEATURE:
<221> NAME/KEY: Unsure
<222> LOCATION: (1)..(5037)

<400> SEQUENCE: 5

```
atgcgagaag aaccgtcctc tgctcagcta ttcaagccgc tcaaggtggg aagatgtcat      60
ctccaacata ggatgatcat ggcgccgaca actcgattcc gggccgatgg acaggggtc      120 ccgcttcctt ttgtacaaga gtattacggt cagcgtgcat cggttcctgg caccctcctc     180
atcaccgaag caacagacat caccccccaag gcgatgggtt acaaacatgt cccggggata    240
tggagtgagc cgcagcgcga ggcgtggaga gagattgttc tagagtcca ttcgaaaaaa      300 tgctttattt tctgccagtt atgggcgacc ggccgcgccg cagatccgga cgtactcgcc     360
gacatgaagg acctgatctc tagtagcgcc gtgcctgtag aagagaaggg acctcttccc     420
cgagctctga ctgaggacga aatccagcag tgcatcgcag atttgcgca ggcggcccga      480 aacgccatca atgctgggtt cgatggggtg gagatccatg gtgccaatgg gtacctcatc     540
gaccagttca cacagaagtc ttgcaaccac cgccaggatc gatgggcgg aagcatcgag      600 aatcgagctc gttttgcggt cgaggtaaca cgggcggtta tcgaggccgt gggtgccgat     660
cgtgtcggcg tcaaactctc cccctacagt cagtatctgg ggatgggaac aatggacgag     720
cttgtgccac agtttgagta tctcattgcc cagatgcggc gattggatgt cgcatatagc     780
gcccaatacg caaaccgcct ctccccgcgc gttggccgat tcattaatgc agctggcacg     840 acaggttttcc cgactggaaa gcgggcagtg agcgcaacgc aattaatgtg agttagctca     900
ctcattaggc accccaggct ttacacttta tgcttccggc tcgtatgttg tgtggaattg     960
tgagcggata caatttcac acaggaaaca gctatgacca tgattacgcc aagcttggta      1020
ccgagctcgg atccactagt aacggccgcc agtgtgctgg aattcggctt aagccgaatt    1080
ctgcagatat ccatcacact ggcggccgct cgagcatgca tctagagggc ccaattcgcc    1140
ctatagtgag tcgtattaca attcactggc cgtcgtttta caacgtcgtg actgggaaaa    1200
ccctggcgtt acccaactta atcgccttgc agcacatccc cctttcgcca gctggcgtaa    1260
tagcgaagag gcccgcaccg atcgcccttc ccaacagttg cgcagcctga atggcgaatg    1320
ggacgcgccc tgtagcggcg cattaagcgc ggcgggtgtg gtggttacgc gcagcgtgac    1380
cgctacactt gccagcgccc tagcgcccgc tcctttcgct ttcttccctt cctttctcgc    1440
cacgttcgcc ggctttcccc gtcaagctct aaatcggggg ctccctttag ggttccgatt    1500
tagagcttta cggcacctcg accgcaaaaa acttgatttg ggtgatggtt cacgtagtgg    1560
gccatcgccc tgatagacgg ttttcgccc tttgacgttg gagtccacgt tctttaatag    1620
tggactcttg ttccaaactg gaacaacact caaccctatc gcggtctatt cttttgattt    1680
ataagggatt ttgccgattt cggcctattg gttaaaaaat gagctgattt aacaaattca    1740
gggcgcaagg gctgctaaag gaaccggaac acgtagaaag ccagtccgca gaaacggtgc    1800
```

```
tgaccccgga tgaatgtcag ctactgggct atctggacaa gggaaaacgc aagcgcaaag    1860
agaaagcagg tagcttgcag tgggcttaca tggcgatagc tagactgggc ggttttatgg    1920
acagcaagcg aaccggaatt gccagctggg gcgccctctg gtaaggttgg gaagccctgc    1980
aaagtaaact ggatggcttt cttgccgcca aggatctgat ggcgcagggg atcaagatct    2040
gatcaagaga caggatgagg atcgtttcgc atgattgaac aagatggatt gcacgcaggt    2100
tctccggccg cttgggtgga gaggctattc ggctatgact gggcacaaca gacaatcggc    2160
tgctctgatg ccgccgtgtt ccggctgtca gcgcaggggc gcccggttct ttttgtcaag    2220
accgacctgt ccggtgccct gaatgaactg caggacgagg cagcgcggct atcgtggctg    2280
gccacgacgg gcgttccttg cgcagctgtg ctcgacgttg tcactgaagc gggaagggac    2340
tggctgctat tgggcgaagt gccggggcag gatctcctgt catctcgcct tgctcctgcc    2400
gagaaagtat ccatcatggc tgatgcaatg cggcggctgc atacgcttga tccggctacc    2460
tgcccattcg accaccaagc gaaacatcgc atcgagcgag cacgtactcg gatggaagcc    2520
ggtcttgtcg atcaggatga tctggacgaa gagcatcagg ggctcgcgcc agccgaactg    2580
ttcgccaggc tcaaggcgcg catgcccgac ggcgaggatc tcgtcgtgat ccatggcgat    2640
gcctgcttgc cgaatatcat ggtggaaaat ggccgctttt ctggattcaa cgactgtggc    2700
cggctgggtg tggcggaccg ctatcaggac atagcgttgg ataccgtga tattgctgaa    2760 gagcttggcg gcgaatgggc tgaccgcttc ctcgtgcttt acggtatcgc cgctcccgat    2820
tcgcagcgca tcgccttcta tcgccttctt gacgagttct tctgaattga aaaaggaaga    2880
gtatgagtat tcaacatttc cgtgtcgccc ttattccctt ttttgcggca ttttgccttc    2940 ctgttttgc tcacccagaa acgctggtga agtaaaaga tgctgaagat cagttgggtg    3000
cacgagtggg ttacatcgaa ctggatctca acagcggtaa gatccttgag agttttcgcc    3060
ccgaagaacg ttttccaatg atgagcactt taaagttct gctatgtcat acactattat    3120
cccgtattga cgccgggcaa gagcaactcg gtcgccgggc gcggtattct cagaatgact    3180
tggttgagta ctcaccagtc acagaaaagc atcttacgga tggcatgaca gtaagagaat    3240
tatgcagtgc tgccataacc atgagtgata acactgcggc caacttactt ctgacaacga    3300
tcggaggacc gaaggagcta accgcttttt tgcacaacat gggggatcat gtaactcgcc    3360
ttgatcgttg ggaaccggag ctgaatgaag ccataccaaa cgacgagagt gacaccacga    3420
tgcctgtagc aatgccaaca acgttgcgca aactattaac tggcgaacta cttactctag    3480
cttcccggca caattaata gactggatgg aggcggataa agttgcagga ccacttctgc    3540
gctcggccct tccggctggc tggtttattg ctgataaatc tggagccggt gagcgtgggt    3600
ctcgcggtat cattgcagca ctggggccag atggtaagcc ctcccgtatc gtagttatct    3660
acacgacggg gagtcaggca actatggatg aacgaaatag acagatcgct gagataggtg    3720
cctcactgat taagcattgg taactgtcag accaagttta ctcatatata ctttagattg    3780
atttaaaact tcattttta tttaaaagga tctaggtgaa gatcctttt gataatctca    3840 tgaccaaaat cccttaacgt gagttttcgt tccactgagc gtcagacccc gtagaaaaga    3900
tcaaaggatc ttcttgagat cctttttttc tgcgcgtaat ctgctgcttg caaacaaaaa    3960
aaccaccgct accagcggtg gtttgtttgc cggatcaaga gctaccaact cttttttccga    4020 aggtaactgg cttcagcaga gcgcagatac caaatactgt ccttctagtg tagccgtagt    4080
taggccacca cttcaagaac tctgtagcac cgcctacata cctcgctctg ctaatcctgt    4140
```

```
taccagtggc tgctgccagt ggcgataagt cgtgtcttac cgggttggac tcaagacgat    4200
agttaccgga taaggcgcag cggtcgggct gaacgggggg ttcgtgcaca cagcccagct    4260
tggagcgaac gacctacacc gaactgagat acctacagcg tgagcattga gaaagcgcca    4320
cgcttcccga agggagaaag gcggacaggt atccggtaag cggcagggtc ggaacaggag    4380
agcgcacgag ggagcttcca gggggaaacg cctggtatct ttatagtcct gtcgggtttc    4440
gccacctctg acttgagcgt cgattttttgt gatgctcgtc aggggggcgg agcctatgga    4500
aaaacgccag caacgcggcc tttttacggt tcctggcctt ttgctggcct tttgctcaca    4560
tgttctttcc tgcgttatcc cctgattctg tggataaccg tattaccgcc tttgagtgag    4620
ctgataccgc tcgccgcagc cgaacgaccg agcgcagcga gtcagtgagc gaggaagcgg    4680
aagctccatc ttgccaactc ccgatggctt gatgaggaaa agccccatcc tgaccctaat    4740
catgaggtgt tgtgcgtgt ctggggtcaa tcctcaccta tcctgctggc aggcgggtat    4800
gatgcggcat cggcagagaa ggtgacggag cagatggcgg cagcgactta caccaatgtg    4860
gccattgctt ttgggaggta ctttatctcg actccagacc tgcccttcg ggtcatggct    4920 ggcatccagc ttcaaaagta cgatcgtgcc tctttctata gcacgctatc aagagaaggc    4980
taccttgatt acccttttcag cgctgaatat atggcattgc ataatttccc cgtctaa     5037
```

<210> SEQ ID NO 6
<211> LENGTH: 6662
<212> TYPE: DNA
<213> ORGANISM: Artificial Sequence
<220> FEATURE:
<223> OTHER INFORMATION: disarmed strain of Aspergillus fumigatus
<220> FEATURE:
<221> NAME/KEY: Unsure
<222> LOCATION: (1)..(6662)

<400> SEQUENCE: 6

```
atggaggatc tccatcgcct ctatctcttt ggagatcaga caatcagctg tgacgaaggc      60
ctccgcaacc tcttgcaggc gaagaaccat actatcgtcg cctcgttcat cgaaagatgc     120
ttccatgcac tgcgtcagga aatcaccagg ctgccgcctt tcagcgcac gctcttcccg      180 cggtttacca gcatcgccga cttgcttgct cagcatcgtg agtcagggac aaaccctgcg     240
ctggggagcg cgctgacctg tatctatcaa ctggggtgtt tcatcgagta agtcgccttg     300
caaggtattc tggactgtgg ctgatcctgg atagttacca cggtgatcgt ggacatccat     360
atccgtcctc ggatgacggc cttctgggtt catgtacggg tatgttgagt tgcaccgcag     420
tcagctcgtg caagaatgtc ggagaactac tgccgctggc agtcgagatt gtcagattga     480
ctatccacct cgggctctgt gtcatgagag tccgagagat ggtggactcg acggagtcat     540
cctccggcag ctggtcaatc ctcgtctcgg agatcaacga gcagatgcc accagcctga     600 ttggcaattt tgtcaagaag cgagtaagta cagtgtacga ccattggaag aagaatattg     660
acaataccag ggaattcccc cctcgtcgca accgtacatc agcgcggttg gatcgaaagg     720
tctcaccatc agtgcaccac ccgaaattct cgacaacttt atcgaagaag gtcttccgaa     780
ggagtacaaa cacttcaagg ctcctggagt cagtggtccg taccacgcgc cccatctgta     840
caatgaccga gaaattcgca atatcctcag cttctgctcc gaggacgtga ttctgcgcca     900
cacaccacgg gttccactgg tctcgagcaa cacaggaag ctggtccagg taaagagcat     960
gcgtgatctg ctaaaggtgg ctctggagga atcctcttg cgcaagatct gctgggacaa    1020
agtcaccgag tcatgccttt ccatcgttca ggctaccaac gacaagccct ggaggattct    1080
```

```
ccctatcgcc agcaacgcca cgcaaggctt ggttactgca ctccagcgta tgggaaactg    1140
ccagatcgag gtagacaccg gggtcggcgc tcctcaaatg gacccggccg ctcccaatgc    1200
aacgggcaat gcttcacggt ctaagatcgc catcatcgga atgtctgggc ggttccctga    1260
ggcagatggt atcgaggcct tttgggactt gttgtataaa ggtctggatg ttcacaaaaa    1320
ggtcccacct gagcgatggg atgtggacgc gcacgtggac ttgaccggca caagagaaa    1380 caccagcaag gtcccatacg gttgctggat caacgagccc ggcctgttcg atgcccgttt    1440
cttcaacatg tctcctcggg aagcactcca ggcagaccct gcgcagcgac tggcgctgct    1500
gtcggcttac gaggccctgg aaatggcagg cttcgttccg aacagcagtc catcgactca    1560
gagagaccgc gtcggcatct tcatgggtat gaccagcgac gactaccgtg agatcaacag    1620
cggtcaggat atcgacacat acttcattcc tggagggaac cgagcattca cgcctggtcg    1680
tatcaactac tacttcaagt tcagtgggcc tagtgtcagt gtcgacaccg cctgctcgtc    1740
cagtcttgct gccatccact ggcctgcaa cgccatctgg aggaatgact gcgataccgc    1800
catcagtggt ggtgtaaacc tccttactaa cccggacaac catgccggtc tggatcgcgg    1860
ccactttctg tctcggacag gaaactgcaa caccttcgac gacggcgcgg atggctactg    1920
ccgggcggac ggggtgggca cgatcgtcct gaagcgcctg gaggatgctg aggctgacaa    1980
cgatcccatt ctgggagtca ttaacgcggc ctacaccaac cactcggccg aagccgtctc    2040
cattacccgc cctcacgtcg gcgcgcaggc gttcatcttc aacaagctcc tcaacgacac    2100
caacaccaac ccacacgaga ttggctacgt ggaaatgcac ggaacaggta ctcaggcggg    2160
cgacgccgtt gagatgcagt ccgtcctcga cgtcttcgca cccgactacc gccgcgggcc    2220
ggccaattcc ctttatctgg gttccgccaa atcgaacatc ggccacgggg aatcagcttc    2280
cggagtgaca tccttggtca aggtcctgtt gatgttgaag cagaacatga tcccgcccca    2340
ctgcggaatc aaaacaaaga tcaatcacaa cttccccacg gatctggccc agcgcaatgt    2400
ccatattgcc ttcaagccaa cccctggaa cagaccggtc tcgggcaagc ggaagatgtt    2460
catcaacaac ttctctgctg cgggcggcaa caccgctctc ctgatggaag atgccccct    2520 gcgtgagatc acagggcagg atccccggaa tgtgcatgtg tgtctgtga cggcacggtc    2580 gcagactgcg ctgaagcgta acatcaacgc gttgatcaag tacatcaaca cgcatgcgcc    2640
ctcgtcgccg gcgaatgagc gacggttcct ggccagtctg gcttatacta ctaccgcgcg    2700
tcgcatgcat caccccttca gggtcaccgc agtggggtcg agcgtgaagg atatccggga    2760
ggtcctgcgt caacgtgccg atcaggatgt caccaccccc gtccctgcga cagccccaa    2820 gactgggttc gtcttcaccg gtcagggagc tcagtacaca gggatgggca agcaattgta    2880
cgaggactgt gccacattca gaagcacgat tcaccgactc gattgcattg ctcaaagcca    2940
agggttcccc tccattctac cgttgattga cggtagtatg cctgtggaag aactgagccc    3000
tgtcgtgacc cagctaggaa ccacatgcct gcagatggct ctggtcgact actgaaggg    3060 tcttggtgtc actcctgcgt tgttctggg acatagtctg ggagactacg cagcgttgaa    3120
cagtgcgggc gtcttgtcca ccagcgatac gatttacctc tgtggccgtc gcgcgcagct    3180
tctcacgcag cagtgtcaga tggggaccca cgccatgctt gccgtcaagg ctgccgtctc    3240
cgagattcaa catctgctcg atccagacgt ccacgccgtc gcctgcatca atggaccaac    3300
cgaaacggtc atcagcgggc tcagcggtcg aatcgatgaa ttggcacagc agtgctccag    3360
ccaaaatctc aagtccacca agctcaaagt gccgttcgcg ttccactcgg cccaagtgga    3420
cccgattctc gagtcgttcg aagagagtgc tcaggggtc atcttccacg aacctgccgt    3480
```

```
cccgttcgtc tctgctctga acggagaggt aatcacggag tcgaactaca gcgtgctggg    3540
ccccacgtat atggtgaagc attgtcggga agccgtcaat ttccttggcg ctcttgaggc    3600
gacccggcac gccaagttga tggatgacgc cacactctgg gtcgaagtgg atcccatcc    3660
catttgctcg gtatgatca agtccacctt tggcccgcag gcgactaccg ttccttcgct    3720
ccgccgcgac gacgatccat ggaaaatcct ctccaacagc ctctccacgc tgcaccttgc    3780
aggcgtcgag ctcaactgga aggaattcca ccaggacttc agctcggctc acgaggttct    3840
cgagttaccc cggtacggct gggatctgaa gaattactgg atcccctaca cgaacaactt    3900
ctgccttacc aagggggggtc ccgttaccgc ggaggtatcg gcgcccaagt ctaccttcct    3960
cacgaccgcg gcgcaaaaga ttgtggaatg ccgggaggac ggaaacacgg cgacattggt    4020
agttgagaat aatatcgcag agccagaact caaccgtgtt atccaaggtc acaaggtcaa    4080
tggagtggct cttacgccat cggtgagttt gaactgcact caccactctg gaatagaaag    4140
ctaatcccta tacgtagtct ctctacgctg atattgcgca aacgcttgtc gaccacttga    4200
tcacaaaata caaaccagag taccagggcc taggtctgga cgtgtgcgac atgactgtgc    4260
ccaagcctct catagccaag tccggagatc aattcttcag agtctcggcg gtgatgagct    4320
gggccgagca gaaggcgagc gtgcaagtct ggtctgtgaa cggagacggc aagaaaatgg    4380
ccgagcacgc ccattgcact gtcaagctct tcaactgcgc cgagcgcgag acggagtgga    4440
agagaaactc ctacctcatc aaacgaagtg tctctctcct gcaggacaag cgcagaccg    4500
gcgaggctca ccgcatgcag cgaggaatgg tgtacaagct gtttgctgct ctggtggact    4560
atgacgaaaa cttcaaggcc atccaggaag tcatcctgga cagcaatgag catgaagcca    4620
cggcgcgagt caagttccaa gcccctccgg gcaacttcca ccggaaccc ttctggatcg    4680
atagtttcgg gcatctgtct gggttcatca tgaatgcgag cgatgcgacc gactccaaga    4740
accaggtatt cgtcaaccac ggatgggatt ccatgcgctg cctgaagaag ttctccggcg    4800
acgctacata ccagacatat gtgaagatgc agccgtggaa ggactccatc tgggcgggtg    4860
acgtctatgt ctttgaaggg gatgacatta tcgctgtgta cggggggtc aaggtatgtc    4920
tctaaattac aattgaaaag aaaaaaaaaa aaaaaaaata atttactaa cggcggccta    4980
tacagttcca agcgctggct cgaaagatct tggataccgt tctccctcca atcggaggat    5040
ccaagaccgt cggtgcgccg gcgccggcgc cagcaaggcc cattgggag aagaaagctc    5100
ctcccccgat caaggtcact ggtcctccca agcccaaccc cagcaacgca cgtgctgcat    5160
caccggtggt tgcacgggca ttggagatcc tggctgcgga ggtcggtctg tccgaggctg    5220
aaatgaccga cagtctcaac ttcgccgact acggggtcga ctcgctgctt tccttgacgg    5280
tgaccggcag gtatcgtgaa gaactgaacc ttgatctgga atcgtccgtg ttcatggatt    5340
acccgaccat caaggatttc aaggcctacc tggccgagaa gggcttctgc gacagcagca    5400
gtcccgagcc gtccagcgag cccgagtcca agttctcgtt caacagcgac gcatcatccg    5460
aagcttccag cggacttacc actcctggaa ttacatctcc tgtgaagcat gaggcgccca    5520
agggcggaca gaacaaagtc tggaaaagca tctgcagtat catcgccgag gaaatcgggg    5580
tgtcggtcgg agacattgac ccgagcgaca acttgccaga gatgggcatg gactcgctgc    5640
tgtccctgac cgtgctcggt cggatccgag agacacttgg catggatctg ccggcagagt    5700
tcttcctcga gaacccgacc ctcgatgcgg tgcaagctgc gctggatctg aagcccaaga    5760
tggtccccgc cgcgacgccg gtctccgaac ccatccggct cctcgagaca atcgacaaca    5820
```

|  |  |  |  |  |  |
|---|---|---|---|---|---|
| cgaagcccaa | gacgtctcga | catcctccgg | cgacctcgat | tcttctccag ggcaaccccc | 5880 |
| acaccgccac | caagaagctc | ttcatgttcc | cggacggctc | gggctccgcc tcctcctacg | 5940 |
| cgacgattcc | ggccctctcc | ccggatgtct | gtgtgtatgg | tctcaattgc ccttacatga | 6000 |
| agacgcctca | gaacctcacg | tgcagtcttg | acgagctgac | cgagccctat ctggcggaga | 6060 |
| tccgccgacg | tcagcccaag | ggaccgtaca | gctttggtgg | ttggtcggcg ggtggcatct | 6120 |
| gcgcctttga | cgccgcgcgc | cagctgatcc | tcgaggaagg | ggaggaggtg gagcggttgc | 6180 |
| tgctgctcga | ctcgcccttc | cccatcggtc | tggagaagct | gcctcctcgt ctgtacaagt | 6240 |
| tcttcaactc | gattgggctc | tttggcgacg | ggaagcgggc | gcctcccgac tggctcctcc | 6300 |
| cccacttcct | cgccttcatc | gactcgctcg | acgcctacaa | agcggttccg ctgccgttca | 6360 |
| acgacagcaa | atgggctaag | aagatgccca | agacctacct | gatctgggcc aaggacggag | 6420 |
| tctgcggcaa | gccgggcgat | ccccggccgg | agcctgcaga | ggatggatcc gaggaccccc | 6480 |
| gcgaaatgca | gtggctgctc | aacgaccgaa | cggatctggg | accaaacaaa tgggatactt | 6540 |
| tggtgggccc | gcaaaacatt | ggcggaatcc | atgtgatgga | ggacgcgaat catttcacca | 6600 |
| tgacgacggg | acagaaggcg | aaggagttgt | cgcaattcat | ggccacggcc atgagttcct | 6660 |
| ag |  |  |  |  | 6662 |

<210> SEQ ID NO 7
<211> LENGTH: 4539
<212> TYPE: DNA
<213> ORGANISM: Artificial Sequence
<220> FEATURE:
<223> OTHER INFORMATION: mutate alb1 of Aspergillus fumigatus
<220> FEATURE:
<221> NAME/KEY: Unsure
<222> LOCATION: (1)..(4539)

<400> SEQUENCE: 7

```
gatagcggcc gccttgcagg cgaagaacca tactatcgtc gcctcgttca tcgaaagatg     60
cttccatgca ctgcgtcagg aaatcaccag gctgccgcct tctcagcgca cgctcttccc    120
gcggtttacc agcatcgccg acttgcttgc tcagcatcgt gagtcaggga caaaccctgc    180
gctggggagc gcgctgacct gtatctatca actggggtgt ttcatcgagt aagtcgcctt    240
gcaaggtatt ctggactgtg gctgatcctg gatagttacc acggtgatcg tggacatcca    300
tatccgtcct cggatgacgg ccttctgggt tcatgtacgg gtatgttgag ttgcaccgca    360
gtcagctcgt gcaagaatgt cggagaacta ctgccgctgg cagtcgagat tgtcagattg    420
actatccacc tcgggctctg tgtcatgaga gtccgagaga tggtggactc gacggagtca    480
tcctccggca gctggtcaat cctcgtctcg gagatcaacg aggcagatgc caccagcctg    540
attggcaatt ttgtcaagaa gcgagtaagt acagtgtacg accattggaa gaagaatatt    600
gacaatacca gggaattccc ccctcgtcgc aaccgtacat cagcgcggtt ggatcgaaag    660
gtctcaccat cagtgcacca cccgaaattc tcgacaactt tatcgaagaa ggtcttccga    720
aggagtacaa acacttcaag gctcctggag tcagtggtcc gtaccacgcg ccccatctgt    780
acaatgaccg agaaattcgc aatatcctca gcttctgctc cgaggacgtg attctgcgcc    840
acacaccacg ggttccactg gtctcgagca acacagggaa gctggtccag gtaaagagca    900
tgcgtgatct gctaaaggtg gctctggagg aaatcctctt gcgcaagatc tgctgggaca    960
aagtcaccga gtcatgcctt tccatcgttc aggctaccaa cgacaagccc tggaggattc   1020
tccctatcgc cagcaacgcc acgcaaggct tggttactgc actccagcgt atgggaaact   1080
```

```
gccagatcga ggtagacacc ggggtcggcg ctcctcaaat ggacccggcc gctcccaatg    1140
caacgggcaa tgcttcacgg tctaagatcg ccatcatcgg aatgtctggg cggttccctg    1200
aggcagatgg tatcgaggcc tggcgttccg ttctgcttag ggtatttggg aacaatcaat    1260
gttcaatgta catttaatcc acgattttat aaaacgtcat cctttgccct cccttcttat    1320
ttgccaatac caaaaatctt actccagtgg ttcggtaatc gcagagttaa atctgggctc    1380
ggtggcagat ctgcgatgct ccataaccgt tcagatgttg attggaactg ggtggggtag    1440
acagctcgaa gaccgagtga acgtatacct aagacacttt gacacggccg gaacactgta    1500
agtcccttcg tatttctccg cctgtgtgga gctaccatcc aataacccc agctgaaaag     1560 ctgattgtga tagttcccac ttgtccgtcc gcatcggcat ccgcagctcg ggatagttcc    1620
gacctaggat tggatgcatg cggaaccgca cgagggcggg gcggaaattg acacaccact    1680
cctctccacg caccgttcaa gaggtacgcg tatagagccg tatagagcag agacggagca    1740
ctttctggta ctgtccgcac gggatgtccg cacggagagc cacaaacgag cggggccccg    1800
tacgtgctct cctaccccag gatcgcatcc ccgcatagct gaacatctat ataaagaccc    1860
ccaaggttct cagtctcacc aacatcatca accaacaatc aacagttctc tactcagtta    1920
attagaactc ttccaatcct atcacctcgc ctcaaaatga gatcccaggg taatatgtct    1980
gatcgcctgg gcgttgaagt cgactgccac tcactcggct ccaacgaatg tccgtctatg    2040
ggctccagct tctcgccttt ggaatcgccc acacctaccc ctacgagcat ctacagtcaa    2100
ggttcacttg cttccccaag ctggccagaa acgggtcat acccgggcca cgcttacgac      2160
agaggtaccg gatcgacacc catacgcggc cacttccgtc tcgccagtat gccctcgcac    2220
gagaacatgg gtctgccacc atacagcagc ctggatgggc aggatcgcat ggcggttaca    2280
gacttcctgc cttcgtatga cgagaacgcg gatcagttct ggctcccctc ggatgttccc    2340
aagacctacg atcaccatgt ccatggactg ccatgcccgc cgtccatgca ccaatatccg    2400
ccaatgcttc gcagcaacta ccgccaccac cccgctccgt atttccctga atcgccacc     2460 aacccgtgcc tgtcgcgccc tatcttccat catcaacccg agcgcctgcc accatcgtta    2520
tccatgagcc atatgatgcc ctggatgggc catacggagt cgattgcacc ggagaccatt    2580
gctccgtccc aagttgcacc ggtaacccct cctccttcct acacggattt ctccaactct    2640
atcaacacct tcaagacgca ctcgccggac accccatcc gctcgtgctc tctaggcact     2700
gtctctggag cggacacacc tttgagccgt ctctctggcg gcgctggtga gtacatggat    2760
gaatgccacc agtcgcctat ctaccgagat gcgtcaggcg ttcgtctgca gcggcagcca    2820
tcccgcaaga tggcgcggaa gcagccttcc aagcagagct tgtcactaga gaacctgcca    2880
tccatcatca gcaggtgca gttcaagtgc aaagaacctg gctgcaaggg tcgcttcaag      2940
cgacaggaac acctcaagcg ccacatgaag agccactcca aggaaaagcc tcatgtctgc    3000
tgggttcctg gctgccatcg agccttttca cgcagtgaca acctcaatgc ccattacacc    3060
aagacccaca gcaaacgcgg aggccgcaac cgctatgtgg ccaccttgga tgagacgagt    3120
cccgactaca acccggacta tcgggggcca cttactgctg acggtcgccc catgcccggt    3180
gggacgctgg acgagtccat gccttcccgc gagatcagta tggaatggga tgagtaaaaa    3240
aaaaaagacg aaaaaagaaa acaaagaaga gaaaaaagaa caagaaggat ttttccttca    3300
aaacgaaacg gaagctaccg acagactacg aagagattaa tgggtggatc ggaaccatga    3360 taccccttgtg acgcagtcga cacaaaattt ccttgagtga tttagatggg cacagacata    3420
tagggtccaa gagacccgg tcggcgcttc gtggcgttat ttttccttgt cttcaacctc     3480
```

-continued

```
ccccttcct tttcctgttg tataacatgc gtcctgggtt cgaattcctt gattggatga    3540
tgcatcaccc cttcagggtc accgcagtgg ggtcgagcgt gaaggatatc cgggaggtcc    3600
tgcgtcaacg tgccgatcag gatgtcacca ccccgtccc tgcgacagcc cccaagactg     3660
ggttcgtctt caccggtcag ggagctcagt acacagggat gggcaagcaa ttgtacgagg    3720
actgtgccac attcagaagc acgattcacc gactcgattg cattgctcaa agccaagggt    3780
tcccctccat tctaccgttg attgacggta gtatgcctgt ggaagaactg agccctgtcg    3840
tgacccagct aggaaccaca tgcctgcaga tggctctggt cgactactgg aagggtcttg    3900
gtgtcactcc tgcgtttgtt ctgggacata gtctgggaga ctacgcagcg ttgaacagtg    3960
cgggcgtctt gtccaccagc gatacgattt acctctgtgg ccgtcgcgcg cagcttctca    4020
cgcagcagtg tcagatgggg acccacgcca tgcttgccgt caaggctgcc gtctccgaga    4080
ttcaacatct gctcgatcca gacgtccacg ccgtcgcctg catcaatgga ccaaccgaaa    4140
cggtcatcag cgggctcagc ggtcgaatcg atgaattggc acagcagtgc tccagccaaa    4200
atctcaagtc caccaagctc aaagtgccgt tcgcgttcca ctcggcccaa gtggacccga    4260
ttctcgagtc gttcgaagag agtgctcagg gggtcatctt ccacgaacct gccgtcccgt    4320
tcgtctctgc tctgaacgga gaggtaatca cggagtcgaa ctacagcgtg ctgggcccca    4380
cgtatatggt gaagcattgt cgggaagccg tcaatttcct tggcgctctt gaggcgaccc    4440
ggcacgccaa gttgatggat gacgccacac tctgggtcga agtgggatcc catcccattt    4500
gctcgggtat gatcaagtcc acctttggcg gccgcagag                          4539
```